US009773091B2

(12) United States Patent
Torkamani et al.

(10) Patent No.: US 9,773,091 B2
(45) Date of Patent: *Sep. 26, 2017

(54) SYSTEMS AND METHODS FOR GENOMIC ANNOTATION AND DISTRIBUTED VARIANT INTERPRETATION

(71) Applicant: THE SCRIPPS RESEARCH INSTITUTE, La Jolla, CA (US)

(72) Inventors: Ali Torkamani, San Diego, CA (US); Nicholas Schork, Solana Beach, CA (US)

(73) Assignee: The Scripps Research Institute, La Jolla, CA (US)

( * ) Notice: Subject to any disclaimer, the term of this patent is extended or adjusted under 35 U.S.C. 154(b) by 266 days.

This patent is subject to a terminal disclaimer.

(21) Appl. No.: 14/200,520

(22) Filed: Mar. 7, 2014

(65) Prior Publication Data

US 2014/0304270 A1  Oct. 9, 2014

Related U.S. Application Data

(63) Continuation-in-part of application No. PCT/US2012/062787, filed on Oct. 31, 2012.

(60) Provisional application No. 61/553,576, filed on Oct. 31, 2011, provisional application No. 61/676,885, filed on Jul. 27, 2012, provisional application No. 61/852,255, filed on Mar. 15, 2013.

(51) Int. Cl.
  *G06F 17/30* (2006.01)
  *G06F 19/24* (2011.01)
  *G06F 19/18* (2011.01)

(52) U.S. Cl.
  CPC .............. *G06F 19/24* (2013.01); *G06F 19/18* (2013.01)

(58) Field of Classification Search
  CPC combination set(s) only.
  See application file for complete search history.

(56) References Cited

U.S. PATENT DOCUMENTS

| 6,023,659 A * | 2/2000 | Seilhamer ............... G06F 19/28 |
| | | 702/19 |
| 6,462,190 B1 | 10/2002 | Michikawa et al. |
| 6,772,160 B2 | 8/2004 | Cho et al. |
| 7,660,709 B2 | 2/2010 | Bugrim et al. |

(Continued)

FOREIGN PATENT DOCUMENTS

| WO | WO 00/57309 A2 | 9/2000 |
| WO | WO 2005/071058 A2 | 8/2005 |

(Continued)

OTHER PUBLICATIONS

Boeckmann et al., The SWISS-PROT protein knowledgebase and its supplement TrEMBL in 2003, Nucl. Acids Res. (2003) 31 (1): 365-370.

(Continued)

*Primary Examiner* — Shyue Jiunn Hwa
(74) *Attorney, Agent, or Firm* — Knobbe, Martens, Olson & Bear, LLP

(57) ABSTRACT

A computer-based genomic annotation system, including a database configured to store genomic data, non-transitory memory configured to store instructions, and at least one processor coupled with the memory, the processor configured to implement the instructions in order to implement an annotation pipeline and at least one module filtering or analysis of the genomic data.

14 Claims, 56 Drawing Sheets

(56) References Cited

U.S. PATENT DOCUMENTS

| | | | |
|---|---|---|---|
| 8,140,270 | B2 | 3/2012 | Kingsmore et al. |
| 8,392,353 | B2 | 3/2013 | Cho et al. |
| 8,417,459 | B2 | 4/2013 | Reese et al. |
| 8,489,334 | B2 | 7/2013 | Chen et al. |
| 2002/0160950 | A1 | 10/2002 | Lal et al. |
| 2003/0044864 | A1 | 3/2003 | Short et al. |
| 2003/0100995 | A1 | 5/2003 | Loraine et al. |
| 2003/0190649 | A1 | 10/2003 | Aerts et al. |
| 2004/0101876 | A1 | 5/2004 | Mintz et al. |
| 2004/0161779 | A1 | 8/2004 | Gingeras et al. |
| 2005/0032095 | A1 | 2/2005 | Wigler et al. |
| 2005/0214811 | A1 | 9/2005 | Margulies et al. |
| 2006/0142949 | A1 | 6/2006 | Helt et al. |
| 2006/0195428 | A1 | 8/2006 | Peckover et al. |
| 2007/0042380 | A1 | 2/2007 | Bentwich et al. |
| 2008/0243551 | A1 | 10/2008 | Subramaniam |
| 2009/0083268 | A1 | 3/2009 | Coqueret et al. |
| 2009/0182513 | A1 | 7/2009 | Draghici |
| 2009/0252046 | A1 | 10/2009 | Canright et al. |
| 2009/0299640 | A1 | 12/2009 | Ellis et al. |
| 2009/0307181 | A1 | 12/2009 | Colby et al. |
| 2010/0223261 | A1* | 9/2010 | Sarkar ............... G06F 17/30705 707/726 |
| 2010/0266588 | A1* | 10/2010 | Ko ....................... C12Q 1/6886 424/133.1 |
| 2010/0291681 | A1 | 11/2010 | Khvorova et al. |
| 2010/0318528 | A1 | 12/2010 | Kuperschmidt et al. |
| 2011/0060532 | A1 | 3/2011 | Gladding et al. |
| 2011/0098193 | A1* | 4/2011 | Kingsmore .......... C12Q 1/6869 506/9 |
| 2011/0183924 | A1* | 7/2011 | Mintz ..................... G06F 19/24 514/21.8 |
| 2011/0230365 | A1* | 9/2011 | Rohlfs ................. C12Q 1/6816 506/9 |
| 2012/0077682 | A1 | 3/2012 | Bowcock et al. |
| 2012/0078901 | A1 | 3/2012 | Conde et al. |
| 2012/0102041 | A1 | 4/2012 | Park et al. |
| 2012/0102054 | A1 | 4/2012 | Popescu et al. |
| 2012/0191366 | A1 | 7/2012 | Pearson et al. |
| 2012/0214159 | A1 | 8/2012 | George et al. |
| 2012/0214163 | A1 | 8/2012 | Sugarbaker et al. |
| 2012/0230326 | A1 | 9/2012 | Ganeshalingam et al. |
| 2013/0091126 | A1 | 4/2013 | Krishnaswami et al. |
| 2013/0311106 | A1 | 11/2013 | White et al. |
| 2014/0121116 | A1 | 5/2014 | Richards et al. |
| 2014/0121120 | A1 | 5/2014 | Chen et al. |
| 2014/0280327 | A1 | 9/2014 | Pham et al. |
| 2014/0310215 | A1 | 10/2014 | Trakadis |
| 2014/0359422 | A1 | 12/2014 | Bassett et al. |
| 2015/0154354 | A1 | 6/2015 | Torkamani et al. |

FOREIGN PATENT DOCUMENTS

| | | |
|---|---|---|
| WO | WO 2007/016668 A2 | 2/2007 |
| WO | WO 2009/058383 A2 | 5/2009 |
| WO | WO 2009/127693 A1 | 10/2009 |
| WO | WO 2012/029080 A1 | 3/2012 |
| WO | WO 2012/034030 A1 | 3/2012 |
| WO | WO 2012/098515 A1 | 7/2012 |
| WO | WO 2012/104764 A2 | 8/2012 |
| WO | WO 2013/009890 A2 | 1/2013 |
| WO | WO 2013/019987 A1 | 2/2013 |
| WO | WO 2013/049702 A2 | 4/2013 |
| WO | WO 2013/067001 A1 | 5/2013 |
| WO | WO 2013/070634 A1 | 5/2013 |
| WO | WO 2014/149972 A1 | 9/2014 |
| WO | WO 2014/151088 A2 | 9/2014 |

OTHER PUBLICATIONS

Karchin et al., LS-SNP: large-scale annotation of coding non-synonymous SNPs based on multiple information sources, 21(12): 2814-2820 (2005) doi: 10.1093/bioinformatics/bti442.

Karchin, Next generation tools for the annotation of human SNPs, Brief Bioinform (2009) 10 (1): 35-52.

Lee et al., F-SNP: computationally predicted functional SNPs for disease association studies, Nucl. Acids Res. (2007) 36 (suppl 1): D820-D824.

Yuan et al., FASTSNP: an always up-to-date and extendable service for SNP function analysis and prioritization, Nucl. Acids Res. (2006) 34 (suppl 2): W635-W641.

Specification, Claims, Abstract and Figures from U.S. Appl. No. 61/545,895, filed Oct. 11, 2011 (Priority application of U.S. Appl. No. 13/648,999, Krishnaswami et al.).

Specification, Claims, Abstract and Figures from U.S. Appl. No. 61/545,922, filed Oct. 11, 2011 (Priority application of U.S. Appl. No. 13/648,999, Krishnaswami et al.).

Specification, Claims, Abstract and Figures from U.S. Appl. No. 61/598,499, filed Feb. 14, 2012 (Priority application of U.S. Appl. No. 13/648,999, Krishnaswami et al.).

Specification, Claims, Abstract and Figures from U.S. Appl. No. 61/5640,389, filed Apr. 30, 2012 (Priority application of U.S. Appl. No. 13/648,999, Krishnaswami et al.).

Iordanov, Borislav, HyperGraphDB: A Generalized Graph Database, Web-Age Information Management: WAIM 2010 International Workshops, LNCS 6185 (2010) 25-36.

Ashley et al., Clinical evaluation incorporating a personal genome, Lancet (May 2010) 375(9725): 1525-1535. doi:10.1016/S0140-6736(10)60452-7.

Bansal et al., Statistical analysis strategies for association studies involving rare variants, Nat Rev Genet. (Nov. 2010) 11: 773-785.

ClinVar Overview, Nationial Society of Genetic Counselors, www.ncbi.nlm.nih.gov/clinvar/—(Downloaded Jul. 2014).

Dering et al., Statistical analysis of rare sequence variants: an overview of collapsing methods, Genet Epidemiol. (2011) 35(suppl 1): S12-S17.

Emily et al., Using biological networks to search for interacting loci in genome-wide association studies, Eur J Hum Genet (2009) 17(10): 1231-40, supplemental data.

Haggerty et al., A strategy for identifying transcription factor binding sites reveals two classes of genomic c-Myc target sites, Proc Acad Sci USA (2003) 100(9): 5313-5318.

International Search Report and Written Opinion for Application No. PCT/US2012/62787, mailed Jan. 28, 2013.

International Search Report and Written Opinion for Application No. PCT/US2014/021681, mailed May 23, 2014.

Kim et al., CNVRuler: A copy number variation-based case-control association analysis tool, Bioinformatics (2012) 28(13).

Kircher et al., A general framework for estimating the relative pathogenicity of human genetic variants, Nat Genet. (2004) 46(3): 310-315.

Korodi et al., A universal algorithm for random-access compression and applications for annotated DNA sequences, Conference: Genomic Signal Processing and Statistics, 2007. GENSIPS 2007.

Li et al., Methods for detecting associations with rare variants for common diseases: application to analysis of sequence data, Am. J. Human Genetics (2008) 83: 311-321, supplemental data.

Mooney, Bioinformatics approaches and resources for single nucleotide polymorphism functional analysis, Brief Bioinform (2005) 6(1): 44-56.

Mossé et al., Identification of ALK as the major familial neuroblastoma predisposition gene, Nature (2008) 455(7215): 930-935. doi: 10.1038/nature07261.

O'Connor et al., SeqWare Query Engine: storing and searching sequence data in the cloud, BMC Bioinformatics (2010) 11(Suppl 12):S2.

Shetty et al., SeqAnt: A web service to rapidly identify and annotate DNA sequence variations, BMC Bioinformatics (2010) 11:471.

Torkamani et al., Accurate prediction of deleterious protein kinase polymorphisms, Bioinformatics (2007) 23(21): 2918-2925.

Torkamani et al., Clinical implications of human population differences in genome-wide rates of functional genotypes, Front Genet. (2012) 3(211): 1-19.

Torkamani et al., Identification of rare cancer driver mutations by network reconstruction, Genome Res. (2009) 19: 1570-1578.

(56) References Cited

OTHER PUBLICATIONS

Torkamani et al., Predicting functional regulatory polymorphisms, Bioinformatics (2008) 24(16): 178701792.

Torkamani et al., Prediction of Cancer Driver Mutations in Protein Kinases, Cancer Res (2008) 68(6): 1675-1682.

Torkamani et al., Prestige centrality-based functional outlier detection in gene expression analysis, Bioinformatics (2009) 25(17): 2222-2228.

Tute Genomics—Product Homepage, www.tutegenomics.com/product (Downloaded Jul. 2014).

Tute Genomics—Annotations included in the Tute Genomics Web Platform www.tutegenomics.com (Downloaded Jul. 2014).

Van Zeeland et al., Evidence for the role of EPHX2 gene variants in anorexia nervosa, Mol Psychiatry (2014) 19: 724-732.

Wang et al., ANNOVAR: functional annotation of genetic variants from high-throughput sequencing data, Nucl Acids Res. (2010) 38(16): e164. doi: 10.1093/nar/gkq603.

Yandell et al., A probabilistic disease-gene finder for personal genomes, Genome Res. (2011) 21(9): 1529-1542.

Zeller et al., An integrated database of genes responsive to the Myc oncogenic transcription factor: identification of direct genomic targets, Genome Biology (2003) 4:R69.

Zhang et al., A general framework for weighted gene co-expression network analysis, Stat Appl Genet Mol Biol. (2005) 4:Article 17. Epub Aug. 12, 2005.

Zhao et al., CNVannotator: A comprehensive annotation server for copy number variation in the human genome, PLoS ONE (2013). doi: 10.1371/journal.pone.0080170.

ACMG, Standards and Guidelines for Clinical Genetics Laboratories; 2006 edition; pp. 1-33.

Richards et al., ACMG recommendations for standards for interpretation and reporting of sequence variations, 2007, Molecular Working Group of the ACMG Quality Committee, pp. 1-6.

Extended European Search Report received in EP Application No. 12845013.7, mailed Nov. 15, 2015.

\* cited by examiner

Four Major Levels of Annotation

| Genomic Elements |
|---|
| Known Genes |
| Protein Domains |
| Transcription Factor Binding Sites |
| Conserved Elements |
| miRNA Binding Sites |
| Splice Sites |
| Splicing Enhancers/Silencers |
| Common SNPs |
| UTR Regulatory Motifs |
| Post Translational Modification Sites |
| Custom Elements |

| Prediction of Impact |
|---|
| Coding Impact |
| Nosynonymous Impact Prediction |
| Protein Domain Impact Prediction |
| Motif Based Impact Scores |
| Nucleotide Conservation |
| TargetScan |
| Splicing Changes |
| Binding Energy |
| Codon Abundance |

| Linking Elements |
|---|
| Phase Information |
| Molecular Function |
| Biological Processes |
| Protein-Protein Interactions |
| Co-Expression |
| Genomic Context |

| Prior Knowledge |
|---|
| Phenotype Associations |
| Biological Processes |
| Molecular Function |
| Drug Metabolism |
| GWAS Catalog |
| Allele Frequency |
| eQTL Databases |
| Text Mining |

FIG. 4

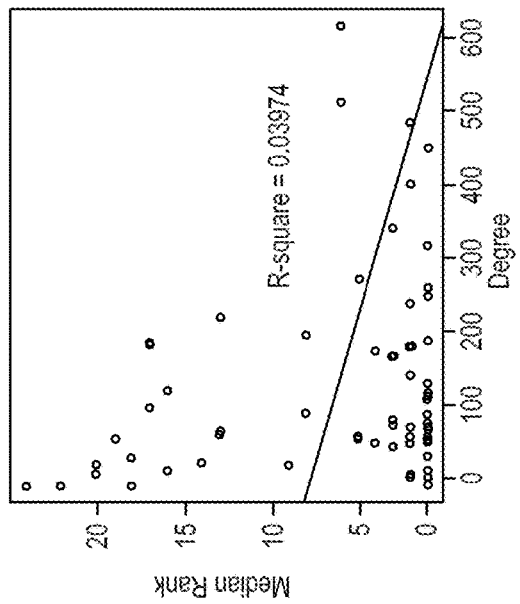
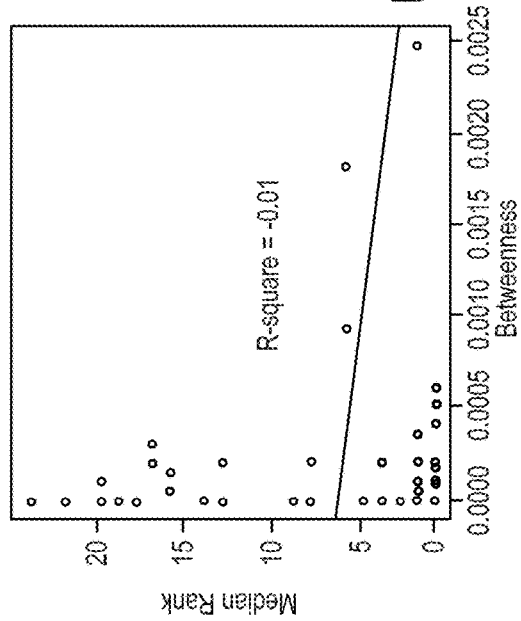
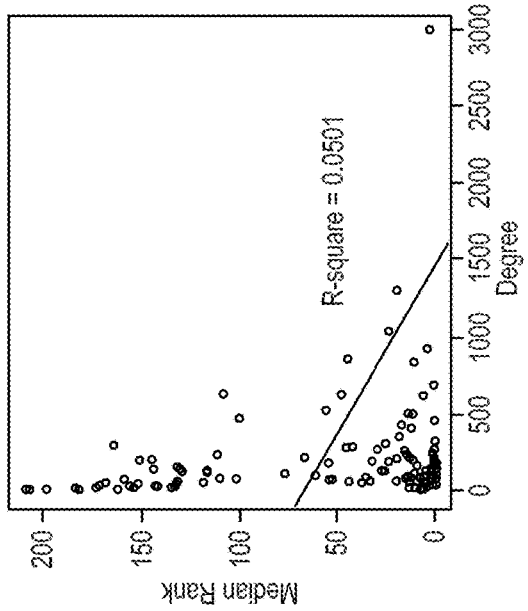
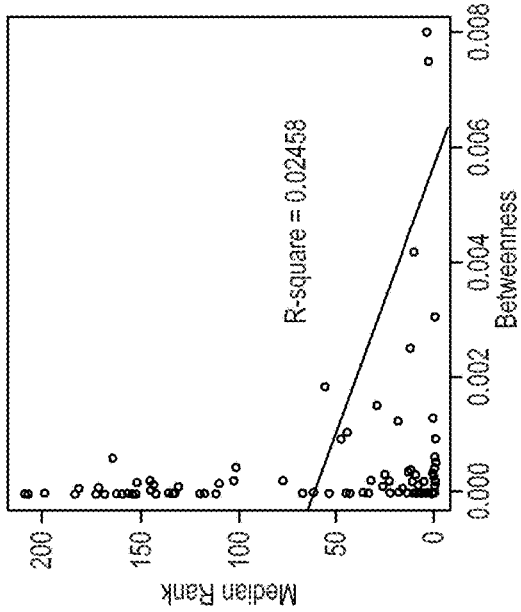
FIG. 11A
FIG. 11B
FIG. 11C
FIG. 11D

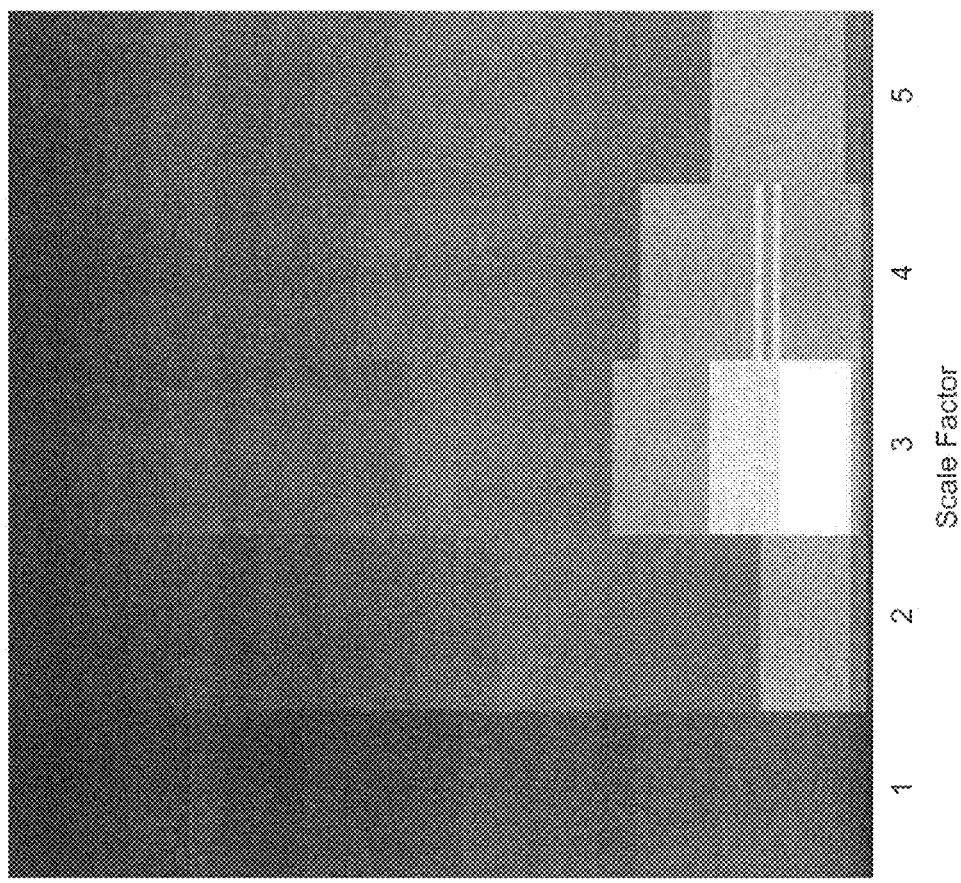
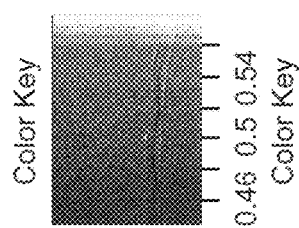
FIG. 14

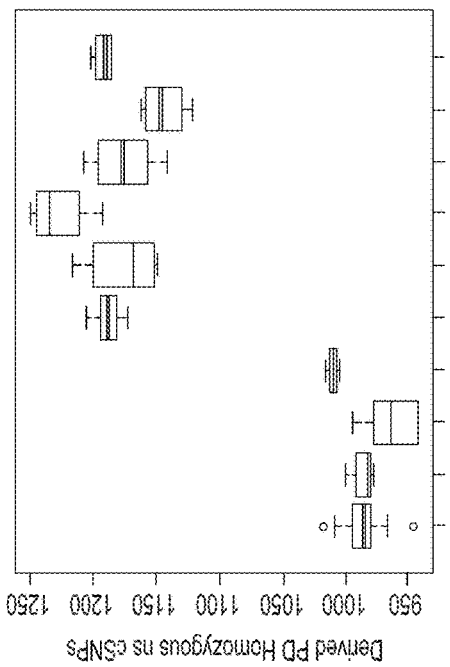
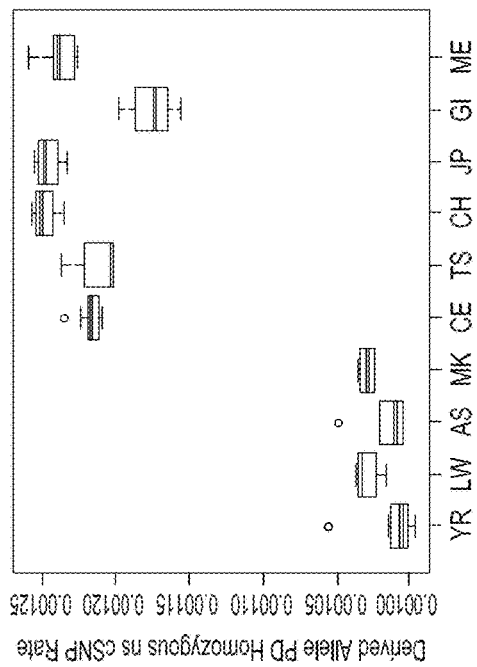
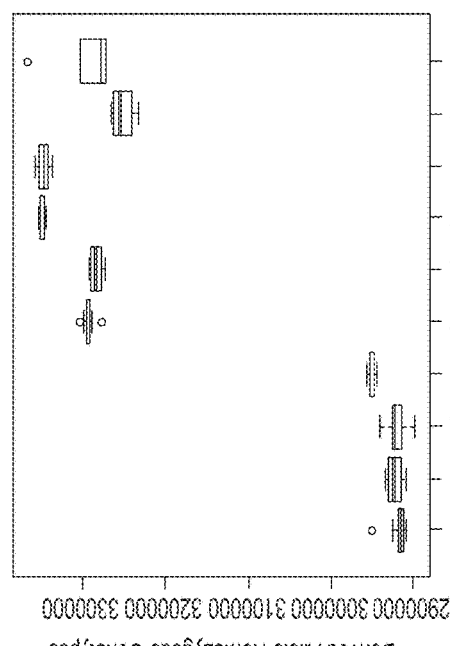
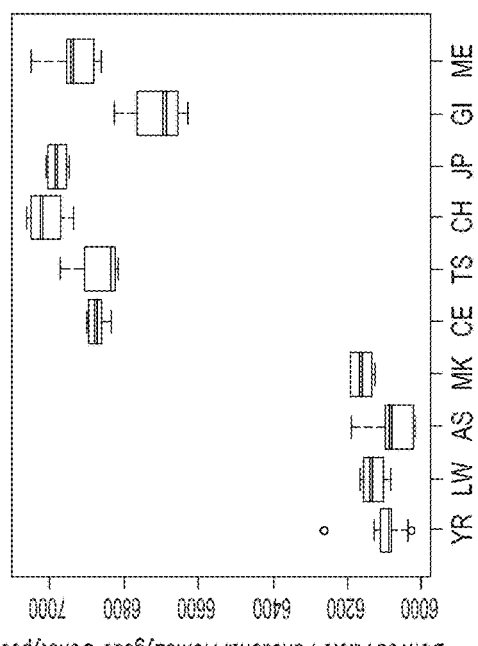

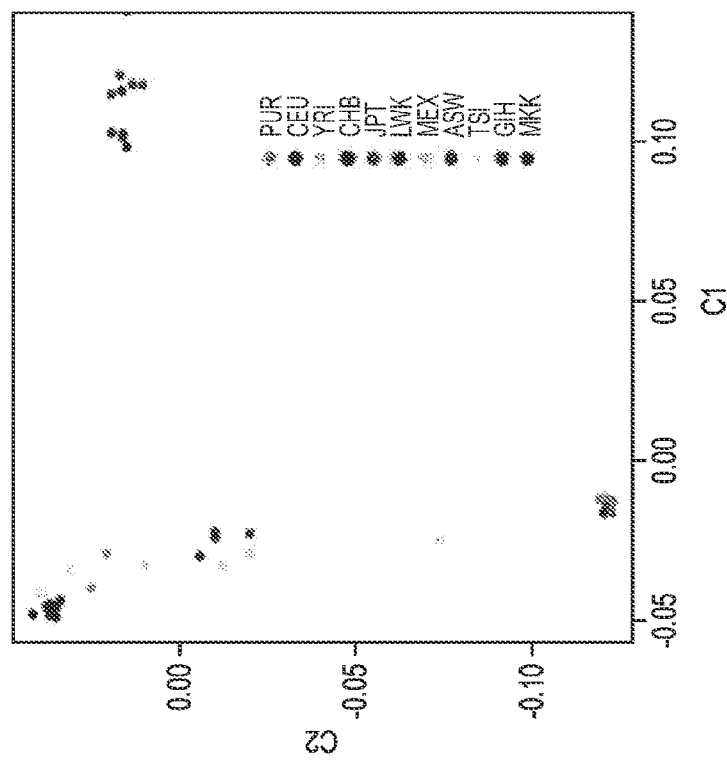
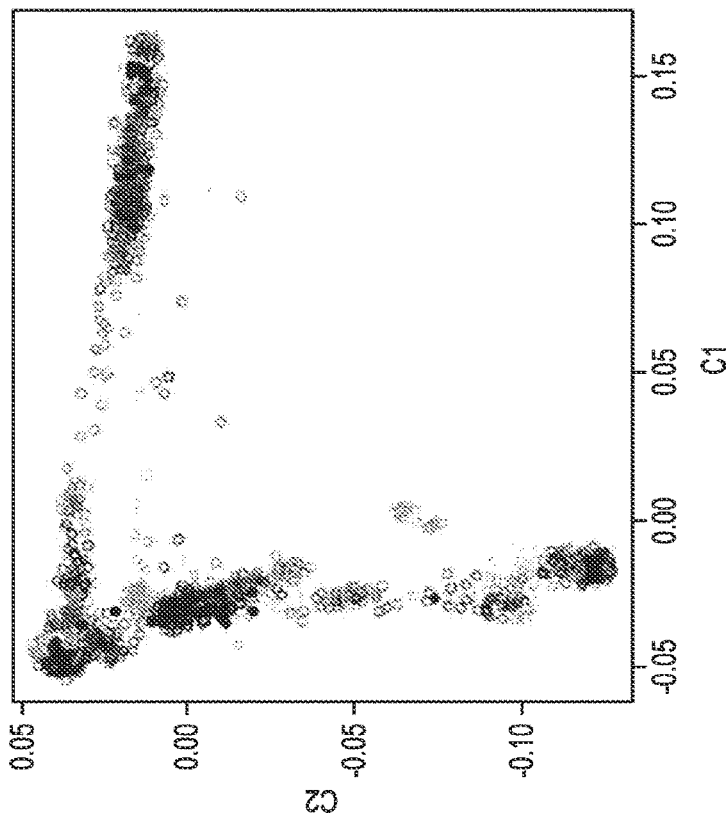
FIG. 18A
FIG. 18B

TABLE 1

| | Y-int | Africa | | | Europe | | Asia | | India | Mexico | R-Sqr |
|---|---|---|---|---|---|---|---|---|---|---|---|
| | | LW | AS | MK | CE | TS | CH | JP | GI | ME | |
| Total Derived Genotypes | 6042271.00 | -83419.25 | -57488.00 | -51149.25 | -395516.33 | -375283.25 | -428364.00 | -442378.00 | -332701.50 | -444921.80 | 0.97 |
| Nonsense SNPs: | 117.11 | 7.14 | 3.09 | -4.86 | -12.44 | -11.61 | -10.36 | -12.11 | -12.61 | -5.11 | 0.45 |
| Frameshift Structural Variants: | 450.11 | -7.86 | -3.51 | -15.36 | -64.56 | -36.11 | -35.36 | -37.61 | -21.36 | -55.11 | 0.71 |
| Splicing Change Variants: | 3009.33 | -17.08 | 17.47 | 9.42 | 4.33 | 14.92 | -34.08 | -48.58 | -5.08 | 2.07 | 0.29 |
| Probably Damaging ncsSNPs: | 2842.67 | 15.83 | 9.13 | -42.92 | -197.89 | -168.92 | -198.67 | -213.17 | -177.42 | -208.67 | 0.90 |
| Possibly Damaging ncsSNPs: | 2201.44 | 17.31 | 11.56 | -13.19 | -148.00 | -120.94 | -150.19 | -139.69 | -143.19 | -133.84 | 0.82 |
| Protein motif damaging Variants: | 1012.22 | -16.72 | -21.02 | -17.72 | -111.44 | -82.22 | -89.47 | -109.72 | -69.47 | -108.22 | 0.76 |
| TFBS Disrupting Variants: | 625.67 | -92.67 | -65.67 | -39.42 | -122.56 | -117.67 | -74.17 | -80.67 | -56.42 | -155.67 | 0.75 |
| miRNA-BS Disrupting Variants: | 215.78 | -7.28 | -10.78 | -15.78 | -51.00 | -42.53 | -49.78 | -51.78 | -41.03 | -66.58 | 0.91 |
| ESE-BS Disrupting Variants: | 2912.00 | -33.25 | -6.80 | -35.75 | -141.89 | -138.50 | -187.75 | -163.25 | -134.25 | -140.00 | 0.82 |
| ESS-BS Disrupting Variants: | 1225.56 | -17.31 | -1.36 | 15.19 | -43.56 | -40.31 | -54.06 | -71.56 | -40.31 | -84.56 | 0.72 |
| Total Likely Functional Variants: | 12983.11 | -148.11 | -71.31 | -133.11 | -730.11 | -599.61 | -729.61 | -734.86 | -557.86 | -783.11 | 0.90 |
| Functional Variants/Total Variants x 100000 | 214.87 | 0.53 | 0.86 | -0.38 | 2.12 | 3.65 | 3.40 | 3.86 | 2.75 | 3.09 | 0.57 |
| Total number of novel variants: | 2306608.44 | 19681.56 | -16356.84 | -26810.44 | -133947.00 | -122674.44 | -110435.44 | -113591.94 | -98801.19 | -125688.44 | 0.92 |
| Total Likely Functional Novel Variants: | 798.78 | 66.22 | -22.18 | -125.03 | -360.56 | -290.78 | -251.03 | -263.78 | -250.03 | -331.78 | 0.84 |
| Total number of homozygous genotypes: | 2919451.44 | 2748.06 | 680.16 | 30050.56 | 371821.44 | 362882.06 | 429429.81 | 426953.06 | 331099.31 | 377807.36 | 0.99 |
| Probably Damaging hmz ncsSNPs: | 985.00 | 0.75 | -20.80 | 25.75 | 202.78 | 191.00 | 243.75 | 191.75 | 160.00 | 207.60 | 0.97 |
| Prob Dam hmz ncsSNPs/Total Vars x 100000 | 16.30 | 0.24 | -0.19 | 0.57 | 4.73 | 4.45 | 5.58 | 4.71 | 3.75 | 5.00 | 0.98 |
| Total Likely Functional Homozygous Variants: | 6103.11 | 30.39 | -19.71 | 62.14 | 772.00 | 762.39 | 907.39 | 877.89 | 606.14 | 835.09 | 0.98 |
| Likely functional hmz vars/Total Vars x 100000 | 101.02 | 1.91 | 0.64 | 1.89 | 20.74 | 20.14 | 23.86 | 23.65 | 16.49 | 22.94 | 0.99 |

FIG. 21

TABLE 2

| Sample | YR | LW | AS | MK | CE | TS | CH | JP | GI | ME |
|---|---|---|---|---|---|---|---|---|---|---|
| YR |  | -30 | 20 | -62 | -772 | -762 | -907 | -878 | -606 | -835 |
| LW | -83419 |  | 50 | -32 | -742 | -732 | -877 | -848 | -576 | -805 |
| AS | -57488 | 25931 |  | -82 | -792 | -782 | -927 | -898 | -626 | -855 |
| MK | -51149 | 32270 | 6339 |  | -710 | -700 | -845 | -816 | -544 | -773 |
| CE | -395516 | -312097 | -338028 | -344367 |  | 10 | -135 | -106 | 166 | -63 |
| TS | -375283 | -291864 | -317795 | -324134 | 20233 |  | -145 | -116 | 156 | -73 |
| CH | -428364 | -344945 | -370876 | -377215 | -32848 | -53081 |  | 30 | 301 | 72 |
| JP | -442378 | -358959 | -384890 | -391229 | -46862 | -67095 | -14014 |  | 272 | 43 |
| GI | -332702 | -249282 | -275214 | -281552 | 62815 | 42582 | 95663 | 109677 |  | -229 |
| ME | -444922 | -361503 | -387434 | -393773 | -49405 | -69639 | -16558 | -2544 | -112220 |  |

FIG. 22

TABLE 3

| Variant Type | | Populations | | | z-test p-values | | |
|---|---|---|---|---|---|---|---|
| Variant Type | Label | AFR | EUR | ASN | AFR vs EUR | AFR vs ASN | EUR vs ASN |
| Total number of variants: | | 7614850 | 2024886 | 1294731 | | | |
| Nonsense SNPs rate | 1 | 0.500 | 0.840 | 0.842 | 6.931E-09 | 6.329E-07 | 4.910E-01 |
| Frameshift Structural Variants rate | 2 | 1.663 | 3.008 | 2.989 | 1.597E-34 | 6.239E-25 | 4.621E-01 |
| Frameshift Insertion rate | 3 | 0.657 | 1.274 | 1.383 | 6.368E-19 | 1.089E-18 | 2.006E-01 |
| Frameshift Deletion rate | 4 | 0.879 | 1.417 | 1.352 | 3.877E-12 | 1.584E-07 | 3.102E-01 |
| Frameshift Rearrangement rate | 5 | 0.127 | 0.316 | 0.255 | 2.614E-09 | 2.228E-04 | 1.572E-01 |
| Splicing Change Variants rate | 6 | 1.707 | 2.514 | 2.379 | 4.655E-14 | 7.112E-08 | 2.223E-01 |
| Probably Damaging nscSNPs rate | 7 | 10.103 | 15.472 | 15.602 | 1.136E-91 | 4.578E-69 | 3.853E-01 |
| Possibly Damaging nscSNPs rate | 8 | 5.991 | 7.744 | 8.233 | 7.313E-19 | 3.064E-21 | 6.111E-02 |
| Protein motif damaging Variants rate | 9 | 4.104 | 6.311 | 6.581 | 2.612E-39 | 3.043E-35 | 1.726E-01 |
| TFBS Disrupting Variants rate | 10 | 2.793 | 4.173 | 4.063 | 7.493E-69 | 2.764E-42 | 1.785E-01 |
| miRNA-BS Disrupting Variants rate | 11 | 0.948 | 1.170 | 1.081 | 2.405E-03 | 7.715E-02 | 2.286E-01 |
| ESE-BS Disrupting Variants rate | 12 | 5.835 | 7.260 | 7.283 | 1.696E-13 | 2.840E-10 | 4.689E-01 |
| ESS-BS Disrupting Variants rate | 13 | 2.460 | 3.013 | 2.865 | 6.435E-06 | 3.539E-03 | 2.232E-01 |
| Total Likely Functional Variant rate | 14 | 23.718 | 34.906 | 35.436 | 8.999E-170 | 1.234E-132 | 2.128E-01 |

FIG. 23

TABLE 4

| | | | | | PolyPhen Score > 0.825 (N=506) | | | | | |
|---|---|---|---|---|---|---|---|---|---|---|
| Indiv | Source | ALLDB | All 1000k | 1000k EUR | 1000k ASN | 1000k AFR | All CGI | CGI EUR | CGI ASN | CGI AFR |
| | | | 1000+ | ~500 | ~500 | ~500 | 52 | 8 | 8 | 8 |
| EUROPEAN | STSI | 101/1593 | 179/1593 | 194/1593 | 317/1593 | 680/1593 | 174/1593 | 439/1593 | 588/1593 | 669/1593 |
| AFRICAN AMERICAN | CGI | | 185/1983 | 262/1938 | 795/1938 | 1068/1938 | | 991/1938 | 995/1938 | 568/1938 |
| MEXICAN | CGI | | 169/1595 | 272/1595 | 362/1595 | 676/1595 | | 491/1595 | 566/1595 | 681/1595 |
| EAST INDIAN | CGI | | 257/1685 | 329/1685 | 405/1685 | 669/1685 | | 533/1685 | 538/1685 | 680/1685 |
| PUERTA RICAN | CGI | | 220/1664 | 287/1664 | 417/1664 | 683/1664 | | 491/1664 | 576/1664 | 654/1664 |

| | | | | | SIFT Score > 0.931 (N=506) | | | | | |
|---|---|---|---|---|---|---|---|---|---|---|
| Indiv | Source | ALLDB | All 1000k | 1000k EUR | 1000k ASN | 1000k AFR | All CGI | CGI EUR | CGI ASN | CGI AFR |
| | | | n=1000+ | ~500 | ~500 | ~500 | 52 | 8 | 8 | 8 |
| EUROPEAN | STSI | 127/2593 | 232/2593 | 252/2593 | 394/2593 | 947/2593 | 221/2593 | 627/2593 | 843/2593 | 930/2593 |
| AFRICAN AMERICAN | CGI | | 241/3199 | 319/3199 | 1174/3199 | 1662/3199 | | 1557/3199 | 1569/3199 | 828/3199 |
| MEXICAN | CGI | | 221/2565 | 311/2565 | 449/2565 | 963/2565 | | 689/2565 | 831/2565 | 948/2565 |
| EAST INDIAN | CGI | | 353/2856 | 433/2856 | 537/2856 | 1070/2856 | | 803/2856 | 835/2856 | 1016/2856 |
| PUERTA RICAN | CGI | | 289/2657 | 351/2657 | 502/2657 | 963/2657 | | 676/2657 | 809/2657 | 900/2657 |

| | | | | | Average Score > 0.878 (N=506) | | | | | |
|---|---|---|---|---|---|---|---|---|---|---|
| Indiv | Source | ALLDB | All 1000k | 1000k EUR | 1000k ASN | 1000k AFR | All CGI | CGI EUR | CGI ASN | CGI AFR |
| | | | n=1000+ | ~500 | ~500 | ~500 | 52 | 8 | 8 | 8 |
| EUROPEAN | STSI | 90/1269 | 157/1269 | 169/1269 | 268/1269 | 563/1269 | 146/1269 | 362/1269 | 478/1269 | 551/1269 |
| AFRICAN AMERICAN | CGI | | 148/1524 | 197/1524 | 628/1524 | 871/1524 | | 800/1524 | 802/1524 | 466/1524 |
| MEXICAN | CGI | | 145/1229 | 204/1229 | 279/1229 | 556/1229 | | 396/1229 | 455/1229 | 565/1229 |
| EAST INDIAN | CGI | | 213/1321 | 255/1321 | 315/1321 | 562/1321 | | 428/1321 | 429/1321 | 556/1321 |
| PUERTA RICAN | CGI | | 173/1281 | 208/1281 | 309/1281 | 546/1281 | | 391/1281 | 461/1281 | 531/1281 |

FIG. 24

TABLE 5

| Mutation Type (chrom_begpos_endpos_type_ref_alt) | Disease | Disease Gene |
|---|---|---|
| chr1_112124857_112124858_snp_G_A | brugada syndrome | KCND3 |
| chr1_158516485_158516486_snp_G_A | zellweger syndrome, complementation group j | PEX19 |
| chr1_158593068_158593069_snp_T_G | acne inversa, familial | NCSTN |
| chr1_208395839_208395840_snp_G_A | spinocerebellar ataxia with psychomotor retardation | SYT14 |
| chr1_218450768_218450777_del_AGTGTAGAA_ | warbug micro syndrome | RAB3GAP2 |
| chr1_26637305_26637306_snp_A_G | retinitis pigmentosa, autosomal recessive | DHDDS |
| chr10_104346976_104346976_ins_-_C | medulloblastoma, desmoplastic | SUFU |
| chr10_104668343_104668344_del_G_- | hypomagnesemia | CNNM2 |
| chr10_27742261_27742261_ins_-_C | potential protein deficiency | PTCHD3 |
| chr10_27838811_27838812_snp_T-A | warburg micro syndrome | RAB18 |
| chr10_93379871_93379872_snp_T_C | myoclonic epilepsy of larora | PPP1R3C |
| chr11_124299101_124299102_snp_G_A | megalencephalic leukoencephalophathy with subcortical systs | HEPACAM |
| chr11_47263205_47263206_sno_C_T | potential protein deficiency | MADD |
| chr11_603207_603208_snp_T_C | systemic lupus erythematosus, association with | IRF7 |
| chr11_62140632_62140633_snp_C_T | larsen-like syndrome, b3gat3 type | B3GAT3 |
| chr11_65527330_65527331_snp_G_A | progeroid syndrome | BANF1 |
| chr11_95185781_95185782_snp_C_T | mosaic variegated aneuploidy | CEP57 |
| chr12_104078051_104078052_snp_C_G | intellectual disability, nonsyndromic | KIAA1033 |
| chr12_121267307_121267308_snp_G_A | progressive hearing loss | DIABLO |
| chr12_44068264_44068264_ins_-_T | scott syndrome | ANO6 |
| chr12_64008630_64008631_snp_T_G | deafness, non-syndromic, autosomol recessive | MSRB3 |
| chr12_65072437_65072438_snp_A_C | autism | GRIP1 |
| chr13_26726383_26726384_snp_G_A | hypotrichosis simplex | RPL21 |
| chr14_101516595_101516596_snp_A_G | charcot-marie-tooth disease, axonol | DYNC1H1 |
| chr14_30605276_30605277_snp_C_T | intellectual disability, spastic paraplegia & short stature | AP4S1 |
| chr14_64630252_64630253_snp_G_A | pheochromocytoma | MAX |
| chr14_69547276_69547277_snp_C_T | microphthalmia with limb anomalies | SMOC1 |
| chr14_69547406_69547407_snp_C_A | waardenburg anophthalmia syndrome | SMOC1 |
| chr14_73225887_73225888_snp_A_G | primary ciliary dyskinesia | DNAL1 |
| chr14_73494604_73494605_snp_C_T | nephrotic syndrome | COQ6 |
| chr14_73494684_73494685_snp_G_A | diffuse mesangial sclerosis | COQ6 |
| chr14_73498322_73498323_snp_G_A | nephrotic syndrome with sensorineural deafness | COQ6 |

FIG. 25A

| Mutation Type (chrom_begpos_endpos_type_ref_alt) | Disease | Disease Gene |
|---|---|---|
| chr14_88108702_88108703_snp_C_T | intellectual disability, nonsyndromic, autosomal recessive | ZC3H14 |
| chr15_43682596_43682597_snp_C_T | hermansky-pudlak syndrome 9 | PLDN |
| chr15_57253695_57253696_snp_A_C | focal segmental glomerulosclerosis, childhood familial | MYO1E |
| chr15_8792688_87972700_del_GGCTGGCTCGTC_- | joubert syndrome | KIF7 |
| chr15_87993444_87993445_del_C_- | acrocallosal syndrome | KIF7 |
| chr16_45283855_45283857_del_TT_- | meier-gorlin syndrome | ORC6 |
| chr16_84500159_84500160_snp_A_G | immunodeficiency, autosomol dominant | IRF8 |
| chr16_84500243_84500244_snp_A_G | immunodeficiency, autosomol recessive | IRF8 |
| chr16_87400541_87400542_snp_C_T | meier-gorlin syndrome | CDT1 |
| chr17_36832584_36832585_snp_G_A | potential protein deficiency | KRT37 |
| chr17_36849009_36849010_snp_G_A | potential protein deficiency | KRT38 |
| chr17_37226933_37226934_snp_G_A | osteogenesis imperfecta, autosomal recessive | FKBP10 |
| chr17_37229003_37229003_ins_-_C | osteogenesis imperfecta/bruck syndrome | FKBP10 |
| chr17_64063477_64063478_snp_G_A | amelogenesis imperfecta & gingival hyperplasia syndrome | FAM20A |
| chr17_7258521_7258522_snp_G_A | schizophrenia | NLGN2 |
| chr17_8133101_8133102_snp_G_T | altered function, association with | RANGRF |
| chr17_8133354_8133355_snp_G_C | brugada syndrome | RANGRF |
| chr18_3073802_3073803_snp_C_T | cardiomyopathy, hypertrophic | MYOM1 |
| chr18_42358694_42358695_snp_G_A | hearing loss, non-syndromic, autosomal recessive | LOXHD1 |
| chr18_42936561_42936562_snp_A_G | microcephaly with simplified gyration, epilepsy & diabetes | IER3IP1 |
| chr19_10126692_10126693_snp_T_C | sensory neuropathy with dementia & hearing loss | DNMT1 |
| chr19_19190923_19190924_snp_C_T | nonalcoholic fatty liver disease, increased risk, assoc. with | NCAN |
| chr19_3541151_3541152_snp_G_A | sensorineural hearing loss | GIPC3 |
| chr19_38209354_38209355_snp_C_T | colorectal cancer, increased risk, association with | RHPN2 |
| chr19_4106005_4106006_snp_G_A | hypertriglyceridaemia | CREB3L3 |
| chr19_41283495_41283497_del_AG_- | polymicrogyria | WDR62 |
| chr19_44098785_44098786_snp_T_C | hyperuricemia, pulmonary hypertension, renal failure & alkalosis | SARS2 |
| chr19_6326504_6326505_snp_G_A | aganglionosis, in hirschsprung disease | PSPN |
| chr2_128742297_128742298_snp_G_A | hypogonadotropic hypogonadism, idopathic | HS6ST1 |
| chr2_128742473_128742474_snp_C_T | kallmann syndrome | HS6ST1 |
| chr2_166453185_166453186_snp_G_C | bardet-biedl syndrome | TTC21B |

FIG. 25B

| Mutation Type (chrom_begpos_endpos_type_ref_alt) | Disease | Disease Gene |
|---|---|---|
| chr2_166466635_166466636_snp_G_A | joubert syndrome | TTC21B |
| chr2_166472471_166472472_snp_T_C | meckel-gruber syndrome | TTC21B |
| chr2_166477333_166477334_snp_G_A | meckel-gruber like syndrome | TTC21B |
| chr2_166508078_166508079_snp_A_G | nephronophthisis | TTC21B |
| chr2_20009736_20009737_snp_G_A | short rib-polydactyly syndrome | WDR35 |
| chr2_210793700_210793701_snp_G_A | acyl-coa dehydrogenase, long chain deficiency | ACADL |
| chr2_238972266_238972267_del_G_- | potential protein deficiency | TRAF |
| chr2_240609321_240609322_snp_T_C | complex i deficiency | NDUFA10 |
| chr2_241371862_241371863_snp_G_A | spastic paraparesis | KIF1A |
| chr2_241376207_241376208_snp_G_A | intellectual disibility, nonsyndromic | KIF1A |
| chr2_3669376_3669377_snp_G_A | 3mc syndrome | COLEC11 |
| chr2_98587028_98587029_snp_C_G | hypertrophic cardiomyopathy, fatal neonatal | C2orf64 |
| chr20_34273652_34273653_snp_C_T | intellectual disibility, nonsyndromic | EPB41L1 |
| chr20_36380261_36380262_snp_G_A | inflammatory bowel disease, association with | BPI |
| chr20_3786399_3786400_snp_G_T | systemic lupus erythematosus, increased risk, association with | MAVS |
| chr20_57004154_57004155_snp_C_T | tuberculosis, susceptibility to, association with | CTSZ |
| chr20_62032669_62032670_snp_T_G | neuronal ceroid lipofuscinosis, adult-onset | DNAJC5 |
| chr20_62128934_62128935_snp_C_T | retinitis pigmentosa, autosomol dominant | PRPF6 |
| chr20_74313_74315_del_CC_- | impaired sperm function, association with | DEFB126 |
| chr21_9964626_9964627_snp_G_A | potential protein deficiency | TPTE |
| chr22_15965618_15965619_snp_C_T | mucocutaneous candidiasis | IL17RA |
| chr22_35292354_35292355_snp_C_G | intellectual disability, nonsyndromic | CACNG2 |
| chr22_49364533_49364534_snp_C_A | muscular dystrophy, mental retardation & enlarged mitochondria | CHKB |
| chr3_113671298_113671299_snp_T_G | rheumatoid arthritis, suspectibility, association | BTLA |
| chr3_143757429_143757430_del_T_- | seckel syndrome | ATR |
| chr3_188436464_188436465_snp_A_G | 3mc syndrome | MASP1 |
| chr3_45974947_45974948_del_G_- | congenital cataracts | FYCO1 |
| chr3_48240105_48240106_snp_G_A | periodontitis, generalized aggressive, assoc. with | CAMP |
| chr3_53817802_53817802_ins_-_C | potential protein deficiency | CACNA1D |
| chr3_71132859_71132859_ins_-_T | autism spectrum disorder | FOXP1 |
| chr4_166482396_166482397_snp_A_G | psoriasiform dermatitis, microcephaly & developmental delay | SC4MOL |
| chr4_170748468_170748469_snp_G_A | short rib-polydactyly syndrome, majewski type | NEK1 |
| chr4_70496630_70496631_snp_C_T | altered enzyme activity, association with | UGT2A1 |

FIG. 25C

| Mutation Type (chrom_begpos_endpos_type_ref_alt) | Disease | Disease Gene |
|---|---|---|
| chr4_79619805_79619806_del_G_- | fraser syndrome | FRAS1 |
| ch5_140057079_140057080_snp_G_T | perrault syndrome | HARS2 |
| chr6_109909089_109909090_snp_G_C | immunodeficiency, centromeric instability & facial anom. syndrome | ZBTB24 |
| chr6_143830991_143830995_del_ATAA_- | zellweger syndrome g | PEX3 |
| chr6_147677105_147677106_snp_A_G | venous thrombosis, reduced risk, association | STXBP5 |
| ch6_1700434487_170434490_del_TGT_- | holoprosencephaly, susceptibility to | DLL1 |
| chr6_33518983_33518984_del_C_- | intellectual disibility, nonsyndromic | SYNGAP1 |
| chr6_34320624_34320625_snp_G_T | diabetes mellitus, type 2 | HMGA1 |
| chr7_81437176_81437177_snp_C_G | short qt syndrome | CACNA2D1 |
| chr7_87751156_87751157_snp_C_T | metabolic syndrome, association with | STEAP4 |
| chr8_15524983_15524984_snp_C_T | mental retardation, non-syndromic, autosomal recessive | TUSC3 |
| chr8_37730198_37730198_ins_-_AC | intellectual disibility, motor dysfunction & joint contractures | ERLIN2 |
| chr8_58055150_58055151_snp_T_G | chonodrodysplasia & abnormal joint development | IMPAD1 |
| chr9_132904110_132904111_snp_A_G | autism spectrum disorder | LAMC3 |
| chr9_135019465_135019466_snp_G_T | potential protein deficiency | GBGT1 |
| chr9_139176982_139176983_snp_G_A | intellectual disability, nonsyndromic | GRIN1 |
| chr9_139469527_139469528_snp_C_T | kallmann syndrome | NELF |
| chr9_139470698_139470699_snp_G_C | gnrh deficiency | NELF |
| chrX_139414147_139414165_del_GGCGGCAGCGGCTGCGGC_- | hypopituitarism | SOX3 |
| chrX_151659500_151659501_snp_C_G | potential protein deficiency | CSAG1 |
| chrX_21665654_21665655_snp_C_A | progressive hearing impairment | SMPX |
| chrX_21665693_21665694_snp_C_A | x-chromosomal hearing loss | SMPX |

FIG. 25D

TABLE 6

| Mutation Type (chrom_begpos_endpos_type_ref_alt) | Disease | Disease Gene |
|---|---|---|
| chr1_158593068_158593069_snp_T_G | Acne inversa, familial | NCSTN |
| chr1_26390397_26390398_snp_A_G | Asthenozoospermia? | CATSPER4 |
| chr1_43445001_43445002_snp_G_T | Van der Woude syndrome? | WDR65 |
| chr10_104668343_104668344_del_G_- | Hypomagnesemia | CNNM2 |
| chr10_27742261_27742261_ins_-_C | Potential protein deficiency | PTCHD3 |
| chr10_93379871_93379872_snp_T_C | Myoclonic epilepsy of Lafora | PPP1R3C |
| chr11_124299101_124299102_snp_G_A | Megalencephalic leukoencephalopathy with subcortical cysts | HEPACAM |
| chr11_125359153_125359154_snp_T_G | Holoprosencephaly | CDON |
| chr11_47263205_47263206_snp_C_T | Potential protein deficiency | MADD |
| chr11_95185781_95185782_snp_C_T | Mosaic variegated aneuploidy | CEP57 |
| chr12_104078051_104078052_snp_C_G | Intellectual disability, nonsyndromic | KIAA1033 |
| chr2_44068264_44068264_ins_-_T | Scott syndrome | ANO6 |
| chr12_64008630_64008631_snp_T_G | Deafness, non-syndromic, autosomal recessive | MSRB3 |
| chr14_73225887_73225888_snp_A_G | Primary ciliary dyskinesia | DNAL1 |
| chr14_73494604_73494605_snp_C_T | Nephrotic syndrome | COQ6 |
| chr14_73494684_73494685_snp_G_A | Diffuse mesangial sclerosis | COQ6 |
| chr14_88108702_88108703_snp_C_T | Intellectual disability, nonsyndromic, autosomal recessive | ZC3H14 |
| chr15_57311227_57311228_snp_C_G | Nephrotic syndrome, steroid resistent? | MYO1E |
| chr15_87972688_87972700_del_GGCTGGCTCGTC_- | Joubert syndrome | KIF7 |
| chr15_87974637_87974638_snp_G_A | Bardet-Biedl syndrome? | KIF7 |
| chr15_87991212_87991214_delins_CC_A | Acrocallosal syndrome | KIF7 |
| chr16_45283855_45283857_del_TT_- | Meier-Gorlin syndrome | ORC6 |
| chr16_87400541_87400542_snp_C_T | Meir-Gorlin syndrome | CDT1 |
| chr17_36832584_36832585_snp_G_A | Potential protein deficiency | KRT37 |
| chr17_36849009_36849010_snp_G_A | Potential protein deficiency | KRT38 |

FIG. 26A

| Mutation Type (chrom_begpos_endpos_type_ref_alt) | Disease | Disease Gene |
|---|---|---|
| chr17_37226933_37226934_snp_G_A | Ostegenesis imperfecta, autosomal recessive | FKBP10 |
| chr17_7258521_7258522_snp_G_A | Schizophrenia | NLGN2 |
| chr17_78301705_78301706_snp_A_G | Diabetes mellitus, type 2 ? | FN3K |
| chr18_42358894_42358895_snp_G_A | Hearing loss, non-syndromic, autosomal recessive | LOXHD1 |
| chr19_3541151_3541152_snp_G_A | Sensorineural hearing loss | GIPC3 |
| chr19_4106005_4106006_snp_G_A | Hypertriglyceridaemia | CREB3L3 |
| chr19_41283495_41283497_del_AG_- | Polymicrogyria | WDR62 |
| chr19_6326504_6326505_snp_G-A | Aganglionosis, in Hirschsprung disease | PSPN |
| chr2_128742297_128742298_snp_G_A | Hypogonadotropic hypogonadism, idiopathic | HS6ST1 |
| chr2_128742525_128742526_snp_G_A | Kallmann syndrome | HS6ST1 |
| chr2_166453185_166453186_snp_G_C | Bardet_Biedl syndrome | TTC21B |
| chr2_166466635_166466636_snp_G_A | Joubert syndrome | TTC21B |
| chr2_166477333_166477334_snp_G_A | Meckel_Gruber-like syndrome | TTC21B |
| chr2_166494974_166494975_snp_T_C | Meckel_Gruber syndrome | TTC21B |
| chr2_166508078_166508079_snp_A_G | Nephronophthisis | TTC21B |
| chr2_20009736_20009737_snp_G_A | Short rib-polydactyly syndrome | WDR35 |
| chr2_238972266_238972267_del_G_- | Potential protein deficiency | TRAF3IP1 |
| chr2_240609321_240609322_snp_T_C | Complex I deficiency | NDUFA10 |
| chr2_241376207_241376208_snp_G_A | Intellectual disability, nonsyndromic | KIF1A |
| chr2_68736091_68736092_snp_A_T | Hirschsprung disease? | PROKR1 |
| chr20_34273652_34273653_snp_C_T | Intellectual disability, nonsyndromic | EPB41L1 |
| chr20_62128934_62128935_snp_C_T | Retinitis pigmentosa, autosomal dominant | PRPF6 |
| chr21_9964626_9964627_snp_G_A | Potential protein deficiency | TPTE |
| chr22_15965618_15965619_snp_C_T | Mucocutaneous candidiasis | IL17RA |
| chr22_35292354_35292355_snp_C_G | Intellectual disability, nonsyndromic | CANG2 |

FIG. 26B

| Mutation Type (chrom_begpos_endpos_type_ref_alt) | Disease | Disease Gene |
|---|---|---|
| chr3_143757429_143757430_del_T_- | Sekel syndrome | ATR |
| chr3_53817802_53817802_ins_-_C | Potential protein deficiency | CACNA1D |
| chr3_64118034_64118035_snp_C_T | Myoclonus epilepsy ? | PRICKLE2 |
| chr3_71132859_71132859_ins_-_T | Autism spectrum disorder | FOXP1 |
| chr4_170748468_170748469_snp_G_A | Short rib-polydactyly syndrome, Majewski type | NEK1 |
| chr4_79619805_79619806_del_G_- | Fraser syndrome | FRAS1 |
| chr5_140057079_140057080_snp_G_T | Perrault syndrome | HARS2 |
| chr6_335189833_33518984_del_C_- | Intellectual disability, nonsyndromic | SYNGAP1 |
| chr6_34320624_34320625_snp_G_T | Diabetes mellitus, type 2 | HMGA1 |
| chr7_129827822_129827823_snp_A_C | Autism spectrum disorder ? | TSGA14 |
| chr8_15524983_15524984_snp_C_T | Mental retardation, non-syndromic, autosomal recessive | TUSC3 |
| chr9_132904110_132904111_snp_A_G | Autism spectrum disorder | LAMC3 |
| chr9_135019465_135019466_snp_G_T | Potential protein dificiency | GBGT1 |
| chr9_16427344_16427345_snp_T_C | Hypospadias ? | BNC2 |
| chr9_5154042_5154043_snp_C_T | Spermatogenic failure ? | INSL6 |
| chrX_139414147_139414165_del_GGCGGGCAGCGGGCTGCGGC_- | Hypopituitarism | SOX3 |
| chrX_151659500_151659501_snp_C_G | Potential protein deficiency | CSAG1 |

FIG. 26C

TABLE 7

| Test Disease | Combined Entries of Diseases (Separated by "///") | Final List of Seeds |
|---|---|---|
| 3-m syndrome | 3-m syndrome | DKFZp761H229,CUL7,OBSL1 |
| acne inversa, familial | acne inversa, familial | PSENEN,PSEN1,LIN37 |
| acrocallosal syndrome | acrocallosal syndrome | GLI3 |
| acyl-coa dehydrogenase, long chain deficiency | acyl-coa dehydrogenation deficiency///acyl-coa-dehydrogenase deficiency | ACADS,ETFDH |
| aganglionosis, in hirschsprung disease | aganglionosis, in hirschsprung disease///aganglionosis, total colonic | RET,NRTN |
| altered enzyme activity, association with | altered enzyme activity, association with///enzyme activity, assoc. with///enzyme activity, association with///increased enzyme activity, association with///lower enzyme activity///reduced enzyme activity with daun, assoc with///reduced enzyme activity with dox/daun, assoc with///reduced enzyme activity, association with///reduced enzyme stability, association with | EPHX2,TOMM40L,CYP2B6,hOGG1,UGT2A3,UGT1A8, UGT1A9,UGT1A4,UGT1A5,AANAT,UGT1A7,UGT1A6, OGG1,UGT1A3,NR1I3,CHIA,UGT1A10,ASMT,CHIT1,P OR,AS3MT,MTHFR,UGT2B10,HSD17B2,AKR1C3,TXNR D2,DKFZp686G12235,WRN,SULT1A3,CYP2A7,MGMT, UNQ2559,PLA2G4A,TRXR2A,FTO,GSTO1,OGG1 type 1e,ARSA,OGG1 type 1f,NT5C3,PDE11A,GSTZ1,MASP2,PRODH,CBS,FLJ003 14,MME,ALDH5A1, NEU2 |
| altered function, association with | altered function///altered function, association with///impaired function, association with///reduced function///reduced function, association with | FAS,CD40LG,U80764,OCTN2,SLC5A1,BSND,CCR5,TST, P2RX7,UTF1,CACNB2,CHRNB4,MYD88,APAF1,FCN3,C LCN2,TLR5,CES2,DKFZp434N0935,HEY1,ABCG2,GSTT 1,SLC22A5,ent2,MOAT-B,SLC22A1,HTR3A,ABCC4,AGTR1,BC043424,SLC29A2 |
| amelogenesis imperfecta & gingival hyperplasia syndrome | amelogenesis imperfecta///amelogenesis imperfecta, hypocalcified///amelogenesis imperfecta, hypoplastic local///aminoacylase i deficiency | FAM83H,KLK4,ACY1,ARHGAP6,AMELX,ENAM |
| asthenozoospermia | asthenospermia///asthenozoospermia///asthenozoospermia, non-syndromic | PLA2G6,DNAI1,DNAH5,h-tektin-t,TEKT2,CFTR |

FIG. 27A

| | | |
|---|---|---|
| autism | autism///autism///epilepsy///autism and mental retardation///autism spectrum disorder///autism spectrum disorder and macrocephaly///autism spectrum association with///autism spectrum disorder, modifier of///autism spectrum disorders, development delay and macrocephaly///autism, association with///autism, seizures & intellectual disability | HTR5A,SLC6A4, CNTNAP2,AK095619, BC045795,LAMB 1,KCNJ10,JARID1C,CACNA1H,ASMT,SHANK3,OPHN1, SCN2A,AK309768,GLO1,DLX6,NOS1AP,MACP2,CADM 1,DOC2A,TDO2,NLGN3,MBD4,DIAPH3,PTEN,NLGN4Y ,NLGN4X,IMAA,EN2,hXIIL,PAX6,RPL10,GRPR,FREQ,G ABRB3,SEZ6L2,KIAA0951,NRP2,APBA2,GRIN2B,MET, MBD1,HTR3C,HOXA1,SCN1A,RIMS3,QM,SYN1 |
| autism spectrum disorder | autism///autism spectrum disorder///autism spectrum disorder, association with///autism spectrum disorder, modifier of///autism, association with///autism, seizures & intellectual disability///mental retardation/autism | HTR5A,SLC6A4, CNTNAP2,AK095619, BC045795,LAMB 1,ADSL,TDO2,JARID1C,CACNA1H,ASMT,SEZ6L2,OPH N1,SCN2A,AK309768,GLO1,DLX6,NOS1AP,NLGN4Y,C ADM1,DOC2A,KCNJ10,NLGN3,DIAPH3,MECP2,NLGN 4X,IMAA,EN2,SYN1,hXIIL,PAX6,RPL10,GRPR,FREQ,GA BRB3,SHANK3,KIAA0951,NRP2,APBA2,GRIN2B,MBD4 ,MBD1,HTR3C,HOXA1,SCN1A,RIMS3,QM,MET |
| autism spectrum dosorder | autism///autism spectrum disorder///autism spectrum disorder, association with///autism spectrum disorder, modifier of///autism, association with///autism, seizures & intellectual disability///mental retardation/autism | HTR5A,SLC6A4, CNTNAP2,AK095619, BC045795,LAMB 1,ADSL,TDO2,JARID1C,CACNA1H,ASMT,SEZ6L2,OPH N1,SCN2A,AK309768,GLO1,DLX6,NOS1AP,NLGN4Y,C ADM1,DOC2A,KCNJ10,NLGN3,DIAPH3,MECP2,NLGN 4X,IMAA,EN2,SYN1,hXIIL,PAX6,RPL10,GRPR,FREQ,GA BRB3,SHANK3,KIAA0951,NRP2,APBA2,GRIN2B,MBD4 ,MBD1,HTR3C,HOXA1,SCN1A,RIMS3,QM,MET |
| bardet-biedl syndrome | bardet-biedl syndrome///bardet-biedl syndrome~stoetzel~nat genet | BBS9,DKFZp434K1118,TTC8,ARL6,ASTN2,ZDHHC24,T MEM67,BBS1,BBS2,BBS5,BBS4,BBS7,CEP290,MKSI,B BS10,BBS12,TRIM32,RPGRIP1L,MKKS,D1 |
| bardet-biedl syndrome ? | bardet-biedl syndrome///bardet-biedl syndrome~stoetzel~nat genet | BBS9,DKFZp434K1118,TTC8,ARL6,ASTN2,ZDHHC24,T MEM67,BBS1,BBS2,BBS5,BBS4,BBS7,CEP290,MKSI,B BS10,BBS12,TRIM32,RPGRIP1L,MKKS,D1 |
| brugada syndrome | brugada syndrome///brugada syndrome (shorter-than-normal qt interval)///brugada syndrome & cardiac conduction disease///brugada syndrome, lidocaine-induced///brugada syndrome, phenotype modifier | KCNE3,Nav1.5,KCNH2,U80764,CACNB2,CACNA1C,SC N1B,GPD1L,SCN5A,SCN3B |

FIG. 27B

| | |
|---|---|
| cardiomyopathy, hypertrophic | cardiomyopathy///cardiomyopathy & distal myopathy///cardiomyopathy & late-onset polyneuropathy of lower limbs///cardiomyopathy with advanced av block///cardiomyopathy, arrhythmogenic left ventricular///cardiomyopathy, arrhythmogenic right ventricular///cardiomyopathy, arrhythmogenic left-dominant///cardiomyopathy, dilated///cardiomyopathy, dilated & cardiac conduction disease///cardiomyopathy, dilated with partial artial standstill///cardiomyopathy, dilated, and heart failure///cardiomyopathy, dilated, type 1a///cardiomyopathy, dilated, with conduction defect, type 1a///cardiomyopathy, hypertrophic///cardiomyopathy, hypertrophic with deafness///cardiomyopathy, hypertrophic, association with///cardiomyopathy, hypertrophic, modofier of, association with///cardiomyopathy, hypertrophic/dilated///cardiomyopathy, hypertropic///cardiomyopathy, left ventricular noncompaction///cardiomyopathy, neonatal///cardiomyopathy, non-compaction///cardiomyopathy, noncompaction, left ventricular///cardiomyopathy, restrictive///cardiomyopathy, restrictive with atrioventricular///cardiomyopathy, restrictive with atrioventricular block///cardiomyopathy, x-linked infantile | BAG3,ACTC1,PRKAG2,ILK,JPH2,MYL2,TNNC1,FKTN,RAF1,FLT1,MYH6,MYH7,PSEN1,SGCD,Nav1.5,TPM1,NEXN,DSG2,TCF21,TNNI3,LAMA2,LAMA4,CTF1,SRI,MYLK2,LDB3,SYNE1,TRXR2A,TCAP,PLN,CSRP3,CALR3,MYL3,OBSCN,TMPO,DMD,DES,CRYAB,MED26,HNTN1,AK05533,TNNT2,ANKRD1,CASQ2,TTR,JUP,MYPN,TTN,TXNRD2,C6orf204,BC042986,AK092087,VCL,CHRM2,DSP,FXN,KIAA0613,AK097470,LMNA,CALM3,H91620,ACTN2,TAZ,MYO6,MYBPC3,ABCC9,NDUFS7,MYOZ2,SCN5A |

FIG. 27C

| | |
|---|---|
| charcot-marie-tooth disease, axonal | charcot-marie-tooth disease///charcot-marie-tooth disease ~yoshihara~jpnervs///charcot-marie-tooth disease 1///charcot-marie-tooth disease 1a///charcot-marie-tooth disease 1b///charcot-marie-tooth disease 1c///charcot-marie-tooth disease 2///charcot-marie-tooth disease 2 with deafness///charcot-marie-tooth disease 2, assoc. with///charcot-marie-tooth disease 2~choi~hum mut///charcot-marie-tooth disease 2~fabrizi~brain///charcot-marie-tooth disease 2~jordanova~brain///charcot-marie-tooth disease 2~mersiyanova~ajhg///charcot-marie-tooth disease 2~miltenberger-miltenyi~arch neur///charcot-marie-tooth disease 2a///charcot-marie-tooth disease 2a, early-onset///charcot-marie-tooth disease 2b///charcot-marie-tooth disease 2c///charcot-marie-tooth disease 2d///charcot-marie-tooth disease 2d and distal spinal muscular atrophy///charcot-marie-tooth diseas 2l///charcot-marie-tooth disease 2k///charcot-marie-tooth disease 2k, axonal///charcot-marie-tooth disease 2l///charcot-marie-tooth disease 4///charcot-marie-tooth disease 4a///charcot-marie-tooth disease 4a, early onset axonal///charcot-marie-tooth disease 4b///charcot-marie-tooth disease 4b2///charcot-marie-tooth disease 4c///charcot-marie-tooth disease 4f///charcot-marie-tooth disease 4h///charcot-marie-tooth disease 4j///charcot-marie-tooth disease 5///charcot-marie-tooth disease with deafness///charcot-marie-tooth disease, 2b2///charcot-marie-tooth disease, autosomal dominant///charcot-marie-tooth disease, autosomal recessive///charcot-marie-tooth disease, axonal///charcot-marie-tooth disease, axonal, type 2f///charcot-marie-tooth disease, demyelinating///charcot-marie-tooth disease, early onset axonal///charcot-marie-tooth disease, intermediate///charcot-marie-tooth disease, spinal///charcot-marie-tooth disease, x-linked///charcot-marie-tooth disease, x-linked type 1 | LITAF,U80769,RAB7,SIMPLE,MED25,SBF2,FRABIN,DNM2,NDRG1,FBLN5,GDAP1,PRPS1,GJB1,NEFL,FIG4,YARS,TRPV4,PRX,FGD4,RAB7A,HSPB1,H11,HSPB8,HSP27,HTR4,KIAA0591,LMNA,EGR2,GARS,PMP22,KIF1B,SH3TC2,AARS,MTMR2,MFN2,Cap43,DKFZp66I2310,MPZ |
| chondrodysplasia & abnormal joint development | chondrodysplasia///chondrodysplasia punctata///chondrodysplasia punctata, x-linked///chondrodysplasia, grebe type | ARSE,RP3-477O4.13-001,EBP,GDF5 |

FIG. 27D

| | |
|---|---|
| colorectal cancer, increased risk, association with | colorectal adenoma, risk, association with///colorectal cancer///colorectal cancer, assoc. with///coloerectal cancer, association with///colorectal cancer, early onset///colorectal cancer, increased risk///colorectal cancer, increased risk, assoc. with///colorectal cancer, increased risk, association with///colorectal cancer, non-polyp. with incr risk of urothelial cancer///colorectal cancer, non-polyposis///colorectal cancer, non-polyposis-liu~zyxzz//colorectal cancer, non-polyposis, association///coloerectal cancer, non-polyposis, early, onset///colorectal cancer, predisposition to, association///colorectal cancer, predisposition, association///colorectal cancer, reduced risk, association with///colorectal cancer, risk, assoc. with///colorectal cancer, risk, association with///colorectal cancer, severe phenotype, association with///colorectal cancer, young-onset///colorectal neoplasia, reduced risk, association///colorectal neoplasia, reduced risk, association with | PTGS2,GHV,TRERF1,BUB1B,SMAD7,MUTYH,DKFZp564K192,CHFR,OGG1,NBS,HIF1AN,DCC,Chk2,CD86,ICAM5,NAV2,NBN,CASR,GOLGA5,FLCN,NFKBIA,MFI2,WNK1,REV3L,ERCC6,PMS1,PMS2,p53,LRP2,CYP1A1,BMP4,OGG1 type 1e,GH1,PLD2,OGG1 type 1f,AKAP9,FREM2,DQ515899,TLR1,BST1,PSMB9,APC,PAK7,DQ515897,MEP1B,EPHB2,IFIH1,DKFZp434N2420,TGFBR2,MSH2,MSH3,MSH6,BHD,INSR,MAP2K4,DHX36,AXIN2,MYO18B,hMLH1,CHIT1,EXO1,MLH3,MLH1,XPC,ABCB1,DQ515898,CDC6,ANXA11,FLJ00314,CHEK2,AGXT2L1,NUDT1,PARP1,IGFBP3,POU5F1,hOGG1,DTNBP1,APC variant protein, AOAH,TP53,MTHFD1,BCL2A1,DNAH9,CA6,COX-2,MPP3,EPM2AIP1,MYBPC1,Tbeta RIIC,ASCC3,MMP2,ITGAE |
| complex i deficiency | complex 1 and 3 deficiency, combined///complex1 deficiency///complex i deficiency///isolated complex i deficiency///mitochondrial complex 1 deficiency///mitochondrial complex 1 deficiency, neonatal///mitochondrial complex i deficiency | C8orf38,PEO1,NDUFA1,mccb,C3orf60,NDUFA8,POLG,AMACR,NDUFAF1,DKFZp586K0821,NDUFAF2,GNPAT,GAD1,PHYN,IVD,C7orf10,NDUFV1,GPAM,C6orf66,C10orf2,NDUFS2,MCCC2,NDUFS1,mimitin,NDUFS3,NDUFS4,NDUFS6,NDUFS8,OXCT1,C20orf7,DHAPAT,RP1 1-426E5.2 |

FIG. 27E

| | |
|---|---|
| cogenital cataracts | colorectal cancer///colorectal cancer, assoc. with///colorectal cancer, association with///colorectal cancer, early onset///colorectal cancer,increased risk///colorectal cancer, increased risk, assoc. with///colorectal cancer, increased risk, association with///colorectal cancer, non-polyp. with incr risk of urothelial cancer///colorectal cancer, non-polyposis///colorectal cancer, non-polyposis~liu~zyxzz///colorectal cancer, non-polyposis, association///colorectal cancer, non-polyposis, early-onset///colorectal cancer, predisposition to, association///colorectal cancer, predisposition, association///colorectal cancer, reduced risk, association///colorectal cancer, reduced risk, association with///colorectal cancer, risk, assoc. with///colorectal cancer, risk, association with///colorectal cancer, severe phenotype, association with///colorectal cancer, young-onset | PTGS2,TRERF1,BUB1B,SMAD7,MUTYH,DKFZp564K192,CHFR,OGG1,NBS,HIF1AN,DCC,Chk2,CD86,ICAM5,NAV2,NBN,GOLGA5,FLCN,MSH3,MFI2,WNK1,REV3L,MSH6,PMS1,PMS2,p53,LRP2,CYP1A1,BMP4,OGG1 type 1e,PLD2,OGG1 type 1f,AKAP9,FREM2,DQ515899,TLR1,BST1,PSMB9,APC,PAK7,DQ515897,MEP1B,AGXT2L1,IFIH1,DKFZp434N2420,TGFBR2,MSH2,NFKBIA,ERCC6,CA6,INSR,MAP2K4,DHX36,AXIN2,MYO18B,hMLH1,CHIT1,EXO1,MLH3,MLH1,XPC,ABCB1,DQ515898,CDC6,ANXA11,FLJ00314,CHEK2,EPHB2,NUDT1,PARP1,IGFBP3,POU5F1,hOGG1,DTNBP1,APC variant protein, AOAH,TP53,MTHFD1,BCL2A1,DNAH9,BHD,COX-2,MPP3,EPM2AIP1,MYBPC1,Tbeta RIIC,ASCC3,MMP2,ITGAE |
| deafness, non-syndromic, autosomal recessive | deafness///deafness, autosomal recessive///deafness, autosomal recessive 1///deafness, autosomal recessive 12///deafness, autosomal recessive 12, modofier of///deafness, autosomal recessive 21///deafness, autosomal recessive 9///deafness, childhood onset///deafness, non-syndromic///deafness, non-syndromic, autosomol recessive///deafness, nonsyndromic///deafness, nonsyndromic sensorineural///deafness, nonsyndromic sensorineural 25///deafness, sensorineural non-syndromic 11///deafness, unilateral | TMC1,CLDN14,TMIE,KIAA1812,BSND,DKFZp4340111 9,DFNB31,MYOG,GJB3,GJB2,GJB4,GJB6,MARVELD2,USH1C,TECTA,CDH23,TMPRSS3,TMPRSS5,DKFZp434P2350,DKFZp686N18198,SLC26A5, aie-75,ATP2B2,PMCA2,GJA1,SLC17A8,TRIOBP,KIAA0389,GJC3,OTOF,KIAA1199,PCDH15,SLC26A4,MYO15A,MYO7A,BC022493, PRES |

FIG. 27F

| | |
|---|---|
| diabetes mellitus, type 2 | diabetes mellitus 2, association with///diabetes mellitus 2, early onset, association with///diabetes mellitus, type2///diabetes mellitus, type 2 & gestational///diabetes mellitus, type 2, association with///diabetes mellitus, type 2, association with~konheim~hum genet///diabetes, niddm///diabetes, niddm, association with///diabetes, niddm, increased risk///diabetes, niddm, susceptibility to///diabetes, niddm, susceptibility, association///diabetes, type 2///diabetes, type 2, assoc. with///diabetes, type 2, association with///diabetes, type 2, association with~bonnycastle~diabetes///diabetes, type 2, association with~han~bdxxb///diabetes, type 2, association with~sandhu~nat genet///diabetes, type 2, early-onset///diabetes, type 2, increased risk///diabetes, type 2, increased risk, assoc.///diabetes, type 2, lower risk, association with///diabetes, type 2, protection against, association with~dahlman~bmc mg///diabetes, type 2, protection, association///diabetes, type 2, reduced risk///diabetes, type 2, reduced risk, assoc. with///diabetes, type 2, reduced risk, association with///diabetes, type 2, risk, assoc. with///diabetes, type 2, suscept., association with///diabetes, type 2, suspectibility to, association///diabetes, type 2, reduced risk, association with///microangiopathy in type 2 diabetes, association///obesity and diabetes type 2, association with///proteinuria in type 2 diabetes, association with///type 2 diabetes, age of onset, association with///type 2 diabetes, association | CD38,PTGS2,TGM2,PCK1,PCSK2,ISL1,CPE,CACNA1E,FABP6,SLC30A8,UCP1,OGG1,KLF7,BC017935,CR593175,IRS1,RETN,CERKL,LOC728661,HNF1A,ARHGEF11,LIPC,HHEX,SOD3,ACACB,HK2,RXRG,AGER,LTA,RBP4,SLCO1A2,KIAA1845,MAPK8IP1,DB1,PYY,NEUROD1,PTGES2,KCNJ9,SLC2A4,SLC2A2,ATL1,CAPN10,PTEN,ADRB2,ADRB3,CDC2L1,CDC2L2,WFS1,ATP2A3,CLPS,KIAA1767,PIK3C2G,CAT,INSR,TCF7L2,GPD2,GIPR,LARS2,EXT2,STX1A,APOE,LPIN2,RAGE,APOM,PPARGC1A,HNF1B,SREBP-1a,SREBF1,PGC-1v,ADIPOQ,PIK3R1,NEUROG3,SLC35E2,NPPB,THADA,NR1H2,UTS2,KCNJ11,KCNJ15,IRS2,GCK,CHRM3,KLF1,IAPP,KCNQ1,PAX4,TNF,GITA-A2-GFPT1,MTNR1B,GITA/3p fusion,FTO,INS-IGF2,SH3TC2,HNF4A,COX-2,INS,MTTP,ABCC8,ABCC9,BTC,PDX1,ATF6 |

FIG. 27G

| | | |
|---|---|---|
| diabetes mellitus, type 2 | diabetes mellitus 2, association with///diabetes mellitus 2, early onset, association with///diabetes mellitus, type2///diabetes mellitus, type 2 & gestational///diabetes mellitus, type 2, association with///diabetes mellitus, type 2, association with~konheim~hum genet///diabetes, niddm///diabetes, niddm, increased risk///diabetes, niddm, susceptibility to///diabetes, niddm, susceptibility, association///diabetes, type 2///diabetes, type 2, assoc. with///diabetes, type 2, association with///diabetes, type 2, association with~bonnycastle~diabetes///diabetes, type 2, association with~han~bdxxb///diabetes, type 2, association with~sandhu~nat genet///diabetes, type 2, early onset///diabetes, type 2, increased risk///diabetes, type 2, increased risk, assoc.///diabetes, type 2, lower risk, association with///diabetes, type 2, protection against, association with~dahlman~bmc mg///diabetes, type 2, protection, association///diabetes, type 2, reduced risk///diabetes, type 2, reduced risk, assoc. with///diabetes, type 2, risk, assoc. with///diabetes, type 2, suscept., association with///diabetes, type 2, suspectibility to, association///diabetes, type 2, reduced risk, association with///microangiopathy in type 2 diabetes, association///obesity and diabetes type 2, association with///proteinuria in type 2 diabetes, association with///type 2 diabetes, age of onset, association with///type 2 diabetes, association with | CD38,PTGS2,TGM2,PCK1,PCSK2,ISL1,CPE,CACNA1E,F ABP6,SLC30A8,UCP1,OGG1,KLF7,BC017935,CR59317 5,IRS1,RETN,CERKL,LOC728661,HNF1A,ARHGEF11,LI PC,HHEX,SOD3,ACACB,HK2,RXRG,AGER,LTA,RBP4,SL CO1A2,KIAA1845,MAPK8IP1,DB1,PYY,NEUROD1,PTG ES2,KCNJ9,SLC24A,SLC2A2,ATL1,CAPN10,PTEN,ADRB 2,ADRB3,CDC2L1,CDC2L2,WFS1,ATP2A3,CLPS,KIAA1 767,PIK3C2G,CAT,INSR,TCF7L2,GPD2,GIPR,LARS2,EX T2,STX1A,APOE,LPIN2,RAGE,APOM,PPARGC1A,HNF1 B,SREBP-1a,SREBF1,PGC-1v,ADIPOQ,PIK3R1,NEUROG3,SLC35E2,NPPB,THADA, NR1H2,UTS2,KCNJ11,KCNJ15,IRS2,GCK,CHRM3,KLF1 1,IAPP,KCNQ1,PAX4,TNF,GITA-A2-GFPT1,MTNR1B,GITA/3p fusion,FTO,INS-IGF2,SH3TC2,HNF4A,COX-2,INS,MTTP,ABCC8,ABCC9,BTC,PDX1,ATF6 |
| diffuse mesangial sclerosis | diffuse mesangial sclerosis | WT1,PLCE1,KIAA1516,NPHS1 |
| focal segmental glomerulosclerosis, childhood familial | focal segmental glomerulosclerosis///focal segmental glomerulosclerosis, assoc. with///focal segmental glomerulosclerosis, association with~orloff~phys genom///focal segmental glomerulosclerosis, reduced risk, assoc. with | MMP14,WT1,C1orf125,WIT1,BC035052,C14orf151,A K056332,COL4A3,NPHS1,TRPC6,DKFZp43N1720,NP HS2,INF2 |
| fraser syndrome | fraser syndrome | FREM2,DKFZp686L06109 |
| gnrh deficiency | gnrh deficiency | KISS1R,PROK2,AJ617629,TAC3,MST123,KAL1,PROKR 2,GNRHR,ZNEUROK1,FGFR1 |

FIG. 27H

| | | |
|---|---|---|
| hearing loss, non-syndromic, autosomal recessive | hearing impairment, nonsyndromic, autosomal recessive///hearing loss///hearing loss with dilation of vestibular aqueduct///hearing loss, digenic non-syndromic///hearing loss, non-syndromic///hearing loss, non-syndromic sensorineural///hearing loss, non-syndromic, autosomal recessive///hearing loss-non-syndromic, sensorineural///hearing loss, x-linked nonsyndromic | TECTA,KCNJ10,ESPN,ESRRB,POU3F4,TMPRSS3,GRXCR1,COL9A3,ERRB2,SLC26A4,DFNB59,LHFPL5,RDX,SERPINB6,GJB2,GJC3,OTOF,CDH23,DKFZp43410812,DKFZp43401119,MYO15A,GPSM2,BC022493 |
| hermansky-pudlak syndrome 9 | hermansky-pudlak syndrome///hermansky-pudlak syndrome 6 | DKFZp666K145,AP3B1,KIAA1667,HPS5,HPS4,HPS6,,HPS1,DKFZp564K192,HPS3,DTNBP1 |
| hirschsprung disease | hirschsprung disease///hirschsprung disease, assoc. with///hirschsprung disease, association with///hirschsprung disease, association with~fitze~hum mut | NTF3,RET,POLR2F,ECE1,L1CAM,SFTA3,EDNRB,NKX2-1,BX161496,AXIN2,SOX10,BC031243,NTRK3,PROKR2,GDNF,EDN3,NRTN |
| holoprosencephaly | holoprosencephaly///holoprosencephaly and moyamoya disease | GLI2,DHCR7,GLI2,GAS1,SIX3,ZIC2,TGIF1,SHH,hGli2,PTCH1,AX746648 |
| holoprosencephaly, susceptibility to | holoprosencephaly///holoprosencephaly and moyamoya disease///holoprosencephaly-like phenotype | Gli2,PTCH1,DHCR7,GLI2,SHH,ZIC2,AX746648,GAS1,hGli2,SIX3,TGIF1 |
| hypertriglyceridaemia | hyperbiliverdinaemia///hyperglycaemia///hyperglycaemia, reduced risk, association with///hyperglycaemia, non-ketotic///hyperglycinaemia, transient neonatal///hyperlipidaemia///hyperlipidaemia 3///hyperlipidaemia, association with///hypertriglyceridaemia///hypertriglyceridaemia, association with///hypertriglyceridaemia///hypertriglyceridaemia, reduced risk, assoc. with///hypertriglyceridaemia & lipase deficiency///hyperuricaemia///hyperuricaemia with neurologic symptoms///hyperuricaemia without neurologic symptoms///osteoporosis & hyperlipidaemia | RP1,LIPC,RXRG,LIPI,GCK,LA16c-360B4.1-001,GCKR,FABP4,LPL,APOC3,APOA4,APOA5,BLVRA,HPRT1,APOA1,SLC10A2,APOE,APOB,LRP5,GLDC,LMF1,SLC17A3,AMT,ABCC8,AK308047 |
| hypertrophic cardiomyopathy, fatal neonatal | hypertrophic cardiomyopathy///hypertrophic cardiomyopathy and encephalopathy///hypertrophic cardiomyopathy, early onset///hypertrophy, moderate | NDUFV2,PRKAG2,CAV3,COX15 |
| hyperuricaemia, pulmonary hypertension, renal failure & alkalosis | hyperuricaemia///hyperuricaemia with neurologic symptoms///hyperuricaemia without neurologic symptoms///hyperuricaemia nephropathy///hyperuricaemic nephropathy, juvenile | HNF1B,HPRT1,UMOD,SLC17A3 |

FIG. 271

| | | |
|---|---|---|
| hypogonadotropic hypogonadism, idiopathic | adren. hypoplasia & hypogonadotrophic hypogonadism///hypogonadotrophic hypogonadism, idiopathic///hypogonadotropic hypogonadism///hypogonadotropic hypogonadism, idiopathic///hypogonadotropic hypogonadism, isolated | KISS1R,SOX2OT,AJ617629,GNRH1,PPP2R2A,KIAA1416,GNRHR,FGF8,SOX2,TACR3,FGFR1,CHD7,NR0B1,TAC3,MST123,KAL1,PROKR2,PROP1,ZNEUROK1,fgf8f |
| hypomagnesemia | hypercalciuria, neophrolithiasis & hypomagnesemia///hypomagnesaemia with secondary hypocalcaemia///hypomagnesaemia, renal///hypomagnesemia///hypomagnesemia with hypercalciuria and neophrocalcinosis///hypomagnesemia, isolated///hypomagnesemia, renal failure & severe ocular abnormalities///hypomagnessmia, renal failure & severe ocular abnormalities~konrad~ajhg | CHAK2,CLDN16,CLDN19,HNF1B,FXYD2,TRPM6,EGF,KCNA1 |
| hypopituitarism | hypopituitarism///hypopituitarism & ectopic posterior pituitary lobe///hypopituitarism and sensorineural hearing loss///hypopituitarism and/or post-axial polydactyly | GLI2,Gli2,LHX3,LHX4,hGli2 |
| hypospadias ? | adrenal insufficiency & hypospadias///hypospadias///hypospadias, association with///hypospadias~silver~jurol///hypospadias~wang~ejhg | WT1,K-sam,HOXB6,BMP4,FGF8,HOXA4,FGFR2,MID1,BMP7,CYP11A1,ESR2,MAMLD1,AR,SRD5A2,fgf8f,ATF3 |
| hypotrichosis simplex | hypotrichosis///hypotrichosis & recurrent skin vesicles///hypotrichosis simplex of the scalp///hypotrichosis with juvenile mascular dystrophy///hypotrichosis-lymphoedema-telangiectasia///hypotrichosis, autosomal recessive | SOX18,PSORS1C1,LIPH,DSC3,RB1,CDSN,CDH3,DSG4,P2RY5 |

FIG. 27J

| | |
|---|---|
| immunodeficiency, autosomal dominant | immune deficiency///immunodef., centromeric instability and facial anomalies syndrome///immunodeficiency///immunodeficiency syndrome, common variable///immunodeficiency with hyper-igm///immunodeficiency with microcephaly///immunodeficiency with radiosensitivity///immunodeficiency, combined///immunodeficiency, common variable///immunodeficiency. late onset///immunodeficiency, primary b-cell///immunodeficiency, severe combined///immunodeficiency, severe combined, atypical///immunodeficiency, severe combined, b-cell ve///immunodeficiency, severe combined, t & b-cell ve///immunodeficiency, t-cell defect///immunodeficiency, x-linked | IL7R,DOCK8,SH2D1A,IKK-gamma,UNG,CD247,MAGT1,IKBKG,CD79B,DCLRE1C, CIITA,PIK3CD,LIG4,JAK3,CERNUNNOS,LIG1,DNMT3B,I COS,RAG2,MHC2TA,SCIDA,ZAP70,TNFRSF13B,NHEJ1, IL2RA,IL2RG,XIAP,ADA,RAG1,PTPRC,TLR5,CD3D,CD3E ,CD3G |
| immunodeficiency, autosomal recessive | immune deficiency///immunodef., centromeric instability and facial anomalies syndrome///immunodeficiency///immunodeficiency syndrome, common variable///immunodeficiency with hyper-igm///immunodeficiency with microcephaly///immunodeficiency with radiosensitivity///immunodeficiency, combined///immunodeficiency, common variable///immunodeficiency. late onset///immunodeficiency, primary b-cell///immunodeficiency, severe combined///immunodeficiency, severe combined, atypical///immunodeficiency, severe combined, b-cell ve///immunodeficiency, severe combined, t & b-cell ve///immunodeficiency, t-cell defect///immunodeficiency, x-linked | IL7R,DOCK8,SH2D1A,IKK-gamma,UNG,CD247,MAGT1,IKBKG,CD79B,DCLRE1C, CIITA,PIK3CD,LIG4,JAK3,CERNUNNOS,LIG1,DNMT3B,I COS,RAG2,MHC2TA,SCIDA,ZAP70,TNFRSF13B,NHEJ1, IL2RA,IL2RG,XIAP,ADA,RAG1,PTPRC,TLR5,CD3D,CD3E ,CD3G |

FIG. 27K

| | | |
|---|---|---|
| immunodeficiency, centromeric instability & facial anom. syndrome | immune deficiency///immunodef., centromeric instability and facial anomalies syndrome///immunodeficiency///immunodeficiency syndrome, common variable///immunodeficiency with hyper-igm///immunodeficiency with microcephaly///immunodeficiency with radiosensitivity///immunodeficiency combined///immunodeficiency, common variable///immunodeficiency, late onset///immunodeficiency, primary b-cell///immunodeficiency, severe combined///immunodeficiency, severe combined, atypical///immunodeficiency, severe combined, b-cell ve///immunodeficiency, severe combined, t & b-cell ve///immunodeficiency, t-cell defect///immunodeficiency, x-linked | IL7R,DOCK8,SH2D1A,IKK-gamma,UNG,CD247,MAGT1,IKBKG,CD79B,DCLRE1C,CIITA,PIK3CD,LIG4,JAK3,CERNUNNOS,LIG1,DNMT3B,ICOS,RAG2,MHC2TA,SCIDA,ZAP70,TNFRSF13B,NHEJ1,IL2RA,IL2RG,XIAP,ADA,RAG1,PTPRC,TLR5,CD3D,CD3E,CD3G |
| impaired sperm function, association with | impaired spermatogenesis///impaired spermatogenesis, association with | RBMXL2,DDX25 |
| inflammatory bowel disease, association with | inflammatory bowel disease///inflammatory bowel disease, association with///inflammatory bowel disease, risk, assoc. with///inflammatory demyelinating neuropathy///inflammatory diseases, association with | KRT8,DLG5,IL10RA,IL10RB,GJB1,CIITA,MST1,ABCB1,GLI1,KIAA0583,MYO9B,MHC2TA,MYO9B variant protein, SLC15A1,1L1R1,KRT18 |
| intellectual disability, motor dysfunction & joint contractures | intellectual disability///intellectual disability, nonsyndromic///intellectual disability, nonsyndromic without epilepsy///intellectual disability, nonsyndromic, autosomal recessive///intellectual disability, x-linked | STXBP1,UNQ747,SLC9A3R2 variant protein, TSC2,MED23,ST3GAL4,KIAA1867,MAN1B1,CNTNAP2,KIRREL3,CDH15,SHANK3,ATRX,JARID1C |
| intellectual disability nonsyndromic | autism, seizures & intellectual disability///infantile spasms & intellectual disability///intellectual disability///intellectual disability, nonsyndromic///intellectual disability, nonsyndromic disability, nonsyndromic///intellectual disability, nonsyndromic without epilepsy///intellectual disability, nonsyndromic, autosomal recessive///intellectual disability, x-linked///intractable epilepsy and intellectual disability | KCNJ10,UNQ747,SLC9A3R2 variant protein,MED23,SLC6A8,STXBP1,CNTNAP2,ATRX,KIRREL3,TSC2,JARID1C,MAN1B1,KIAA1867,ARX,SHANK3,CDH15,ST3GAL4 |

FIG. 27L

| | | |
|---|---|---|
| intellectual disability nonsyndromic, autosomal recessive | autism, seizures & intellectual disability///infantile spasms & intellectual disability///intellectual disability///intellectual disability, nonsyndromic///intellectual disability, nonsyndromic without epilepsy///intellectual disability, nonsyndromic, autosomal recessive///intellectual disability, x-linked///intractable epilepsy and intellectual disability | KCNJ10,UNQ747,SLC9A3R2 variant protein,MED23,SLC6A8,STXBP1,CNTNAP2,ATRX,KIRREL3,TSC2,JARID1C,MAN1B1,KIAA1867,ARX,SHANK3,CDH15,ST3GAL4 |
| intellectual disability, spastic paraplegia & short stature | intellectual disability///intellectual disability, nonsyndromic///intellectual disability, nonsyndromic without epilepsy///intellectual disability, nonsyndromic, autosomal recessive///intellectual disability, x-linked | STXBP1,UNQ747,SLC9A3R2 variant protein, TSC2,MED23,ST3GAL4,KIAA1867,MAN1B1,CNTNAP2,KIRREL3,CDH15,SHANK3,ATRX,JARID1C |
| joubert syndrome | joubert syndrome///joubert syndrome, senior-loken type | TMEM67,ARL13B,INPP5E,KIAA1005,AHI1,CEP290,CC2D2A,ARL2L1,KIAA1345,RPGRIP1L,OFD1 |
| kallmann syndrome | kallmann syndrome///kallmann syndrome, reversible | CHD7,PROK2,AJ617629,MST123,KAL1,PROKR2,GNRHR,FGFR1 |
| larsen-like syndrome, b3gat3 type | larser syndrome, autosomal dominant///larsen syndrome, autosomal recessive | FLNB,CHST3 |
| meckel-gruber syndrome | meckel syndrome///meckel-gruber syndrome///meckel-gruber-like syndrome | TMEM67,NPHP3,KIAA1005,TMEM91,CEP290,MKS1,CC2D2A,KIAA1345,RPGRIP1L,B9D2 |
| meckel-gruber-like syndrome | meckel syndrome///meckel-gruber syndrome///meckel-gruber-like syndrome | TMEM67,NPHP3,KIAA1005,TMEM91,CEP290,MKS1,CC2D2A,KIAA1345,RPGRIP1L,B9D2 |
| medulloblastoma, desmoplastic | medulloblastoma | TP53,DICER1,p53 |
| megalencephalic leukoencephalopathy with subcortical cysts | megalencephalic leukoencephalopathy///megalencephalic leukoencephalopathy with subcortical cysts | MLC1 |
| meier-gorlin syndrome | meier-gorlin syndrome | ORC4L,CDC6 |

FIG. 27M

| | | |
|---|---|---|
| mental retardation, non-syndromic, autosomal recessive | mental retardation///mental retardation, in women, association with///mental retardation, in women, association with~sun~hmg///mental retardation, mild///mental retardation non-specific///mental retardation, non-specific, x-linked///mental retardation, non-syndromic, autosomal recessive///mental retardation, pitt-hopkins-like///mentsal retardation, x-linked///mental retardation, x-linked, association with///mental retardation|kleefstra~ajhg | ZCCHC12,IL1RAPL1,RAB39B,GRIA3,FOXG1,SLC6A8,S MS,PQBP1,JM26,KIAA0312,MAGT1,AP1S2,SHROOM 4,DMD,PLP2,RS1,ATRX,JARID1C,EHMT1,MEF2C,DLG3 ,CR605926,ARX,CDKL5,OPHN1,CASK,FTSJ1,xpct,MED 12,CRBN,CDK5R1,NF1,BRWD3,ZNF81,FP13812,TRAP PC9,HUWE1,FGD1,ZNF41,AY927613,MECP2,NLGN4X ,SLC9A6,ZNF674,TSPAN7,FLNA,EFHC2,GDI1,ELK1,POU 1F1,DKFZp779P0659,RPS6KA3,OMG,UBE2A,SLC16A2 ,ZNF711,ACSL4,MBD5,UPF3B,ELK1,CUL4B,AGTR2,CN TNAP2,ZDHHC9,SYP |
| metabolic syndrome, association with | metabolic syndrome///metabolic syndrome traits, association with///metabolic syndrome, association with///metabolic syndrome, association with~savill~ajhyp///metabolic syndrome, reduced risk, association with///metabolic syndrome, susceptibility, association | AK310237,PYY,TFR2,TPM1,RGS2,LMNA,CD36,AX747 619 |
| microcephaly with simplified gyration, epilepsy & disease | microcephaly///microcephaly///microcephaly with microlissencephaly/////microcephaly///microcephaly with brainstem & cerebellar hypoplasia///microcephaly, optic atrophy and hypoplasia, lactic acidemia///microcephaly, seizures & developmental delay///microcephaly, severe | MRE11B,MRE11A,NR2E1,SLC25A19,DEM1,NDE1,DN M1L,PNKP,CASK |
| microphthalmia with limb anomalies | microphthalmia///microphthalmia with associated anomalies///microphthalmia with retinitis pigmentosa///microphthalmia, bilateral & colobomal///microphthalmia, cataract and iris abnormality///microphthalmia, nonsyndromic bilateral///microphthalmia, syndromic 7///microphthalmia, syndromic 9 | HCCS,SOX2OT,MFRP,STRA6,FOXE3,PP14296,BCOR,V SX2,SOX2,RAX,CRYBA4 |
| mosaic variegated aneuploidy | mosaic variegated aneuploidy | PAK6,BUB1B |
| mucocutaneous candidiasis | mucocutaneous candidiasis | IL17K, STAT1 |

FIG. 27N

| | | |
|---|---|---|
| muscular dystrophy, mental retardation & enlarged mitochondria | muscular dystophy///muscular dystophy & mental retardation///muscular dystrophy & peripheral neuropathy///muscular dystrophy with epidermolysis bullosa///muscular dystrophy without cardiomyopathy or brain involvement///muscular dystrophy , becker///muscular dystrophy, becker with cognitive impairment///muscular dystrophy, congential///muscular dystrophy, congenital 1a///muscular dystrophy, congenital 1d///muscular dystrophy, congenital with mental retardation///muscular dystrophy, congenital-topaloglu-neurology///muscular dystrophy, duchenne///muscular dystrophy, duchenne-like///muscular dystrophy, duschenne/becker///muscular dystrophy,emery-dreifuss///muscular dystrophy, emery-dreifuss, neuogenic///muscular dystrophy, fukuyama///muscular dystrophy, hypertonic fatal infantile///muscular dystrophy, intermediate///muscular dystrophy, limb girdle///muscular dystrophy, limb girdle / miyohi myopathy///muscular dystrophy, limb girdle 1a///muscular dystrophy, limb girdle 2///muscular dystrophy, limb girdle 2a///muscular dystrophy, limb girdle 2b///muscular dystrophy, limb girdle 2c///muscular dystrophy, limb girdle 2d///muscular dystrophy, limb girdle 2d, late-onset///muscular dystrophy, limb girdle 2e///muscular dystrophy, limb girdle 2f///muscular dystrophy, limb girdle 2g///muscular dystrophy, limb girdle 2h///muscular distrophy, limb girdle 2l///muscular dystrophy, limb girdle 2ll///muscular dystrophy, limb girdle, with cardiomyopathy///muscular dystrophy, limb girdle/miyoshi myopathy///muscular dystrophy, merosin deficient///muscular dystrophy, progressive | EMD,UDP-GlcAc,DMD,TRIM32,KIAA1011,CRYAB,MYOT,LARGE,FKTN,CAV3,FKRP,SGCG,SYNE1,SGCD,SGCB,SGCA,C3orf32,FHL1,CAPN3,ANO5,LAMA2,PLEC1,DYSF,ASTN2,DAG1,BC035400,SYNE2,TCAP,POMGNT1,DKFZp686J1865,LMNA,POMT1,POMT2 |
| myoclonic epilepsy of lafora | myoclonic epilepsy of lafora | NHLRC1,EPM2A,AK124757 |

FIG. 27O

| | | |
|---|---|---|
| myoclonus epilepsy | myoclinic epilepsy, neonatal///myoclonic epilepsy///myoclonic epilepsy, juvenile///myoclonic epilepsy, juvenile, association with///myoclonic-astatic epilepsy///myoclonus epilepsy///myoclonus epilepsy with declining mental status///myoclonus epilepsy without renal failure | PRICKLE1,SLC25A22,SCARB2,KIAA1123,CACNA1G,CH RNA4,SCN1A,SERPINI1,EFHC1,CACNB4,GABRA1,GJD2 |
| nephronophthisis | nephronophthisis///nephronophthisis 1///nephronophthisis 2///nephronophthisis 3///nephronophthisis 4///nephronophthisis with liver fibrosis | NPHP3,TMEM67,KIAA0673,NPHP4,KIAA2000,INVS,N PHP1 |
| nephrotic syndrome | nephrotic syndrome///nephrotic syndrome 3, early onset///nephrotic syndrome, steroid resistant | WT1,C1orf125,DKFZp434N1720,CR599144,CD2AP,S MARCAL1,DKFZp434B1050,NPHS2,KIAA1516,TRPC6, NPHS1,PLCE1,LAMB2 |
| nephrotic syndrome with sensorineural deafness | nephrotic syndrome///nephrotic syndrome 3, early onset///nephrotic syndrome, steroid resistant | WT1,C1orf125,DKFZp434N1720,CR599144,CD2AP,S MARCAL1,DKFZp434B1050,NPHS2,KIAA1516,TRPC6, NPHS1,PLCE1,LAMB2 |
| nephrotic syndrome, steroid resistant | nephrotic syndrome///nephrotic syndrome 3, early onset///nephrotic syndrome, steroid resistant | WT1,C1orf125,DKFZp434N1720,CR599144,CD2AP,S MARCAL1,DKFZp434B1050,NPHS2,KIAA1516,TRPC6, NPHS1,PLCE1,LAMB2 |
| neuronal ceroid lipofuscinosis, adult-onset | neuronal ceroid lipofuscinoses, late infantile///neuronal ceroid lipofuscinoses///neuronal ceroid lipofuscinosis 4a, autosomal recessive///neuronal ceroid lipofuscinosis 4a, adult///neuronal ceroid lipofuscinosis , early childhood///neuronal ceroid lipofuscinosis, finish variant///neuronal ceroid lipofuscinosis, infantile///neuronal ceroid lipofuscinosis, juvenile///neuronal ceroid lipofuscinosis, late infantile | MFSD8,PPT1,CLN6,CLN5,CLN3,TPP1,CLN8 |
| nonalcoholic fatty liver disease, increased risk, assoc. with | non-alcoholic fatty liver disese, association with | PEMT |

FIG. 27P

| | | |
|---|---|---|
| osteogenesis imperfecta / bruck syndrome | osteogenesis imperfecta i///osteogenesis imperfecta ii///osteogenesis imperfecta ia///osteogenesis imperfecta ii///osteogenesis imperfecta ii/iii///osteogenesis imperfecta iia///osteogenesis imperfecta iic///osteogenesis imperfecta iii///osteogenesis imperfecta iii/iv///osteogenesis imperfecta iii-kataoka-ped int///osteogenesis imperfecta iv///osteogenesis imperfecta, autosomal recessive///osteogenesis imperfecta, recessive | CR623026,COL1A2,casp,COL1A1,SNX22,SERPINF1,SE RPINH1,LEPRE1,PPIB,CRTAP |
| osteogenesis imperfecta, autosomal recessive | ehlers-danlos syndrome/osteogenesis imperfecta///osteogenesis imperfecta///osteogenesis imperfecta, autosomal recessive///osteogenesis imperfecta, recessive///osteogenesis autosomol recessive | OSTM1,CR623026,TNFRSF11A,CLCN7,TNFSF11,RANK ,TCIRG1,COL1A2,casp,COL1A1,SNX22,SERPINF1,SERP INH1,LEPRE1,PPIB,TIRC7,CRTAP |
| periodontitis, generalized aggressive, assoc. with | periodontitis, aggressive, association with///periodontitis, assoc. with///periodontitis, increased risk, association with///periodontitis, juvenile///periodontitis, juvenile, association with | DEFB1,LTF,FPR1,FPR2,CTSC,CSF1 |
| perrault syndrome | perrault syndrome | HSD17B4 |
| pheochromocytoma | phaeochromocytoma///phaeochromocytoma & medullary thyroid carcinoma///phaeochromocytoma and paraganglioma///phaeochromocytoma-paraganglioma syndrome | VHL,TMEM127,DKFZp686J1293,NF1,SDHC,SDHB,LOC 642502,SDHD,RET |
| polymicrogyria | polymicrogyria///polymicrogyria with optic nerve hypoplasia///polymicrogyria, asymmetrical///polymicrogyria bilateral frontoparietal | DKFZp566F223,GPR56,TUBA8,TUBA1B,TUBA1A,TUB B2B |

FIG. 27Q

| | |
|---|---|
| potential protein deficiency | potential protein deficiency///potential protein deficiency~savas~hum genom///potential protein deficiency~yngvadottir~ajhg | SYTL5,EPHX1,STK19,TEX14,SAGE,SDCCAG1,HPS4,APOC4,CLCA3,AGT,MLSN1,ROS1,AXL,RNF113A,POLE2,SLC10A2,DOM3Z,SMG1,CDC73,GRK4,SAGE1,GOPC,LIG4,OAS2,AY187250,LYN,TTN,KRTAP1-1,RPS6KL1,FRK,COG1,WNK1,PASK,H2BFWT, interleukin 9 receptor,SIGLEC12,ANKK1,ZCCHC13,TNNI3K,GNAQ,SMUG1,TBCK,TBCKL,UBE2NL,OVCH2,TAF1L,pknbeta,TLR4,CDK7,OBSCN,CDH15,NSDHL,Trad,KALRN,VSIG4,MAP2K3,MAGEE2,SPTBN5,AK057625,SEMA4C,UNQ9215,RAGE,KIAA1667,LCE5A,PNPLA2,NOD1,AURKA,AURKC,APOL3,TRPM1,UNC93A,ITIH5L,ITGB3,GUCY2D,DPE2,H11,PKN3,IL9R,HSPB8,MST1R,P2RY4,KIAA1381,DSCR8,FAM47B,ROCK1,MAOB,MAP3K15,MS4A12,ZAN,ABCC3 |
| primary ciliary dyskinesia | primary ciliary dyskinesia///primary ciliary dyskinesia and situs inversus ~bartoloni~pnas | KIAA1603,LRRC50,DNAH11,DNAH5 |
| progeroid syndrome | progeroid facial features & lipodystrophy///progeroid syndrome///progeroid syndrome, atypical | LMNA,ERCC4,FBN1 |
| progressive hearing impairment | progressive hearing loss///progressive hearing loss, autosomal recessive | AK097779,DFNB59,COCH |
| progressive hearing loss | progressive hearing loss///progressive hearing loss, autosomal recessive | AK097779,DFNB59,COCH |
| psoriasiform dermatitis, microcephaly & developmental delay | psoriasis///psoriasis vulgaris///psoriasis, association with///psoriasis, increased risk, association with///psoriasis, juvenile onset, association with///psoriasis, susceptibility, association with///psoriatic arthritis, protection against, assoc. with | IL20RA,LPIN2,PSORS1C1,SLC9A3R1,TBCD,LCE3B,MGST2,IL-23R,TNF,IL23R,CDSN,VEGFA,VEGF41,FLG |

FIG. 27R

| | | |
|---|---|---|
| retinitis pigmentosa, autosomal dominant | retinal pigmentosa///retinitis pigmentosa, juvenile///retinitis pigmentosa///retinitis pigmentosa / leber congenital amaurosis///retinitis pigmentosa & cone-rod dystrophy///retinitis pigmentosa & nanophthalmos///retinitis pigmentosa & retinal telangiectasia///retinitis pigmentosa 12///retinitis pigmentosa, association with///retinitis pigmentosa, atypical///retinitis pigmentosa, autosomal dominant///retinitis pigmentosa, isolated///retinitis pigmentosa juvenile-onset///retinitis pigmentosa, mild & deafness///retinitis pigmentossa, nonsyndromic///retinitis pigmentosa, recessive, no hearing loss///retinitis pigmentosa, x-linked///retinitis pigmentosa~berson~iovs | RGR,MERTK,USH2A,RLBP1,RPE65,CRX,ARL6,DKFZp43 4K1118,PRPF8,RP9,PRP3,SEMA4A,PRPF3,PRCD,TOPO RS,SNRNP200,IDH3B,RPGR,CNGB1,PRPF31,TULP1,DK FZp564F2122,IMPDH1,C2orf71,CERKL,BC020343.PRP H2,RPGRIP1,LRAT,SAG,RP1,USH3A,RP2,GUCY2D,RDH 12,ROM1,ABCA4 variant protein, CRB1,VMD2,PRKCG,TTC8,KLHL7,RBP3,CYGB PROM1,MYO7A,BC041434,CNGA1,GUCA1A,NRL,CA4 ,PDE6B,ABCA4,PDE6A,DQ266889,RHO,BEST1,CLRN1 SPATA7,KIAA0788,GUCA1B |
| retinitis pigmentosa, autosomal recessive | retinitis pigmentosa///retinitis pigmentosa, juvenile///retinitis pigmentosa /leber congenital amaurosis///retinitis pigmentosa & cone-rod dystrophy///retinitis pigmentosa & nanophthalmos///retinitis pigmentosa & retinal telangiectasia///retinitis pigmentosa 12///retinitis pigmentosa, association with///retinitis pigmentosa, atypical///retinitis pigmentosa, autosomal dominant///retinitis pigmentosa, autosomal recessive///retinitispigmentosa, isolated///retinitis pigmentosa, juvenile-onset///retinitis pigmentosa, mild & deafness///retinitis pigmentosa, nonsyndromic///retinitis pigmentosa, recessive, no hearing loss///retinitis pigmentosa,x-linked///retinitis pigmentosa~berson~iovs | RGR,PROM1,USH2A,RLBP1,RPE65,CRX,ARL6,PRPH2,P RPF8,PRP3,CA4,SEMA4A,PRPF3,ABCA4 variant protein, TOPORS,SNRNP200,IDH3B,RPGR,CNGB1,PRP F31,TULP1,DKFZp564F2122,IMPDH1,C2orf71,CERKL, PDE6A,DKFZp434K1118,RPGRIP1,LRAT,SAG,RP1,USH 3A,RP2,GUCY2D,RHO,ROM1,RP9,CRB1,VMD2,PRKCG ,TTC8,KLHL7,RBP3,CYGB,MERTK,MYO7A,BC041434,I MPG2,CNGA1,SPATA7,NRL,PRCD,PDE6B,ABCA4,BC02 0343,DQ266889,RDH12,BEST1,CLRN1,GUCA1A,KIAA 0788,GUCA1B |
| rheumatoid arthritis, susceptibility, association | rheumatoid arthritis and recurrent fever///rheumatoid arthritis, association with///rheumatoid arthritis, association with~kirsten~art///rheumatoid arthritis, association with ~suzuki~nat genet///rheumatoid arthritis, earlier onset, association with///rheumatoid arthritis, increased risk, association with///rheumatoid arthritis,juvenile, association with///rheumatoid arthritis, shorter duration, association with///rheumatoid arthritis, susceptibility, association | PTPN22,TAPBP,NR3C1,TAP2,AIRE,NLRP3,OCTN1,NFK BIA,TNFSF11,RSBN1,CD244,ZFP36,RUNX1,IL3,NFKBIL 1,AML1/AMP19 fusion,IL1A,SLC22A4,HAVCR1,MICA |

FIG. 27S

| | | |
|---|---|---|
| schizophrenia | schizophrenia///schizophrenia, assoc. with///schizophrenia, assoc. with~yamada~pnas///schizophrenia, association with///schizophrenia, association with~egan~pnas///schizophrenia, childhood onset///schizophrenia, childhood onset and autism spectrum disorders///schizophrenia, episodic, association///schizophrenia, familial, association with///schizophrenia, increased risk, association with///schizophrenia, modifier, assos. with///schizophrenia, risk, association with///schizophrenia, severe, increased risk, association | SLC6A3,OPRS1,PI4KA,LIM,AX747519,AKT,KIF17,CHI3LI,PAH,GAD1,PRNP,KIAA0457,ACAT2,RELN,PCM1,HTR2A,PIP4K2A,NTF3,LAMA5,ARVCF,MECP2,COMT,SR R,IMPA2,HRG,ADAM7,SYNGR1,PENK,APP,GRIK3,CCKAR,TCP1,BC037167,NPY,HTR3A,SIGMAR1,HTR5A,PDLIM5,KALRN,CHGB,KIAA1405,SYNGR1C,DKK2,CHL1,BC045795,BC012200,dickkopf-2,KIAA1973,SMARCA2,TFAP2A,EGR3,OPHN1,GRIN3A,DISC1,DISC2,HRH2,NRG1,GRM7,NOS1AP,DAOA,GRM3,NOS1,DPYSL2,TNR,NR4A2,DDR1variant protein,G72,SHANK3,MAP3K7IP1,NOTCH4,ZDHHC8,CALR,DDR1,DRD2,DRD1,GRIN2B,UPF3B,MLC1,SLC18A1,SYN3 |
| scott syndrome | scott syndrome | ABCAa1 |
| seckel syndrome | seckel syndrome | CPAP,KIAA0402,CEP152,PCNT,CENPJ |
| sensorineural hearing loss | hypopituitarism and sensorineural loss///optic atrophy & sensorineural hearing loss///sensorineural hearing loss///sensorineural hearing loss, bilateral///sensorineural hearing loss, nonsyndromic | LHX3,POU3F4,MYO1F,GJB2,MYO1C,MYO1F variant protein, WFS1,TCF21 |
| sensory neuropathy with dementia & hearing loss | sensorimotor neuropathy with ataxia | IFRD1 |
| short qt syndrome | short qt syndrome | KvLQT1,KCNQ1,KCNJ2,KCNH2 |
| short rib-polydactyly syndrome | short rib-polydactyly syndrome///short rib-polydactyly sydrome, majewski type///short rib-polydactyly syndrome,type 3 | KIAA1374,DYNC2H1,1FT80 |
| short rib-polydactyly syndrome, majewski type | short rib-polydactyly syndrome///short rib-polydactyly sydrome, majewski type///short rib-polydactyly syndrome,type 3 | KIAA1374,DYNC2H1,1FT80 |

FIG. 27T

| | | |
|---|---|---|
| spastic paraparesis | spastic paraparesis///spastic paraplegia 2///spastic paraplegia 3///spastic paraplegia 31///spasctic paraplegia 5///spastic paraplegia with thin corpus callosum///spastic paraplegia,autosomal dominant///spastic paraplegia, autosomal recessive///spastic paraplegia, silver syndrome type | KIAA1563,RNASE4,KIAA0196,SPG7,NIPA1,ALS2,SLC3 3A1,L1CAM,PLP1,CYP7B1,ANG,ZFYVE27,ZFYVE26,SP AST,CMAR,KIF5A,RAB9-like,GJC2,FA2H,ATL1,KIAA1840,HSPD1,REEP1,SPG11, DKFZp547E092 |
| spermatogenic failure | spermatogenic failure///spermatogenic failure, association with | NLRP14,TAF7L,NR5A1 |
| spinocerebellar ataxia with pyschomotor retardation | spinocerebellar ataxia 13///spinocerebellar ataxia 14///spinocerebellar ataxia 14~verbeek~brain///spinocerebellar ataxia 15///spinocerebellar ataxia 16///spinocerebellar ataxia 28///spinocerebellar ataxia 6///spinocerebellar ataxia type 5///spinocerebellar ataxia with axonal neuropathy | AFG3LC,CNTN4,KCNC3,CACNA1A,ITPR1,SPTBN2,PRK CG,TDP1 |
| systemic lupus erythematosus, association with | systemic lupus erythematosus, association with///systemic lupus erythematosus///systemic lupus eryhtematosus assoc. with///systemic lupus erythematosus, association with///systemic lupus erythematosus, increased risk, association with///systemic lupus erythematosus, male, association with///systemic lupus erythematosus, reduced risk, assoc.///systemic lupus erythematosus, risk, assoc. with///systemic lupus erythematosus, suspect., assoc.///systemic lupus erythematosus, susceptibility to, association///systemic lupus erythematosus, suspect. assoc. with | ACTA2,CRP,MFGE8,CDKN1A,DKFZp686M1886,CD226 ,TYK2,TNPO3,LOC541472,EGR2,CIITA,TREX1,TLR7,DN ASE1,ETS1,NFKBIL1,PDCD1,CTLA4,NR3C1,TRN-SR,FAS/ER,FCGR3A,FCGR2B,FCGR2C,TRIM21,MHC2T A,FASLG,BLK,LTK,ITPR3,KIAA1607,IL18,AK096314,TN FRSF1B,IRF5,NKG2-D,KLRK1,ESR1,TNFAIP3,WDFY4,ITGAM,FAS,TNFRSF1 A |
| systemic lupus erythematosus, increased risk, association with | systemic lupus ertematosus, association with///systemic lupus erhtematosus///systemic lupus eryhtematosus assoc. with///systemic lupus erythematosus, association with///systemic lupus erythematosus, increased risk, association with///systemic lupus erythematosus, male, association with///systemic lupus erythematosus, risk, assoc. with///systemic lupus erythematosus, susceptibility to, association///systemic erythematosus, susceptibility to, association///systemic lupus erythematosus, susept. assoc. with | ACTA2,CRP,MFGE8,CDKN1A,DKFZp686M1886,CD226 ,TYK2,TNPO3,LOC541472,EGR2,CIITA,TREX1,TLR7,DN ASE1,ETS1,NFKBIL1,PDCD1,CTLA4,NR3C1,TRN-SR,FAS/ER,FCGR3A,FCGR2B,FCGR2C,TRIM21,MHC2T A,FASLG,BLK,LTK,ITPR3,KIAA1607,IL18,AK096314,TN FRSF1B,IRF5,NKG2-D,KLRK1,ESR1,TNFAIP3,WDFY4,ITGAM,FAS,TNFRSF1 A |

FIG. 27U

| | | |
|---|---|---|
| tuberculosis, susceptibility to, association with | tuberculosis caused by m. tuberculosis, prot. against assoc.///tuberculosis, assoc. with///tuberculosis, association with///tuberculosis, reduced susceptibility, association with///tuberculosis, susceptibility to, association with///tuberculosis, susceptibility to, association with~tosh~pnas | TNFRSF1B,IL12RB1,MC3R,CD209,SFTPA2B,TLR6,SP11 0,IRGM |
| van der woude syndrome | van der woude syndrome///vander woude syndrome with bilateral conical elevations | IRF6 |
| venous thrombosis, reduced risk, association | venous thromboembolic disease///venous thromboembolism///venous thromboembolism, assoc. with///venous thromboembolism, prot. against, in caucasians, assoc. with///venous thromboembolism, suscep., association with///venous thrombosis, increased risk, association | SERPINE1,SERPINA10,KNG1,TNFSF4,FGA,FGB,PROCR |
| waardenburg anophthalmia syndrome | waardenburg syndrome///waardenburg syndrome 2///waardenburg syndrome 2a///waardenburg syndrome 4///waardenburg syndrome i///waardenburg syndrome iii | SOX10,POLR2F,CCDC140,PAX3,MITF,EDN3 |
| warburg micro syndrome | warburg micro syndrome 1 | DKFZp434A012,RAB3GAP1 |
| x-chromosomal hearing loss | x-linked deafness | POU3F4 |
| zellweger syndrome g | zellweger syndrome///zellweger syndrome c///zellweger syndrome h///zellweger syndrome, complementation group d | PEX1,TUBA8,PEX26,PEX6,PEX14,Em:AC008101.5,PEX 10,ABCD3,PXMP3,Pex14,PEX13,PEX16 |
| zellweger syndrome complementation group | zellweger syndrome///zellweger syndrome c///zellweger syndrome h///zellweger syndrome, complementation group d | PEX1,TUBA8,PEX26,PEX6,PEX14,Em:AC008101.5,PEX 10,ABCD3,PXMP3,Pex14,PEX13,PEX16 |

FIG. 27V

| Populations | Total Variants | dbsnp135 Filter | 1000 Genomes filter | CGI Filter | w/0 Functional Filter | w/Functional Filter |
|---|---|---|---|---|---|---|
| CEU | 3879980 | 2362861 | 490537 | 55210 | 235 | 31 |
| CEU | 3798634 | 2309390 | 462832 | 50116 | 165 | 17 |
| CEU | 3759176 | 2279299 | 440280 | 45992 | 175 | 16 |
| CEU | 3904906 | 2377396 | 502081 | 44497 | 131 | 18 |
| CEU | 3882105 | 2368009 | 485353 | 57258 | 192 | 22 |
| CEU | 3830403 | 2326231 | 470303 | 21148 | 85 | 25 |
| CEU | 3904269 | 2378824 | 499865 | 24915 | 86 | 20 |
| CEU | 3909320 | 2382700 | 501124 | 22327 | 68 | 17 |
| CEU | 3901545 | 2382175 | 492540 | 21742 | 75 | 13 |
| CEU | 3888670 | 2373279 | 484246 | 22284 | 77 | 18 |
| CEU | 3898677 | 2367256 | 498677 | 22069 | 65 | 16 |
| CEU | 3883072 | 2355272 | 492106 | 19553 | 67 | 14 |
| CEU | 3822445 | 2311291 | 466242 | 19404 | 61 | 13 |
| CEU | 3801784 | 2307883 | 452191 | 22134 | 45 | 16 |
| CEU | 3747040 | 2265462 | 436431 | 21298 | 50 | 11 |
| CEU | 3762638 | 2274948 | 427749 | 22349 | 80 | 21 |
| CEU | 3866738 | 2347888 | 482518 | 17752 | 47 | 10 |
| CEU | 3643266 | 2186773 | 410787 | 35451 | 98 | 18 |
| CEU | 3906044 | 2394376 | 496097 | 40367 | 135 | 17 |
| CEU | 3879467 | 2349511 | 496182 | 27862 | 91 | 17 |
| CEU | 3827308 | 2327433 | 478161 | 27895 | 52 | 8 |
| CEU | 3894582 | 2368961 | 493128 | 22229 | 80 | 17 |
| YRI | 4707812 | 2873916 | 620056 | 103595 | 294 | 25 |
| YRI | 4792325 | 2954227 | 645330 | 99394 | 297 | 38 |
| YRI | 4763674 | 2921412 | 662523 | 110334 | 359 | 34 |
| YRI | 4820703 | 2961108 | 656196 | 99320 | 250 | 31 |
| YRI | 4753535 | 2914787 | 618996 | 99573 | 270 | 31 |
| YRI | 4772444 | 2934894 | 640987 | 96936 | 255 | 21 |
| CHB | 3919017 | 2393143 | 515871 | 73740 | 364 | 26 |
| CHB | 3946858 | 2413368 | 528095 | 73740 | 357 | 28 |
| CHB | 3957899 | 2422188 | 530910 | 68241 | 235 | 17 |
| CHB | 3916917 | 2386078 | 526381 | 71943 | 310 | 37 |
| JPT | 3922671 | 2388283 | 516963 | 64600 | 271 | 29 |
| JPT | 3903369 | 2380092 | 496663 | 62794 | 226 | 22 |
| JPT | 3926823 | 2403071 | 499269 | 58257 | 226 | 19 |
| JPT | 3872869 | 2355966 | 475418 | 47327 | 125 | 16 |
| LWK | 4553518 | 2784479 | 565745 | 128347 | 443 | 37 |
| LWK | 4554038 | 2770737 | 569016 | 128723 | 437 | 32 |
| LWK | 4497807 | 2735774 | 555488 | 125217 | 444 | 28 |
| LWK | 4505909 | 2740453 | 550359 | 121279 | 422 | 32 |
| YRI | 4766391 | 2927226 | 627720 | 89954 | 187 | 27 |

FIG. 28A

| Populations | Total Variants | dbsnp135 Filter | 1000 Genomes filter | CGI Filter | w/0 Functional Filter | w/Functional Filter |
|---|---|---|---|---|---|---|
| YRI | 4488890 | 2727239 | 533010 | 65146 | 170 | 22 |
| YRI | 4652456 | 2828737 | 597593 | 67991 | 192 | 26 |
| YRI | 4589624 | 2785974 | 553186 | 31021 | 36 | 10 |
| MEX | 3748580 | 2274366 | 427108 | 53746 | 214 | 16 |
| MEX | 3736098 | 2257580 | 424743 | 63511 | 280 | 27 |
| MEX | 3799508 | 2288880 | 442906 | 67423 | 282 | 23 |
| MEX | 3686483 | 2219047 | 410075 | 66528 | 275 | 31 |
| ASW | 4468727 | 2711275 | 514052 | 81204 | 251 | 30 |
| ASW | 4390274 | 2679224 | 488117 | 84222 | 252 | 27 |
| ASW | 4470591 | 2705207 | 519829 | 90279 | 309 | 33 |
| ASW | 4638092 | 2835559 | 574708 | 96497 | 356 | 35 |
| MEX | 3862271 | 2356099 | 508725 | 67653 | 380 | 39 |
| ASW | 4639444 | 2842882 | 598253 | 80416 | 188 | 39 |
| TSI | 3849430 | 2346677 | 467769 | 53732 | 203 | 30 |
| TSI | 3891901 | 2370364 | 502863 | 65918 | 315 | 35 |
| TSI | 3893806 | 2365087 | 490905 | 56988 | 250 | 27 |
| TSI | 3897496 | 2376425 | 509935 | 69172 | 297 | 32 |
| GIH | 4024392 | 2474799 | 572571 | 109919 | 470 | 42 |
| GIH | 3948900 | 2428008 | 557264 | 110994 | 551 | 33 |
| GIH | 4013347 | 2478349 | 575614 | 117753 | 573 | 31 |
| GIH | 3935601 | 2419731 | 546119 | 100844 | 482 | 29 |
| MEK | 4523822 | 2779646 | 642316 | 96803 | 321 | 27 |
| MEK | 4603747 | 2853389 | 673711 | 173293 | 648 | 36 |
| MEK | 4510839 | 2771192 | 643601 | 100239 | 321 | 25 |
| MEK | 4601949 | 2848595 | 659648 | 169650 | 647 | 46 |
| PUR | 3885088 | 2356683 | 476469 | 45150 | 183 | 27 |
| PUR | 3896958 | 2357620 | 466180 | 44525 | 161 | 23 |
| PUR | 3766830 | 2279619 | 422432 | 23129 | 58 | 19 |

FIG. 28B

SYSTEMS AND METHODS FOR GENOMIC ANNOTATION AND DISTRIBUTED VARIANT INTERPRETATION

CROSS-REFERENCE TO RELATED APPLICATIONS

This application is a continuation-in-part of PCT/US2012/062787, filed Oct. 31, 2012 and claims priority under 35 U.S.C. 119(e) to U.S. Provisional Patent Application No. 61/553,576, filed Oct. 31, 2011; No. 61/676,855, filed Jul. 27, 2012, and No. 61/852,255, filed Mar. 15, 2013. The disclosures of each of these applications are hereby incorporated by reference in their entireties.

BACKGROUND

1. Technical Field

The present invention relates to DNA sequencing and more particularly to interpretation of the many genetic variants generated in any sequencing project.

An automated computational system for producing known and predicted information about genetic variants, otherwise known as variant annotations, is also described.

2. Related Art

Advances in high-throughput DNA sequencing technologies have enabled the identification of millions of genetic variants in an individual human genome. Reductions in sequencing costs and increases in sequencing efficiency have brought these capabilities within the grasp of individual laboratories looking to use DNA sequencing as a powerful tool in their research endeavors, yet very few laboratories have the computational expertise and infrastructure to make sense of the genetic variants identified through these studies. While increasingly sophisticated tools continue to be developed for sequence assembly and variant calling, interpretation of the massive number of genetic variants generated by any sequencing project remains a major challenge. This problem is especially pronounced in the interpretation of noncoding variants that likely explain a major proportion of heritability in common complex diseases. Because of the extreme difficulty and computational burden associated with interpreting regulatory variants and variations across collections of genes, genome sequencing studies have focused on the analysis of non-synonymous coding variants in single genes. This strategy has been effective in identifying mutations associated with rare and severe familial disorders; however, analysis of types of variants must be made accessible to the research community in order to address the locus and allelic heterogeneity that almost certainly underlies most common disease predisposition.

The availability of high-throughput DNA sequencing technologies has enabled nearly comprehensive investigations into the number and types of sequence variants possessed by individuals in different populations and with different diseases. For example, not only is it now possible to sequence a large number of genes in hundreds if not thousands of people, but it is also possible to sequence entire individual human genomes in the pursuit of inherited disease-causing variants or somatic cancer-causing variants. Whole genome sequencing as a relatively routine procedure may lie in the near future as high-throughput sequencing costs and efficiency continue to improve. In fact, as costs continue to decline, high-throughput sequencing is expected to become a commonly used tool, not only in human phenotype based sequencing projects, but also as an effective tool in forward genetics applications in model organisms, and for the diagnosis of diseases previously considered to be idiopathic, for which there are already some striking examples.

One particularly vexing problem that has accompanied the development and application of high-throughput sequencing is making sense of the millions of variants identified per genome. Recent successes at identifying variants associated with disease have generally been executed under clever yet restricted conditions. For example, a number of re-sequencing studies have focused on the identification of causal variants at significant genome-wide association study (GWAS) loci and have identified excesses of non-synonymous variants in nearby candidate genes. However, these potentially causal variants tend not to explain much more of the heritability than the GWAS tag SNP itself, a large proportion (~80%) of GWAS hits are in intergenic regions with no protein-coding elements nearby, and, even with extremely large study populations, the GWAS strategy is not likely to individually identify tag-SNPs that explain even half the heritability of common diseases.

Nevertheless, GWAS has plenty left to offer in terms of identification of significant, or at least suspicious, candidate loci for re-sequencing studies. Other sequencing strategies have successfully identified non-synonymous variants associated with familial and/or severe disorders. However, if highly penetrant variants contribute to common disease predisposition, they should be detectable by linkage analysis. Linkage and straightforward association strategies have not identified the majority of variants predisposing to common diseases where variable penetrance, allelic and locus heterogeneity, epistasis, gene-gene interactions, and regulatory variation play a more important yet elusive role. If sequence-based association studies are to successfully identify variants associated with common diseases and expand our understanding of the heritable factors involved in disease predisposition, investigators must be armed with the tools necessary for identification of moderately penetrant disease causing variants, outside of GWAS hits, and beyond simple protein coding changes. In fact, the identification and interpretation of variants associated with inherited but not strongly familial disease, is a crucial step in translating sequencing efforts into a truly significant impact on public health.

If one accepts the rare variant hypothesis of disease predisposition, then one would expect rare variants predisposing to disease will be associated with high relative risk, but because of their low frequency, simple univariate analyses where each variant is tested for association with disease will require extremely large sample sizes to achieve sufficient power. This problem is compounded tremendously if disease predisposition results from the interaction and combination of extremely rare variants segregating and encountering one another throughout the population. Variant collapsing strategies have been shown to be a powerful approach to rare variant analysis; however, collapsing methods are extremely sensitive to the inclusion of noncausal variants within collapsed sets.

The key to unlocking the power of variant collapsing methods, and facilitating sequence based disease association studies in reasonable study sizes and at reasonable cost, is a logical approach to forming collapsed sets. In fact, regardless of the allelic frequency and penetrance landscape underlying common disease predisposing variants, set based analyses can expose what simple linkage or association studies have failed to reveal.

Recent successes in clinical genome sequencing, especially in family-based studies of individual with rare, severe and likely single-gene disorders, have highlighted the potential for genome sequencing to greatly improve molecular diagnosis and clinical decision making. However, these successes have relied on large bioinformatics teams and in-depth literatures surveys, an approach it is neither scalable nor rapid. The adoption of genome sequencing among the clinical community at large requires, among other things, the ability to rapidly identify a small set of candidate disease-causing (i.e., likely pathogenic) mutations from among the tens to hundreds of genes harboring variants consistent with plausible functional effects, inheritance patterns and population frequencies. Presented herein is a framework for the identification of rare disease-causing mutations, with a focus on phenotype-informed network raking (PIN Rank) algorithm for ordering candidate disease-causing mutations identified from genome sequencing. Our proposed algorithm's accuracy in prioritizing variations is demonstrated by applying it to a number of test cases in which the true causative variant is known.

SUMMARY

Systems and methods that make variant interpretation as accessible as variant-generation from high-throughput DNA sequencing is described herein.

In one embodiment the present invention provides a computer-based genomic annotation system. The system includes a database configured to store genomic data, non-transitory memory configured to store instructions, and at least one processor coupled with the memory, the processor configured to implement the instructions in order to implement an annotation pipeline and at least one module for filtering or analysis of genomic data.

In another embodiment the invention provides a computer-based method for predicting a risk of an individual developing a disease. The method includes the steps of: obtaining genetic variant data describing a plurality of genetic variants in a genome of the individual, the genome including a plurality of genes; using a microprocessor, determining a percent functionality for each gene based on the genetic variant data; using a microprocessor, generating a weighted genetic network including the plurality of genes of the genome having weighted connections therebetween; using a microprocessor, obtaining a global centrality score for each of the plurality of genes in the weighted genetic network; using a microprocessor, generating a weighted genetic disease network including a plurality of genes having weighted connections therebetween; assigning a high importance score in the weighted genetic disease network for at least one gene that is associated with the disease; using a microprocessor, obtaining a disease-specific centrality score for each of the plurality of genes in the weighted genetic disease network; for each of the plurality of genes, determining, using a microprocessor, a difference between the global centrality score for the gene and the disease-specific centrality score for the gene and multiplying the difference by the percent functionality for the gene to produce a product for each gene; using a microprocessor, summing the products of the genes to produce a disease score for the individual; and predicting a risk of developing a disease for the individual based at least in part on the disease score.

Other aspects of the invention will become apparent by consideration of the detailed description and accompanying drawings.

BRIEF DESCRIPTION OF THE DRAWINGS

Features, aspects, and embodiments are described in conjunction with the attached drawings, in which:

FIG. 4 is a diagram illustrating four levels of annotation that can be performed by the annotation pipeline of FIG. 2.

FIG. 11A shows the correlation between median ranks and degree centrality of diseased gene without functional filters (p-value=0.0084, r2=0.051).

FIG. 11B shows the correlation between median ranks and degree centrality of diseased gene with functional filters (p-value=0.0577, r2=0.0397).

FIG. 11C shows the correlation between median ranks and betweenness centrality of diseased gene without functional filters (p-value=0.0492, r2=0.0245).

FIG. 11D shows the correlation between median ranks and betweenness centrality of diseased gene with functional filters (p-value=0.5626, r2=−0.01).

FIG. 14 is a heatmap displaying the proportion of disease genes captured within the top three ranks using functional filters and the PIN Rank algorithm with different combinations of alpha values and scale factors. In this analysis, scale factors between 1-5 and alpha values between 0.01-0.99 were compared, and it was determined that the best results were produced when using a scale factor of three and alpha value of 0.95, to capture 57.99% of disease genes.

FIG. 15C suggests that African genomes possess ~6,000,000 loci that harbor derived alleles whereas non-African genomes possess ~350,000 less. This suggests that there are a great number of non-fixed derived variants in different human populations (i.e., variant sites for which ancestral and derived alleles are segregating in the human population at large). FIG. 15D suggests that the number of loci that harbor probably damaging derived ns cSNVs is ~2850 in African genomes and ~250 less in non-African genomes.

FIGS. 16 A-D provide a graphical display of the results of a test for differences in the frequency and per-genome rate of functional derived homozygous genotypes across the populations. FIG. 16A suggests that there is greater number of homozygous loci with derived alleles in non-African populations. FIG. 16B suggests that there are a greater number of homozygous loci with probably damaging (PD) derived allele ns cSNVs in non-African populations as well. FIG. 16C and FIG. 16D suggest that there are a greater number of homozygous loci with likely functional derived alleles of any type and ultimately a greater rate of homozygous loci with likely functional derived alleles across entire individual genomes, respectively.

FIG. 18A provides multidimensional scaling plots of the 54 unrelated individuals with complete genome data. The 54 individuals (black dots) overlaid on 4,213 individuals of known ancestry based on 16,411 ancestry informative markers. The individuals with known ancestries were obtained from public repositories and are coded by continent with shading indicating subpopulations within those continents (Europeans; Yorubans; East Asians; Native Americans; Central Asians; African Americans).

FIG. 18B provides multidimensional scaling plots of the 54 unrelated individuals with complete individual genomes in FIG. 18A without the overlay of other individuals. Color coding for these 54 individuals based on their known ancestries is provide in the inset.

FIG. 21 (Table 1) provides the regression analysis results comparing the frequency and rates of variant types per individual genome across 10 global populations. Note that YR (Yourban) sample was taken as the reference. Y-int=y-intercept; R-Sqr=Fraction of Variation in the Variant type explained by the regression model. Bolded entries=p-value less than 0.05; Italicized entries=p-value less than 0.0005.

FIG. 22 (Table 2) provides a pairwise population comparisons using Turkey's HSD method for the number of derived genotypes per individual genome (below diagonal) and number of functional homozygous derived genotypes (above diagonal). Entries reflect the average differences with the populations listed in the second through eleventh columns subtracted from the populations listed in the first column. Bolded entries=p-value less that 0.05; Bolded and Italicized entries—p-value less than 0.0005.

FIG. 23 (Table 3) provides the frequency and rates (×10000) of population-specific variant types for African (AFR), European (EUR), and Asian (ASN) populations.

FIG. 24 (Table 4) provides the number of ns cSNVs deemed 'novel' with predicted functional consequence scores greater than that assigned to a known CMT syndrome-inducing variant as a function of the reference panel used for five individual genomes of diverse ancestry. The numerator in each cell entry provides the number of ns cSNVs with functional consequence scores greater than the average of (N=506) known CMT mutations that would be deemed novel on the basis of the different reference panels associated with each column of the table for the individuals" whole genome variant lists denoted in the 'Indiv' column. The denominator provides the total number of ns cSNVs on each individual's ('Indiv') genome with scores higher than the CMT mutation.

FIGS. 25A-D (Table 5) provides PIN Rank results using fold change scoring method for disease-causing variants in 69 Complete Genomics genomes after population based filtering only.

FIGS. 26A-C (Table 6) provides the PIN Rank results using fold change scoring method for disease-causing variants in 69 Complete Genomics genomes after population-based and functional filtering.

FIGS. 27A-V (Table 7) provides a list of test disease and complementary entries that were selected to create seed lists.

FIG. 28A-B (Table 8) illustrates that in the post population-based and annotation-based filtration, an average of 240 and 25 variants passed the filtration scheme per genome, respectively, with a range of 36-648 and 8-46 variants per genome.

DETAILED DESCRIPTION

The systems and methods described herein comprise an annotation system that includes tools, algorithms, and report functions configured to perform holistic, in-depth, annotations and functional predictions on variants generated from high-throughput sequencing data in multiple arenas of genomic relevance, including coding and regulatory variants as well as the biological processes that connect them. Appropriate annotation of sequence variants is crucial in putting into perspective the overabundance of a particular variant or set of variants in diseased individuals or the belief that a particular variant is likely to have a molecular and/or biological effect. Due to the computational burden of variant annotation, both in terms of required computing power and storage of extremely large reference databases, the system can be implemented on a computational cluster. In certain aspects, access to the system can be through a web portal.

Figure 1:
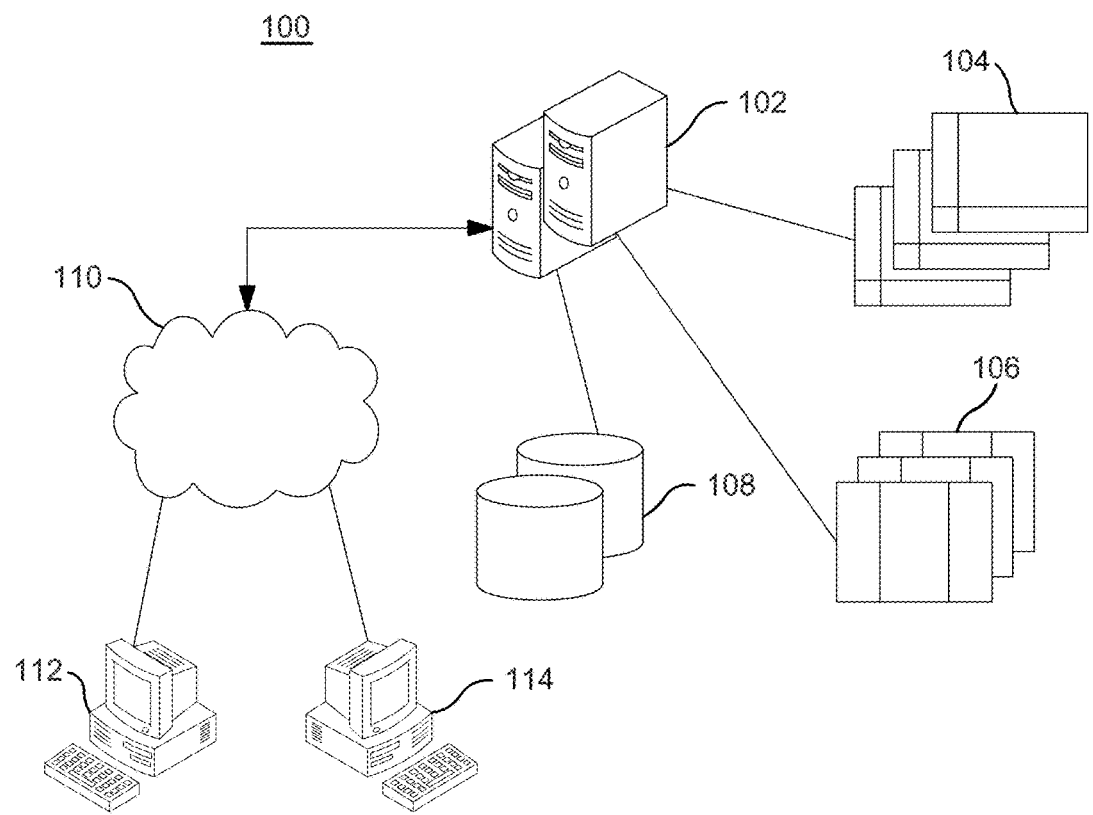
FIG. 1 is a block diagram illustrating an example genomic annotation system in accordance with one embodiment of the invention.

FIG. 1 is a diagram illustrating an example system 100 for performing genomic annotation and distributed variant interpretation in accordance with one example embodiment. As can be seen, system 100 comprises an annotation authority (102), which can comprise the hardware and software resources needed to perform the functions described herein. Thus authority (102) can comprise the servers, web servers, routers, processors, terminals, user interfaces, programs, API's, algorithms, etc., required for a particular implementation. It will be understood that the servers, routers, etc., needed for a particular implementation, can be located at a single location and even within a single device, or can be distributed across multiple locations, devices, or both. For example, as noted above, a particular implementation of the disclosed systems and methods can include a computational cluster.

Authority (102) can be interfaced with one or more databases (108) configured to store data, computations, reports, etc. Further, authority (102) can include or can be interfaced with storage and memory (not shown), at least some of which is not transitory, configured to store instructions, algorithms (104), programs, data, etc. Algorithms (104) can be configured to perform the computational analysis, trending, analytics, etc., as described herein, from which various reports (106) and analysis can be generated.

In certain embodiments, system 100 can be implemented as or include a web server that can be accessed via the internet (110) via a terminal (112) in order to perform the computational analysis described herein. Further, the annotation pipeline may utilize, as input, a list or file of variants where each variant can be identified according to information such as its genomic location such as by the chromosome with which the variant is associated, and the start and end positions of the variant, and the alleles of the variant. Variants can include any defined modification to a DNA sequence as compared to one or more other reference DNA sequences. Variants may involve any number of adjacent or spaced apart bases or series of bases, and may include single nucleotide substitutions, insertions, deletions, and block substitutions of nucleotides, structural variants, copy number variants, etc. The system 100 may in some implementations generate the list or file of variants directly from sequence information that is retrieved or may be generated by an automated sequencing machine associated with the system 100. Variants can be provided to system 100 in a number of ways, including via another terminal or system (112, 114).

Figure 2:
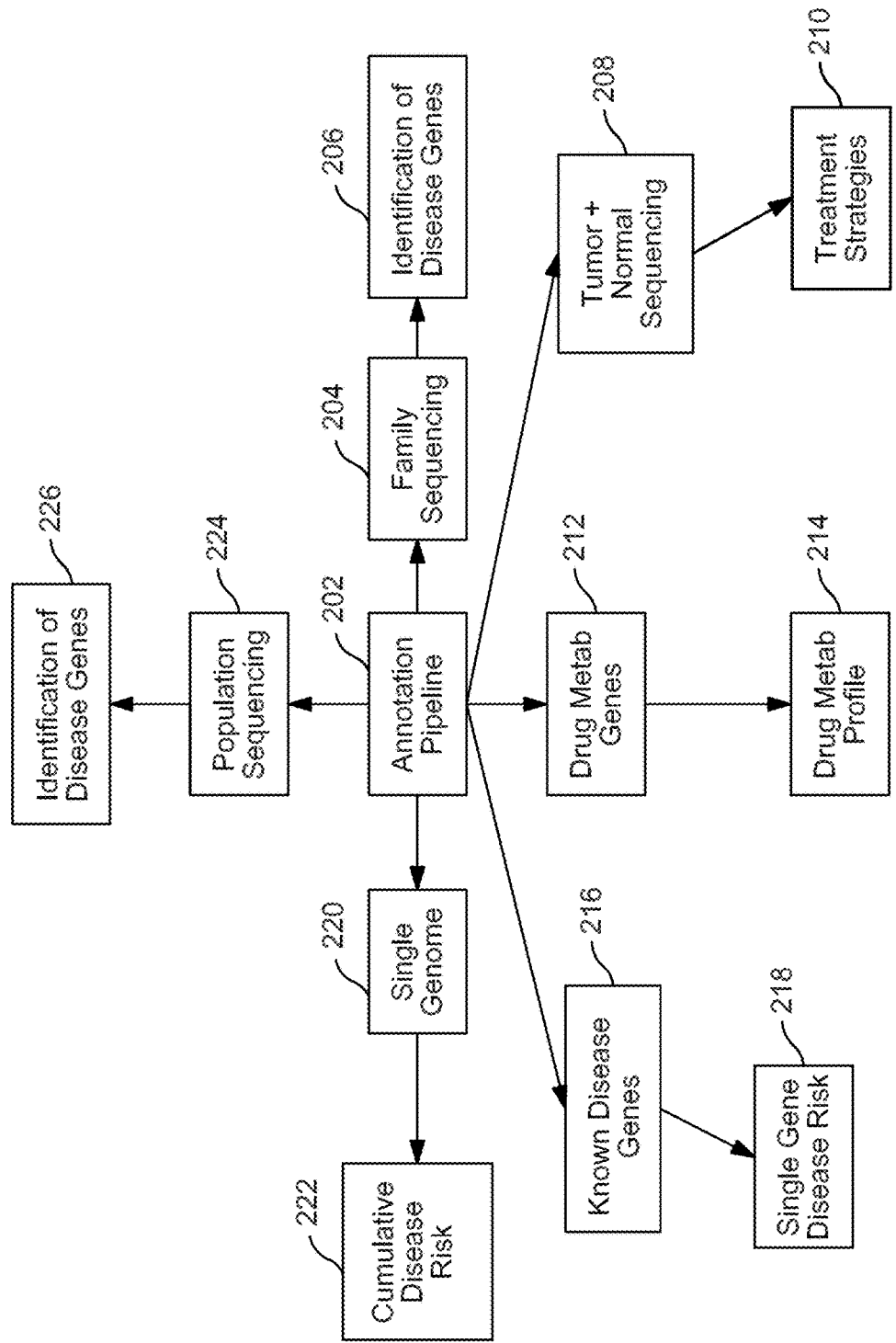
FIG. 2 is a block diagram illustrating example functional modules of the system of FIG. 1.

FIG. 2 is a diagram illustrating the functional modules of system 100, according to one embodiment and which can be implemented within system 100. At the center of these modules is annotation pipeline (202), which is described in more detail below. The function of the annotation pipeline is to take an input variant file comprising a list of variants found in a sequenced genome with basic identification information for each variant, and produce an output annotation file that contains most or all of the identification information from the variant file plus a plurality of additional annotation entries associated with each variant of the input variant file that may be retrieved from a variety of databases having clinical or other information about known variants and/or may be calculated from the nature of the variant and its location with respect to regulatory and/or transcribed regions of the genome. This annotation file or other outputs of annotation pipeline (202) can then be used for various analyses such as family sequencing (204), which can lead to the identification of disease genes (206) based on the family sequencing (204); tumor and normal sequencing (208), which can lead to treatment strategies (210); identification of drug metabolism genes (212), which can lead to a drug metabolism profile (214); known disease genes (216), which can lead to identification of single gene disease risk (218); single genome analysis (220), which can lead to a cumulative disease risk for that genome (222); and population sequencing (224), which can lead to identification of disease genes (226) based on the population sequencing (224).

Annotation pipeline (202) can include at least the annotations illustrated in FIG. 4. Thus, annotation pipeline (202) can include four major levels of annotation: genomic elements, prediction of impact, linking elements, and prior knowledge.

Figure 3:
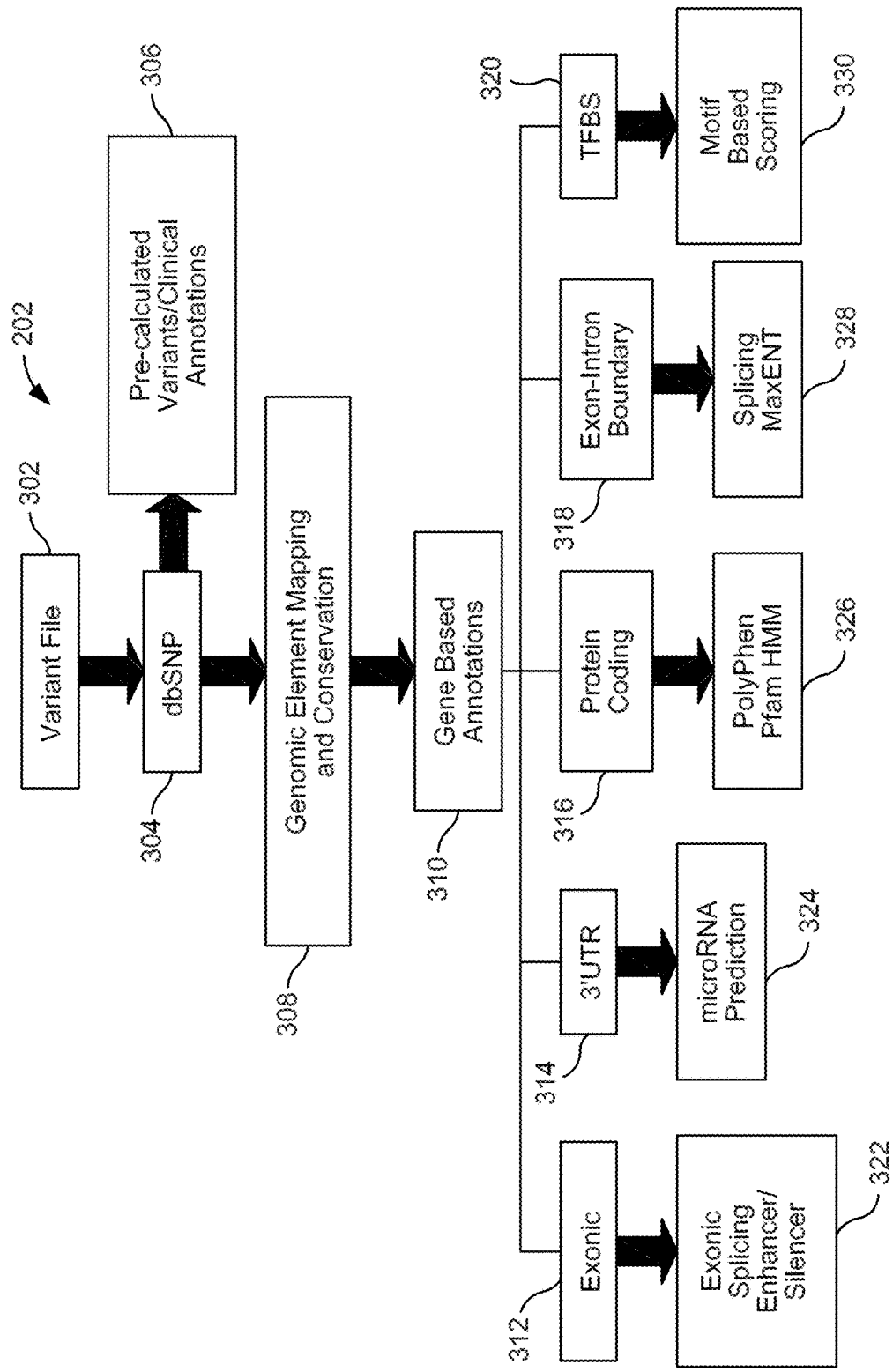
FIG. 3 is a flow chart illustrating the process flow of an example annotation pipeline that can be included in the system of FIG. 1 in accordance with one embodiment.

FIG. 3 is a diagram illustrating an example annotation pipeline workflow in accordance with one embodiment. First, as mentioned above, the annotation pipeline (202) can receive as an input a variant file in step (302) that includes a list of identifying information for each variant, including the chromosome with which the variant is associated, the start and end positions of the variant, and the alleles of the variant. The systems and methods herein are especially applicable to variant files derived from whole genome sequences, which for the human genome is about 3 billion base pairs (and which may or may not include mitochondrial DNA sequence), and which will produce a variant file with identifying information for usually at least hundreds of thousands, and more likely millions of variants. Annotation pipeline (202) can be configured to then analyze the type of variant, which can include single nucleotide substitution variants, insertions, deletions, and block substitutions. Variant types can be associated with the annotations/predictions, with the exception of PolyPhen-2 predictions, which are only applied to nonsynonymous single nucleotide variants.

The variants within the variant file (302) can then be associated with common polymorphisms deposited in The Single Nucleotide Polymorphism Database (dbSNP) in step 304. The dbSNP is a free public archive for genetic variation within and across different species developed and hosted by the National Center for Biotechnology Information (NCBI) in collaboration with the National Human Genome Research Institute (NHGRI). In addition to single nucleotide polymorphisms (SNPs), dbSNP also includes other types of variants or polymorphisms such as short deletion and insertion polymorphisms (indels/DIPs), multinucleotide polymorphisms (MNPs), heterozygous sequences, and named variants. The dbSNP accepts apparently neutral polymorphisms, polymorphisms corresponding to known phenotypes, and regions of no variation.

As of February 2010, dbSNP included over 184 million submissions representing more than 64 million distinct variants for 55 organisms, including *Homo sapiens, Mus musculus, Oryza sativa*, and many other species.

In system 100, annotations for dbSNP polymorphisms can be precomputed, e.g., using the systems and methods described herein. Thus, in step (306) in order to significantly speed up the annotation process, the variants in variant file (302) can be compared to precomputed variant annotation information. In some implementations, annotations for previously unobserved variants can be pre-computed. For example, all possible coding variants could be precomputed. The precomputed annotations may also, for example, have been previously computed during the process of annotating a variant file produced from a different individual's genome. These precomputed annotations can include functional element associations and impact predictions, to be described below, as well as clinical annotations for known phenotype associations, drug metabolism effects including clinical associations listed in The Pharmacogenomics Knowledge Base (PharmGKB), the Genome-Wide Association Studies (GWAS) catalog, and the National Institute of Health (NIH) Genetic Association Database, or both. In this implementation, the database 108 of FIG. 1 may store a collection of annotation sets, each associated with a variant that has previously been annotated with the process of FIG. 3. During future applications of the process of FIG. 3 to new variant files for new individual genomic sequences, the variants in each subsequently received variant file can be compared to the already annotated variants in the data base 108 to determine if any have been previously annotated. If matches are found, some or all annotations for the matched variant in the newly received variant file can be retrieved from the database, rather than generated again. As more variant files from more genomes are annotated with this process, the database 108 stores more annotated variants, which further reduces the time required to annotate later received variant files, because finding matches becomes more likely. To further this process, publicly available variant files for the increasingly large number of reference genomes that have been and will continue to be sequenced can be input to the system, annotated with the process of FIG. 3, and the results stored in the database 108 for reference in future variant annotation processes. The database 108 can also be updated or curated on a regular basis, wherein variants that have been previously annotated are re-annotated in whole or part so that the annotations reflect the latest information available about the variant.

In certain embodiments, annotations for variants not found in dbSNP can be computed de novo in an automated parallel computing environment as described below. For the tools described below, alternate tools and or extensions may be applied.

Genomic element mapping and conservation analysis can then occur in step (308). Annotation pipeline (202) can be configured to begin this step by mapping variants to a known gene from, e.g., the University of California, Santa Cruz (UCSC) Genome Browser known gene database. In advantageous implementations, every (or at least substantially every) variant in the variant file 302 is mapped to a gene, even if the location of a particular variant has no apparent connection to any expressed, regulatory, or other known functionally important portion of any known gene. Traditionally, variants are only mapped to a gene if they are found to overlap some functionally significant portion of the gene, often only exons. Although it has long been recognized that variants associated with regulatory or other functionally significant gene segments that are unrelated to the amino acid sequence of the associated transcript(s) can contribute to disease and other phenotypic manifestations, this fact has not been applied significantly to variant annotation, especially not in the whole genome context. Accordingly, the variants of the variant file can be associated with transcripts of the "nearest" gene (or perhaps more than one gene). The "nearest" gene can be defined in a variety of ways. In one implementation, the system may find the closest start or stop codon of a gene in a set of known genes (such as the set of known genes in the UCSC Genome Browser), and map the variant to the gene associated with the nearest stop or start codon. If the variant falls within a known gene, its position within gene elements (e.g. exons, introns, untranslated regions, etc.) can be recorded for future impact predictions depending on the impacted gene element. If the gene has multiple transcripts, impact information can be computed separately for each transcript. Furthermore, variants falling within an exon between the start and stop codons for the gene can be analyzed for their impact on the amino acid sequence (e.g. synonymous, nonsynonymous, nonsense, frameshift, in-frame, and intercodon). It will be appreciated, however, that a variant may not fall between a start and stop codon of any gene, may be in an intergenic region, and may in fact not be in a transcribed region of the genome at all. Even in this case, though, the system may map the variant to the gene having the closest stop or start codon. This has surprisingly been found quite useful because the functional effect of variants across the whole genome remains highly uncertain, and this allows previously unknown functional associations to be uncovered in a wide variety of applications. In some implementations, variants are mapped to genes based on considerations other than or in addition to small linear distance along the base sequence from the variant. As one example, rather than mapping to the gene that is the closest linear distance from the variant, one could map to a gene with an estimated small 3D distance in the chromosome. Experimental data providing 3D associations between different sections of the DNA sequence when in the chromosome is available, and could be leveraged to map some or all of the variants in a variant file to one or more genes. Any type of information that may indicate that the location of a variant could make the variant relevant to a known gene could be used to map a gene to the variant, whether statistical, regulatory, or related to physical interactions such as protein-protein interactions or DNA proximity interactions. Annotations mapping the variant to multiple different genes could be created, with different measures of gene to variant relevance being used for each mapping.

All variants can also be associated with conservation information in two ways. First, variants can be associated with conserved elements from the PhastCons conserved elements (28way, 44way, 28wayPlacental, 44wayPlacental, and 44wayPrimates). These conserved elements represent potential functional elements preserved across species. Conservation can also assessed at the specific nucleotide positions impacted by the variant using the phyloP method. The same conservation levels as PhastCons can be used in order to gain higher resolution into the potential functional importance of the specific nucleotide impacted by the variant.

Next, gene-based annotations can be produced in step (310) based on the gene(s) nearest to each variant. These annotations are relevant regardless of the specific gene element impacted by the variant. First, if the gene is associated with a phenotype in the Online Mendelian Inheritance in Man (OMIM) database, the OMIM identifier is reported. Other gene-based annotations that can be included are known associations with disease in the Human Gene Mutation Database (HGMD) or the GWAS catalog and known associations with drug metabolism in the Pharmacogenomics Knowledge Base (PharmGKB). Gene function can then be annotated in one of many ways. Certain examples include: (1) PFAM protein domains identified by InterProScan; (2) Gene Ontology Molecular Functions associated with those protein domains, and (3) Gene Ontology Biological Processes associated with the gene. These annotations provide higher level functional and biological categories that can be used to connect disparate variants with one another in set-based analyses.

Once the gene-based annotations are produced in step (310), various annotation processes can take place in parallel on all or some of the variants in order to provide annotation information that can then be synthesized and used by various other modules, e.g., depicted in FIG. 2. These synthesized annotations can also be used to update the pre-calculated annotations used in step (306).

For example, in step (320), variants, regardless of their genomic position, can be associated with predicted transcription factor binding sites (TFBS) and scored for their potential impact on transcription factor binding. In certain embodiments, predicted TFBS can be pre-computed by utilizing the human transcription factors listed in the JASPAR database and The Transcription Factor Database (TRANSFAC) transcription-factor binding profile to scan the human genome using the Metrics for Object-Oriented Design (MOODS) algorithm. The probability that a site corresponds to a TFBS is calculated by MOODS based on the background distribution of nucleotides in the human genome.

TFBS can be identified based on a relaxed threshold (p-value<0.0002) in conserved, hypersensitive, or promoter regions, and at a more stringent threshold (p-value<0.00001) for other locations in order to capture sites that are more likely to correspond to true functional TFBS. Conserved sites correspond to the phastCons conserved elements; hypersensitive sites correspond to Encode DNASE hypersensitive sites annotated in UCSC genome browser, while promoters correspond to regions annotated by TRANSPro, and 2 kb upstream of known gene transcription start sites, identified by SwitchGear Genomics ENCODE tracks. The potential impact of variants on TFBS can be scored in step (330) by calculating the difference between the mutant and wild-type sequence scores using the position weighted matrix method described in 16(1):16-23, incorporated herein by reference) and shown to identify regulatory variants in Andersen et al. (Andersen M C, Engström P G, Lithwick S, Arenillas D, Eriksson P, Lenhard B, Wasserman W W, Odeberg J. In silico detection of sequence variations modifying transcriptional regulation. PLoS Comput Biol. 2008 January; 4(1):e5, incorporated herein by reference).

Variants falling near exon-intron boundaries can then be evaluated in step (318) for their impact on splicing, for example, using the maximum entropy method of maxENTscan. Maximum entropy scores can be calculated for the wild-type and mutant sequence independently, and can be compared to predict the variant's impact on splicing in step (328). Changes from a positive wild-type score to a negative mutant score can suggest a splice site disruption. Variants falling within exons are also analyzed in steps (312) and (322) for their impact on exonic splicing enhancers (ESE) and/or exonic splicing silencers (ESS). The number of ESE and ESS sequences created or destroyed based on the hexanucleotides reported as potential exonic splicing regulatory elements (e.g. as shown by Stadler M B, Shomron N, Yeo G W, Schneider A, Xiao X, Burge C B. Inference of splicing regulatory activities by sequence neighborhood analysis. PLoS Genet. 2006 Nov. 24; 2(11):e191, incorporated herein by reference) has been shown to be the most informative for identification of splice-affecting variants by Woolfe et al. (Woolfe A, Mullikin J C, Elnitski L. Genomic features defining exonic variants that modulate splicing. Genome Biol. 2010; 11(2):R20, incorporated herein by reference).

Variants falling within 3'UTRs can be analyzed in steps (314) and (324) for their impact on microRNA binding in two different manners. First, 3'UTRs can be associated with pre-computed microRNA binding sites using the targetScan algorithm and database. Variant 3'UTR sequences can be rescanned by targetScan in order to determine if microRNA binding sites are lost due to the impact of the variation. Second, the binding strength of the microRNA with its wild-type and variant binding site can be calculated by the RNAcofold algorithm to return a ΔΔG score for the change in microRNA binding strength induced by introduction of the variant.

While interpretation of frame shift and nonsense mutations is fairly straightforward, the functional impact of nonsynonymous changes and in-frame indels or multinucleotide substitutions is highly variable. Currently, annotation pipeline (202) can be configured to use the PolyPhen-2 algorithm, which performs favorably in comparison to other available algorithms, for prioritization of nonsynonymous single nucleotide substitutions in steps (316) and (326). PolyPhen-2 utilizes a combination of sequence-based and structural predictors to predict the probability that an amino acid substitution is damaging, and classifies variants as benign, possibly damaging, or probably damaging. These outputs can be reported by annotation pipeline (202) along with the probability score of the variant being deleterious.

A major drawback to predictors such as PolyPhen-2 is the inability to address more complex amino acid substitutions. To address this issue, annotation pipeline (202) can also be configured to report the Log R.E-value score of variants in step (326), which is the log ratio of the E-value of the HMMER match of PFAM protein motifs between the variant and wild-type amino acid sequences. This score has been shown to be capable of accurately identifying known deleterious mutations. More importantly, this score measures the fit of a full protein sequence to a PFAM motif, therefore multinucleotide substitutions are capable of being scored by this approach. As phased genomes gain in prevalence, phased nonsynonymous variants can be analyzed for their combined impact on protein function.

Annotation pipeline (202) output can feed directly into statistical and bioinformatic strategies for variant analysis. Annotation and prioritization of variants prior to statistical analysis can be performed and can be crucial to the success of sequence based disease association studies. Annotation and prioritization is also directly applicable to the identification of causal variants in post-GWAS/linkage sequencing studies, forward genetic screens, carrier testing, or even the identification of causal variants in clinical sequencing applications such as unknown disease diagnosis and cancer driver identification.

FIG. 4 shows four major classes of variant annotations that can be generated and used by annotation engine (202), including:

(1) residence within known or inferred genomic elements (including exons, promoters, protein domains transcription factor binding sites, conserved elements, miRNA binding sites, splice sites, splicing enhancers, splicing silencers, common SNPs, UTR regulator motifs, post translational modification sites, and common elements);

(2) prediction of the functional impact of a variant on a genomic element (including conservation level, impact on protein function, changes in transcription factor binding strength, microRNA binding, coding impact, nonsynonymous impact prediction, protein domain impact prediction, motif based impact scores, nucleotide conservation, target scan, splicing changes including splicing efficiency, binding energy, and codon abundance);

(3) annotation of molecular and biological processes which link variants across genes and/or genomic elements with one another (including phase information, molecular function, biological processes, protein-protein interactions, co-expression, and genomic context; and (4) prior knowledge (i.e., annotation of known clinical characteristics of the gene or variant (including pharmacogenetic variants, phenotype associations, GWAS associations, biological processes, molecular function, drug metabolism GWAS catalog, allele frequency, eQTL databases, and text mining).

This multi-tiered approach to variant annotation (FIG. 4) enables analysis strategies that are inaccessible to individual laboratories and provides a more powerful framework for phenotype association and other sequence based investigational strategies as compared to the prevailing paradigm in the following ways:

(1) regulatory variants, which have been largely ignored in genome sequencing studies, are made accessible to high-throughput analysis;

(2) for candidate gene or region resequencing studies as well as clinical applications of sequencing for diagnosis, annotation and functional prediction of genetic variants can facilitate prioritization of variants that are more likely to be the causal variants;

(3) similarly, in forward genetic screens, annotation and prioritization can be used to rapidly identify causal lesions reducing animal costs and time to identification by reducing the number of required crosses; and (4) in whole genome sequence based association studies; at the single variant level, variants can be prioritized for likelihood of functional impact, alleviating the statistically intractable problem of testing millions of variants for disease association; at the gene level, appropriate collapsed variant sets can be produced so as to reduce noise from noncausal variants and improve the power to detect causative sets of variants; and at the systems level, variants can be assembled into biologically cohesive sets, increasing the power to detect genes that individually contribute little to the heritable component of disease.

Annotation execution in pipeline (202) proceeds in highly parallel fashion and includes classes of variant annotations that are entirely independent of one another, serially dependent annotations whose execution are dependent upon the completion and status of prior annotations, and synthetic annotations that generate new information through the combination of multiple annotation outputs. A description of the annotation processes used in pipeline (202) in terms of classes of information is presented first, followed by a description of the computational processes producing those results.

Annotation Classes

Physical and Gene-Relative Mapping and Characteristics

The physical mapping information provides the most basic level of information regarding the location of the variant and its relationship with basic elements. The chromosome, physical start position, physical end position, variant type (e.g. snp, insertion, deletion, substitution structural variants, copy number variants, etc.) and reference and alternate alleles are supplied by one of a few standard file formats, including VCF (variant call format) (see: www.1000genomes.org), Complete Genomics native file format, or basic tab delimited BED-like file format. Additionally, haplotype information, used to track whether variants occur in cis or trans relative to one another, can be provided and that information will be conserved. In certain embodiments, system 100 can take into account multiple variants on the same haplotype.

The above location information is utilized to execute a basic mapping step which determines what the nearest gene/transcripts are, what type of gene (coding vs. non-coding) is nearby, the location of the variant relative to the gene (exonic, intronic, upstream, downstream) and the distance from the gene-body. Determinations are based upon physical distances within the genome. Either known or predicted genes can be utilized for this step, in one specific implementation the UCSC Known Genes database is used, which is a compilation of information from RefSeq, GenBank, Consensus CDS project, UniProt, and other sources of evidence for genes and whether they are coding vs. non-coding genes. Custom conversion scripts included in pipeline (202) can transform the various variant data files into a common input format.

Non-limiting examples of alternative reference genomes include a version of the human genome or different species. Non-limiting examples of alternative gene databases include ENSEMBL and predicted genes such as, Genscan for mapping. Alternate variant input formats for input include copy number variation, structural variation, and upstream integration of variant calling from sequence data or alignment files. Non-limiting examples of other gene-types or more fine-grain determination of gene-types include, microRNA, snoRNA, piwiRNA, pseudogenes, physical mapping to chromosome bands, STS markers, distance to recombination hotspots, other physical landmarks in the genome, mapping to predicted exons or predicted open reading frames and ancestral nucleotide status such as Neanderthals, Chimp, etc.

Coding Gene Impact, Inferred and Predicted

If a variant is mapped to an exon of a protein coding gene, its impact upon the coding sequence is inferred based upon the standard rules of the genetic code, and prediction of impact is performed based upon a series of functional impact prediction algorithms. First, the position of the variant within the protein sequence and the distance of the variant relative to the N-terminal and C-terminal ends of the protein are determined and used in determining the impact of truncating variants. Next, the basic coding impact, e.g. synonymous, nonsynonymous, frameshift, etc. is determined as well as the original and variant amino acids based on the standard genetic code. Then, dependent upon the status of the previous annotations a series of functional impact predictions are performed. For nonsynonymous variants, the predicted impact of the amino acid substitution on protein function is determined based upon the SIFT, Polyphen-2, and Condel algorithms. For coding variants, including in-frame insertions and deletions, a Log Ratio E-value score of variants, which is the log ratio of the E-value of the HMMER match of PFAM protein motifs between the variant and original amino acid sequences. This score has been shown to be capable of accurately identifying known deleterious mutations. One example of a suggested threshold is scores with a Log R.E-value greater than 0.7 for predicted damaging variants. More importantly, this score measures the fit of a full protein sequence to a PFAM motif, therefore multinucleotide substitutions or separate substitutions on the same haplotype are capable of being scored by this approach. As phased genomes gain in prevalence, phased nonsynonymous variants can be analyzed for their combined impact on protein function.

For truncating variants (nonsense and frameshift) the percentage of the conserved upstream and downstream coding sequence removed by the truncation (conserved elements), taking into account alternate start sites, is determined and utilized to predict whether the truncation is damaging or not. The threshold for prediction of a damaging truncation removal of >4% of the conserved portion of the protein, a threshold with the greatest accuracy as defined empirically.

Also contemplated is the generation or destruction of post-translational modification sites; inclusion of additional predictive algorithms, such as SNPs3 and MutationTaster; and the basic physiochemical properties of changed amino acids, such as hydrophobicity, polarity, or side-chain volume.

Splicing Impact, Inferred and Predicted

Variants falling near exon-intron boundaries are evaluated for their impact on splicing in a couple of ways. One method is a simple determination of whether or not the variant impacts the invariant splice donor and acceptor sequences—returning an annotation that a splice donor or acceptor is damaged. A second method is a prediction of the impact of variants nearby a gene splice junctions based on the maximum entropy method of maxENTscan. Maximum entropy scores are calculated for the original and variant sequence independently, and considered for their impact on splicing. Changes from a positive original score to a negative variant score suggest a splice site disruption. Variants falling within exons are also analyzed for their impact on exonic splicing enhancers and/or silencers (ESE/ESS). The number of ESE and ESS sequences created or destroyed is based on the hexanucleotides reported as potential exonic splicing regulatory elements and shown to be the most informative for identification of splice-affecting variants.

Also contemplated is splice site generation, noncanonical splice sites, intronic splicing enhancers/silencers, splicing cofactor binding sites. Non-limiting alternative splicing prediction tools include, NNSplice and ESE-Finder.

Regional Information

Regional information refers to sequence-based, cross-species inferred and structural characteristics of the specific region of the genome containing the genetic variant. Two primary annotations are the repeat structure of the genomic region and its conservation across species. Segmental duplications, duplicated regions of the genome which increase the likelihood of mismapped reads and false variant calls, are annotated. Variants are also associated with conservation information in two ways. First, variants are associated with conserved elements from the phastCons conserved elements at various depths of conservation. These conserved elements represent potential functional elements preserved across species. Conservation is also assessed at the specific nucleotide positions impacted by the variant by the phyloP method.

Also included is mapability, recombination rate, other conservation levels, simple repeats, mobile elements, complex repeats, such as satellite sequences, nuclear mitochondrial sequence, horizontally transferred sequence from viruses and other organisms.

Population-Based Information

Population-based information refers to known rates and identifiers in populations already sequenced or genotyped. These variants are generally associated with dbSNP identifiers, however the system 100 platform also dynamically tracks and updates the allele frequency of variants processed through the system and derived from reference panels. System 100 reports the population allele frequencies for HapMap populations as well as allele frequencies in available reference populations including the 1,000 genomes project, publically available genomes provided by Complete Genomics, and Wellderly samples.

Also included are positive/negative/purifying selection rates.

Regulatory Variants

All variants, regardless of their genomic position, are associated with predicted transcription factor binding sites (TFBS) and scored for their potential impact on transcription factor binding. Predicted TFBS are pre-computed by utilizing the human transcription factors listed in the JASPAR and TRANSFAC transcription-factor binding profile to scan the human genome using the MOODS algorithm. The probability that a site corresponds to a TFBS is calculated by MOODS based on the background distribution of nucleotides in the human genome.

TFBS are called at a relaxed threshold within (p-value<1·10$^{-6}$) in conserved, hypersensitive, or promoter regions, and at a more stringent threshold (p-value<1·10$^{-8}$) for other locations in order to capture sites that are more likely to correspond to true functional TFBS. Conserved and hypersensitive sites correspond to the phastCons conserved elements, Encode DNASE hypersensitive sites annotated in UCSC genome browser, while promoters corresponds to 2 kb upstream of known gene transcription start sites, promoter regions annotated by TRANSPro, and transcription start sites identified by SwitchGear Genomics ENCODE tracks.

The potential impact of variants on TFBS are scored by calculating the difference between the variant and original sequence scores using a position weighted matrix method and shown to identify regulatory variants. A suggested threshold for damaged TFBS is either deleted TFBS or those with a delta score of less than −7.0. Variants known to influence expression levels, as determined by eQTL analyses are also annotated from the NCBI GTEx database.

Variants falling within 3'Untranslated Regions (3'UTRs) are analyzed for their impact on microRNA binding in two different ways. First, 3'UTRs are associated with pre-computed microRNA binding sites using the TargetScan algorithm and database. Variant 3'UTR sequences are rescanned by TargetScan in order to determine if microRNA binding sites are lost due to the impact of the variation. Directly impacted microRNA binding sites are listed as well, and the binding strength of the microRNA with its original and variant binding site is calculated by the RNAcofold algorithm to return a ΔΔG score for the change in microRNA binding strength induced by introduction of the variant. For microRNA transcripts (rather than their binding sites) bearing variants, a change in folding and binding energy, based on annealing with the consensus binding site, is also calculated by the RNAcofold algorithm. Moreover, a list of predicted lost and gained targets due to the new microRNA sequence is determined using the TargetScan algorithm to scan the novel microRNA sequence against known transcript 3'UTRs.

Also included is the location of enhancers, silencers, DNAse hypersensitivity sites, known TFBS based upon experimental data, long distance genome interaction sites, chromatin modification sites, ENCODE data, mRNA based predictions based on change in untranslated region motifs, change in RNA folding, translation efficiency due to synonymous mutations, or alternatively spliced exons are also included.

Clinical Annotation

Clinical annotations include both return of information contained within clinical variant databases as well as predicted clinical influences based upon the synthesis of gene-phenotype relationships and gene-variant impact predictions. On a variant by variant basis, System 100 determines whether the specific reported variant is contained with the Human Gene Mutation Database (HGMD), PharmGKB, GET-Evidence, and the COSMIC Database. HGMD cross-reference returns the disease associated with the genetic variant, PharmGKB cross-reference returns the PharmGKB entry name and the drug whose metabolism is perturbed by the variant, GET-Evidence cross-reference returns the inheritance, penetrance, severity, and treatability of the variant and disease if it is known, and COSMIC Database cross reference returns the number of cancer samples in the COSMIC database bearing that specific variant.

If the nearest gene, rather than the specific variant, is a gene known to be clinically relevant, it's association with disease as annotated by either OMIM, HGMD, or the NCBI Genetic Association Database is returned. Finally, if the variant falls nearest to a gene associated with cancer, that information is returned via cross-reference to the COSMIC database, Memorial Sloan Kettering Cancer Center, Atlas Oncology (http://atlasgeneticsoncology.org), the Sanger Cancer Gene Census, or network residence nearby known cancer genes. Drugs known to target the gene are also returned from DrugBank.

Finally, two different modified American College of Medical Genetics (ACMG) scores are returned, one based upon variants, or variants in genes known to be causally associated with a phenotype (Clinical) and a second score which includes genes known to carry genetic variants that are statistically associated risk factors for the development of a disease (Research). The ACMG scoring guidelines with categories 1-6 are modified to include a 2* and 4* category to provide more granularity to variant stratification. However, variants of category 1-2* are of most clinical relevance and category 6 contains more common risk factors for disease. ACMG category 1 variants are rare (<1% allele frequency) variants with good evidence for their association with disease. ACMG category 2 includes more common variants (1-5% allele frequency) associated with disease as well as novel variants in known disease genes predicted to impact gene function by either removing a splice site donor or acceptor, producing an amino acid substitution predicted to functionally impact the protein, or truncating the protein in a damaging manner. Category 2* includes truncating variants not predicted to damage protein function. Variants less confidently predicted to be associated with disease, either through neutral coding changes or impact upon regulatory function are placed in categories 3, 4, and 4* with predicted neutral variants and known phenotype associated variants assigned to categories 5 and 6 respectively.

Also included is the use of mouse knockout phenotypes, model organism phenotypes, and predicted phenotypes.

Gene Networks, Pathways, Biological Process and Molecular Functions

This category of annotation includes information that can link genes and variants to one another based upon biological, molecular, and/or functional relationships. These relationships are useful for pathway or process based collapsed association methods or inferring the phenotypic influence of particular variants. In our specific implementation Reactome pathways and gene ontology biological processes of the nearest gene are utilized to provide biological relationships. Disease Ontology annotations are utilized to provide phenotypic relationships. Protein domain information and molecular functions (as annotated by Gene Ontology) utilized by the nearest gene are used to provide molecular and functional relationships.

Also included is the use of tissue expression levels, tissue specific expression status, other pathway and network resources, and co-expression networks.

It is one drawback to currently available annotation systems that they are limited in the annotations they compute, retrieve, and provide for a given variant. Different annotation information is stored in a variety of different databases, often maintained by particular institutions with specific interests. The system 100 aims to consolidate a wider range of annotation information than has generally been provided. Accordingly, in some implementations, each variant processed by the system is annotated with at least 50 predefined annotation categories, each of which may be one particular category of information within one of the eight annotation classes described above. Generally, although not necessarily, out of these 50 annotation categories, at least 10 will involve accessing a different separately maintained database to search for annotation information. Although the databases are separately maintained, most of the institutions that maintain these databases allow them to be mirrored at system 100 for faster direct access. In some implementations, each variant processed by the system is annotated with at least 55, 60, 65, 70, or 75 different annotation categories. In some embodiments found to be especially suitable, over 80 annotation categories are provided. Including more annotations is surprisingly valuable because it is often not known what kind of information may be desirable in future data mining projects through a database of annotation data. It will also be appreciated that even though at least 50, at least 80, or more annotation categories are provided for each variant and may be stored and output by the system in an annotation file, some number of the category entries for a given variant will contain no information because the variant will not appear in all databases, will not necessarily be in an exon, etc.

Computational Process

The computational processes underlying the system 100 output do not necessarily follow the structure given above in the annotation classes. Rather, annotation execution proceeds in highly parallel fashion on a high-performance computational cluster and includes classes of variant annotations that are entirely independent of one another, serially dependent annotations whose execution are dependent upon the completion and status of prior annotations, and synthetic annotations that generate new information through the combination of multiple annotation outputs.

Data Input

The input requirements are a list of variants including the chromosome, start position, end position, and reference and variant alleles—transferred via a network connection for automated processing or provided via a local file.

One of a few standard file formats, including VCF (variant call format), Complete Genomics native file format, or basic tab delimited BED-like file format are accepted, but then converted to the following tab-delimited structure: (1) Haplotype number (can be a placeholder); (2) Chromosome (with syntax: "chr1", "chr22", "chrX", etc.); (3) Start position (0-based coordinates); (4) End position (0-based coordinates); (5) Variant type ("snp", "ins", "del", "delins"); (6) Reference allele(s); (7) Observed allele(s); and 8.) Notes.

Pre-Annotated Database

A pre-annotated database (FIG. 5) stores annotations for observed variants, including variants reported in dbSNP, or other databases mentioned above, as well as any annotations completed by system 100 on novel variants. Annotations are stored in a scalable database capable of quick queries based upon physical location alone. In one specific embodiment, they are stored in a non-relational database such as MongoDB.

Previously annotated variants are extracted from this database, and novel variant annotations are stored within the database upon completion in order to speed up the annotation of subsequent genomes. Annotations for variants not found in the database are computed de novo in an automated parallel computing environment as described below. Subsequent retrieval of pre-annotated variants contained within variant files submitted for annotation is based purely upon physical coordinate based queries against the pre-annotation database.

Transcript-Based Annotations

Transcript-based annotations (FIG. 5) rely upon the mapping of variants relative to known gene transcripts. This includes, for example, the nearest gene or transcript, the position of a variant in the genome relative to a transcript, the position of the variant within the transcript (e.g. exonic, intronic, upstream, etc.) and the position of the variant relative to functional elements or "gene components" of the transcript (e.g. untranslated regions, splice junctions, distance from coding start and stop sites etc.).

Annotation depends upon a database of the physical location of genes and gene components and a measurement of the physical distance or occupancy of a variant relative to these gene components. In more complex instances, a reference genome sequence is utilized to extract the genomic sequence relevant to the annotation in question; the sequence is processed based upon the reported coding frame and then trimmed based upon proximity to gene components or converted to other biological sequences by utilizing the standard genetic code to produce input formats compatible with downstream tools. Based upon this information a series of transcript based annotations are produced.

The simplest case is annotations dependent upon the identity of the nearest gene. Prior knowledge regarding the nearest gene/transcript is produced from knowledge bases, including the type of gene, the relationship of the gene to phenotypes and biological processes as determined by clinical phenotype database (OMIM, HGMD, COSMIC, Disease Ontology, or other cancer gene databases), relationship of the gene to other compounds (e.g. DrugBank), and relationship of the nearest gene to biological pathways, networks, or molecular function (e.g. Gene Ontology, Reactome Pathways, etc.). These cross-references are based upon gene synonym tables, for example those provided by the UCSC Genome Browser.

More complex cases require utilization of the position of the variant relative to the transcript body as well as the sequence of the surrounding nucleotide context. In these cases, given the position of the variant within the transcript body, a series of annotations and predictions that are dependent upon the location of a variant relative to functional transcript elements and calculation of results based upon the specific surrounding nucleotide sequence are produced—these include inferred and predicted influences upon splicing, and splicing machinery, as well as inferred and predicted influences upon microRNA binding sites within the untranslated regions.

Finally, given the gene type and position within the transcript, a series of annotations are produced that depend upon defining the protein produced by the gene and the changes to the amino acid sequence based upon the standard genetic code. These annotations include the position of the variant within the protein sequence and the distance of the variant from the coding start and stop sites, the affected amino acids, and predictions which utilize the protein sequence and perturbed amino acids including functional predictions (SIFT, Polyphen-2, Condel), and protein domain matching and scoring (e.g. HMMER scanning of the protein sequence against protein family models).

Functional Element-Based Annotations

The functional element-based annotation class (FIG. 5) does not depend upon the identity of the nearest gene, but rather the characteristics of the genomic position itself. The reference components of these annotations can sometimes be considered synthetic annotations on their own; however the considered synthetic elements are based upon synthesis of data prior to any variant annotation in order to identify functional elements of interest in the genome. For example, transcription factor binding site motifs are scanned against the genome, their scores and positions relative to known genomic elements are determined, and specific transcription factor binding sites are called based upon the synthesis of this information. In the annotation process these elements are predefined and variants are mapped directly to these elements and their functional impact, if any, are predicted based upon the sequence context. A basic functional element-based annotation is based purely upon the residence of a variant within a genomic region with a particular characteristic—for example regions denoted as Segmental Duplication. Databases of genomic regions, such as Segmental Duplications, are maintained and variants are mapped against these bins to determine whether they land within the span of the element. Other examples including conserved elements or base-specific conservation levels.

More complex annotations rely upon the residence of a variant within a functional bin along with calculations that depend upon the identity of the original and variant sequence. These annotations including impact scoring for variants within transcription factor binding sites, or determination of the influence of variants upon microRNA genes. Thus, for functional element-based annotations, the locations of functional elements in the genome are either defined a priori in knowledge bases and mapped to the reference genome based upon physical location, or defined by searching for patterns within the reference genome that define functional elements. The bins defined by physical location coordinates are utilized to determine the residence of genetic variants within a functional element and the sequence of those bins is extracted from the reference genome, modified with the variant information, and scored using the various predictive algorithms described above.

Variant-Based Annotations

A variant-based annotation (FIG. 5) class depends upon prior or generated knowledge about the variant itself. For example, numerous sequencing and genotyping projects have catalogued the type and frequency of particular variants in different reference populations. These population based annotations are either generated from reference data or drawn from knowledge bases and reported—for example as known identifiers (dbSNP ID's), frequency in different reference populations, or frequency in different samples of known disease-status (e.g. tumor genomes).

Most clinical annotations, and other prior knowledge derived from variant-centric databases (such as the reported associations of variants with particular molecular or physiological phenotypes in HGMD, GET-Evidence, or eQTL databases) are variant-based. Cross-referencing is done based upon conversion to data within external knowledge bases to physical coordinates in the genome (as defined in Data Inputs), execution of the system 100 annotation pipeline (202), and deposition of the resulting annotations in the pre-annotated database.

Synthetic Annotations

Figure 5:
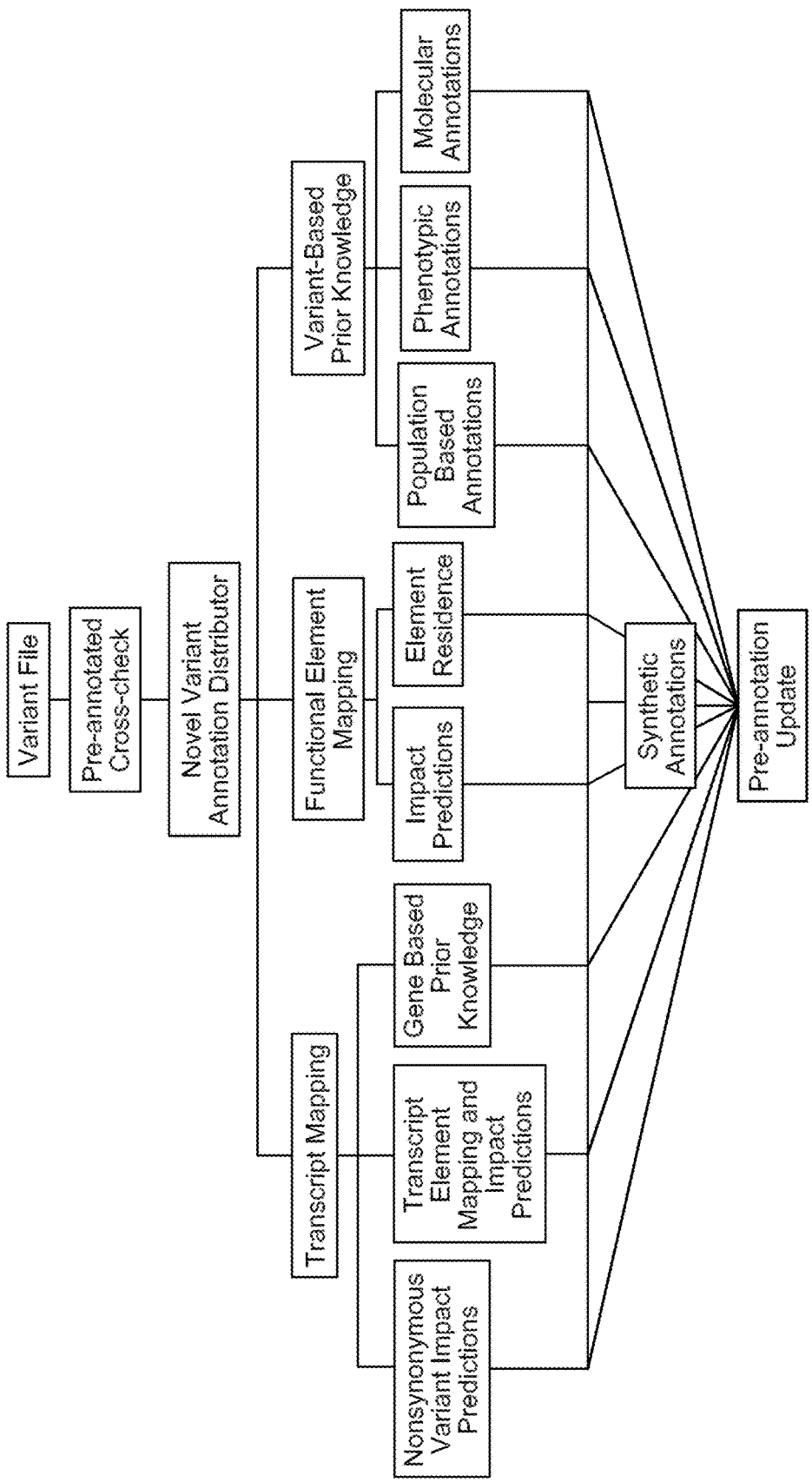
FIG. 5 is a diagram illustrating an example of the process flow of an annotation pipeline that can be included in the system of FIG. 1 in accordance with one embodiment.

Certain annotations depend upon the synthesis of multiple annotations, termed synthetic annotations (FIG. 5). These annotations are split into two types, synthetic annotations generated prior to use in the system 100 annotation pipeline (202) and utilized as knowledge bases for other annotations, or synthetic annotations that depend upon the output of active variant annotation. Pure synthesis of prior data to define functional elements is exemplified by the definition of transcription factor binding sites to be used to produce, for example, functional element based annotations as described above.

Hybrid-synthetic annotations involve the combination and merging of any subset of the previously described annotations in order to produce a novel layer of annotation. One non-limiting example is the prediction of impact of truncating variants that rely upon the definition of a truncating variant, its position within the coding sequence, and the amount of flanking conserved sequence removed by the variant. In that example, production of a synthetic annotation requires information from the annotation process as well as reference to the various knowledge bases maintained by system 100.

There also exist annotations that are pure synthesis of variant based annotations completed in prior steps. One non-limiting example of this sort of annotation is ACMG scoring, which relies upon the identity of the nearest gene, the association of the nearest gene with disease phenotypes, and the predicted impact of the variant upon the gene based upon the above described coding, splicing, and regulatory prediction tools. These annotations rely upon the combination of previous annotation outputs through logical operators and rules to define a novel annotation result.

In summary, after a population based sequencing study is carried out and variants are identified, the variants can be passed through annotation pipeline (202), predicted functional variants filtered based on the prediction algorithms implemented in the pipeline, prioritized variant sets generated based on the linking elements generated by the pipeline, and finally statistical tests can be performed on these variant sets in order to identify variant sets associated with disease (226).

These results can then be used by the various modules illustrated in FIG. 2, and as describe below.

Population Sequencing Module (224)

Large population based sequencing studies are underway in order to identify mutations that underlie disease predisposition. If one accepts the rare variant hypothesis of disease predisposition, one would expect rare variants predisposing to disease will be associated with high relative risk, but because of their low frequency, simple univariate analyses where each variant is tested for association with disease will require extremely large sample sizes to achieve sufficient power. This problem is compounded tremendously if disease predisposition results from the interaction and combination of extremely rare variants segregating and encountering one another throughout the population. Variant collapsing strategies have been shown to be a powerful approach to rare variant analysis; however, collapsing methods are extremely sensitive to the inclusion of noncausal variants within collapsed sets. The key to unlocking the power of variant collapsing methods, and facilitating sequence based disease association studies in reasonable study sizes and at reasonable cost, is a logical approach to forming collapsed sets. In fact, regardless of the allelic frequency and penetrance landscape underlying common disease predisposing variants, set based analyses can expose what simple linkage or association studies have failed to reveal.

Another application of the Population Sequencing Module 24 is in the field of pharmacogenomics. It is known that the safety and efficacy of drug related therapies can be associated with the genetic makeup of the individual patients. This fact can be especially significant in clinical trials of new drugs and other therapies, but correlating variants in clinical trial subjects with safety and efficacy data gathered for the drug or therapy during the clinical trials has proven difficult. Variant collapsing methods are important tools for discovering relevant associations in this context, and these variant collapsing methods are depend critically on functional annotations to provide a logical approach to selecting the variants for collapsed sets. The annotations and algorithms described herein are especially valuable in this application.

Family Sequencing Module (204)

The family sequencing module (204) can work in a manner similar to the population sequencing module (224), however in this case the diseases to be considered will generally be more severe, and the filtering of variants will follow a genetic model. For example, a family of four with unaffected parents, one affected child and one unaffected child, but having various different family structures can be accommodated by the analysis strategy implemented in certain embodiments of module (204).

Again, the process begins with a long list of variants (302) identified in the mother, father, and children. Variants are annotated through pipeline (202) as illustrated in FIG. 3. It can be expected that the causative gene will carry at least two predicted functional variants, one inherited from the mother and the other inherited from the father. The causative gene should not carry multiple functional variants in either parent or the unaffected child, unless the multiple functional variants impact only one copy of the gene in each parent. Essentially, the functional predictions generated by annotation pipeline (202) can be used to generate a list of candidate genes where the affected child carries predicted functional variants in both copies of the gene, each parent carries functional variants in only one copy of the gene, and the unaffected child carries only one or zero predicted functional variants in the gene.

Other filtration schemes can be generated for different genetic models. For example, in a sex-specific inheritance model module, family sequencing (204) can be configured to look for genes on the X-chromosome where only one copy of the gene carries functional variants in the unaffected mother, no functional variants are carried by the unaffected father, and the functional variant from the mother is inherited by the affected son.

If multiple candidate genes are identified by the variant filtering schemes implemented in family sequencing module (204), then phenotypic information can be used to filter the variant list. This analysis can use the linking elements generated by annotation pipeline (202), or potentially the network based prediction of disease genes to be described below. For example, if the disease in question is an autoimmune disease, the candidate genes can be ranked based upon the annotation of immune related functions generated by the linking elements.

Tumor-Normal Sequencing Module (208)

The purpose of the tumor-normal sequencing module (208) is to identify somatic mutations in the tumor and identify causative somatic mutations that may inform treatment strategies (210). First, the list of variants identified in the tumor and normal genomes can be used to isolate genetic variants observed only in the tumor genome. These tumor specific somatic variants can be passed through annotation pipeline (202) and filtered for functional variants or variants in genes known to be involved in tumorigenic processes. This list of variants can then be cross-referenced with a database of known gene-mutation-drug interactions (to be constructed) and passed through a decision tree to identify promising therapeutic interventions (210).

A sample decision tree would flow as follows: If EGFR is amplified→and KRAS is not mutated→recommend Cetuximab.

Drug Metabolism and Known Disease Genes (212)

In a single genome sequencing setting, some conclusions can be made directly from the mutations observed in single genes, e.g. the Myriad BRCA test or other genetic tests for known drug metabolism variants. Annotation pipeline (202) can be configured to take these tests one step further by including predictions based on variants in genes known to be associated with specific diseases or drug metabolism phenotypes, but where the variant itself has not been specifically observed to impact disease or drug metabolism.

Disease Example:

Mutations in BRCA are known to predispose to breast cancer. A woman's genome is sequenced, variants are passed through the pipeline (202), and mutations that are predicted to impact BRCA are observed. These variants are flagged, for risk of breast cancer and information regarding the mutation and predictions are returned.

Drug Metabolism Example:

CYP2C9 is the principle metabolism enzyme for Warfarin. Loss of function alleles are known to cause poor warfarin metabolism and sensitivity. Variants in CYP2C9 would be run through the annotation pipeline (202). Any variants not known to impact warfarin metabolism, but predicted to be damaging to CYP2C9 would be returned as predictions of sensitivity to Warfarin.

Multi-Gene Output for Known Disease Genes (216)

Annotation pipeline (202) can easily recreate the reports generated by DTC genotyping companies such as 23andMe, Navigenics, etc. Variants from a genome are passed through annotation pipeline (202), and associated with known SNPs in dbSNP (the first step described in the annotation pipeline section). The dbSNP ID's are cross-referenced with the catalog of known disease associations and their odds ratios in the Genome Wide Association catalog. The cumulative impact of those variants across the whole genome, using the odds ratios of each variant, can then be combined to produce a disease risk.

Single Genome—Cumulative Disease Risk (220)

This can be an extension upon the 23andMe or Navigenics type predictions described above, using predictions for gene-disease association as well as predictions of variant impact on disease. Conventional genetic testing products focus on specific variants associated with disease or solely on genes known to be related to a disease and do not consider a whole genome perspective. The systems and methods described herein encompass analyses of specific variants and analyses of specific genes while producing more powerful risk predictions by including genes determined to be associated with disease by the network propagation strategy and interrogating possible forms of human genetic variation. In addition, most conventional approaches do not account for molecular networks and connections between genes attributable to their participation in common processes or biochemical pathways.

System 100 can be configured to process whole genome genetic variant data for an individual into disease risk quantification through computational analysis and network modeling. First, each variant can be processed through the annotation pipeline (202). After variants have been processed through this pipeline, the output is used to produce a weighted score for the combined impact of variants on each gene, which essentially represents an estimation of the percent functionality of each gene. These percent functionalities are used to produce a disease specific score as described below.

To identify genes that may be associated with specific diseases, first, a weighted genetic network is compiled through publicly available resources, where the connection between genes is weighted based upon the confidence that the connection truly exists. The importance of each gene within the network is calculated based upon the number of connections it makes to other genes, and the importance of the genes to which it is connected. For example, a pagerank algorithm, heat diffusion algorithm, or degree centrality calculation can be used to produce this global centrality score. Next, for each disease, a disease specific score is generated for each gene by assigning a high importance score to genes known to be associated with the particular disease and then the scores are propagated through the network to generate a disease specific centrality score. Again, these disease specific centrality scores can be generated by propagating information through a pagerank algorithm, heat diffusion algorithm, degree centrality calculation, or other network centrality measure. For each gene, the difference between its global centrality score and the disease specific centrality score represents its importance in mediating the disease in question.

A whole genome sum of products can then be generated to produce a final disease score for the individual. The product is the importance of the gene to the specific disease state in question multiplied by the percent dysfunction scored for that gene through the first phase of the algorithm. These products are summed up across genes to produce a final disease score for the individual. The relative disease score across individuals represents an approximate relative risk of disease.

Filtering Algorithms to Identify Disease-Associated Variants

The multi-tiered annotations provided by the annotation pipeline (202) can be leveraged to identify disease associated variants within (1) single cases of idiopathic disease, (2) small pedigrees including affected individuals, and (3) larger groups of unrelated individuals with and without disease. The manner in which the disease-associated variant is identified relies on the creation of appropriate filters and/or statistical techniques as described below.

Individual Genomes

Given the high number of novel or very rare mutations that are present in any one genome, it is necessary to derive an appropriate filtering algorithm in order to determine the likely disease-causing variant from this set. The filter can be based on the relative "scores" attributed to the degree of damage introduced in a genomic element by a given mutation. The algorithm can use single scores or a weighted combination or scores to rank the most likely disease variants.

Small Number of Related Individuals

The filtering algorithm described above can be augmented with pedigree information in the case that related individuals are available for genome sequencing. Mendel's laws of inheritance can be overlaid on the basic filter to identify only those variants that track with the disease model (e.g., homozygous recessive, compound heterozygous, autosomal dominant).

Group of Unrelated Individuals

When sufficient numbers of unrelated individuals with and without disease are sequenced, it is possible to perform statistical tests to identify disease-associated variants based on the frequency of variants in cases versus controls (or population A versus population B). Within this extension, annotations produced by system 100 can provide the basis for collapsing sets of variant types (e.g., non-synonymous coding SNPs with an exon/gene/set of genes/pathway) into frequencies for use in downstream statistical tests.

Inclusion of Higher-Order Annotations

As genomic knowledge increases within system 100 and without, higher-order annotations such as (1) tissue-specific and transcript-specific expression; (2) methylation status; and (3) other epigenomic features, can be incorporated into both the basic annotation pipeline (202) as well as filtering algorithms as appropriate.

Empirically-Derived Variant Classifiers

It should also be noted that the existing annotation and filtering pipelines can be leveraged to build empirically-derived variant classifiers to identify likely disease-associated variants based on features shared with known disease-causing mutations.

Thus, variant file (302) data can be stored in, e.g., database (108) as can the annotated and filtered data produced by annotation pipeline (202) and the various modules (204-226). This data can then be used to refine the annotation and filtering algorithms. For example, as the amount of data in database (108) increases and new links and patterns in the data can be identified that can further inform the annotation and filtering being performed by system 100. Accordingly, algorithms (104) can comprise analytics that are configured to identify and refine linking information and patterns in the annotated and filtered data stored in database (108).

Thus, the invention provides, among other things, a genomic annotation system and a computer-based method for predicting a risk of an individual developing a disease.

Having now generally described the invention, the same will be more readily understood through reference to the following examples which are provided by way of illustration, and are not intended to be limiting of the present invention, unless specified.

EXAMPLES

Example 1: Whole Genome Sequence Data from the Complete Genomics, Inc. Public Domain Repository Publicly available complete genome sequence data was obtained on 69 individuals of high quality (~60× coverage, ~97% bases called) produced by Complete Genomics, Inc. (CGI) by downloading data from the company's website (http://www.completegenomics.com/sequence-data/download-data/). The assembly of the genomes as well as variant calling for them has been described in the literature. (Drmanac et al., 2010, Roach et al., 2010)

The genotypes from the available "MasterVar Beta" files provided by CGI were directly used. Additional filtering steps for the analysis of genotypes beyond those that went into the construction of the public domain files were not required.

The 69 individual genomes consisted of 22 individuals of Northern European ancestry (abbreviated as CE for the CEPH or CEU HapMap Population), 10 individuals of Yoruban ancestry (YR), 5 individuals each of Mexican (ME) and African ancestry living in Dallas (AS), 4 individuals each of Japanese (JP), Han Chinese (CH), Italian (TS), East Indian (GI), Maasai Kenyan (MK) and Luhya Kenyan (LW) ancestry, and 3 individuals of Puerto Rican ancestry (PU).

13 CE individuals who were the offspring of a couple of other CE individuals; one YR individual who was the offspring of a YR couple; and the 3 PU individuals who were a mother-father-offspring trio were excluded from the analysis. Therefore, 52 individuals from 10 different global populations were ultimately considered in the analysis. To show how some of the results apply to other data sources, sequence data available from the 1000 genomes project (www.1000genomes.org/) was also leveraged.

For one set of analyses, an ancestry assessment-verified was considered (see below) for female European individual's genome that was sequenced by CGI independently of the 69 genomes obtained from the public domain.

Example 2: Ancestry Assessment

The genetic background similarity of the 69 individual genomes downloaded from the CGI website was assessed, in addition to the single independently-sequenced European female's genome, by constructing identity-by-state (IBS) allele sharing similarity matrices using 16,411 markers which had also been genotyped on 4,123 individuals in various public domain databases for whom ancestry was known. IBS allele was also calculated sharing matrices based on 19,208,882 variants determined from the whole genome sequencing for the 52 individuals ultimately used on the analyses in addition to the parents in the Puerto Rican trio.

Figure 19:
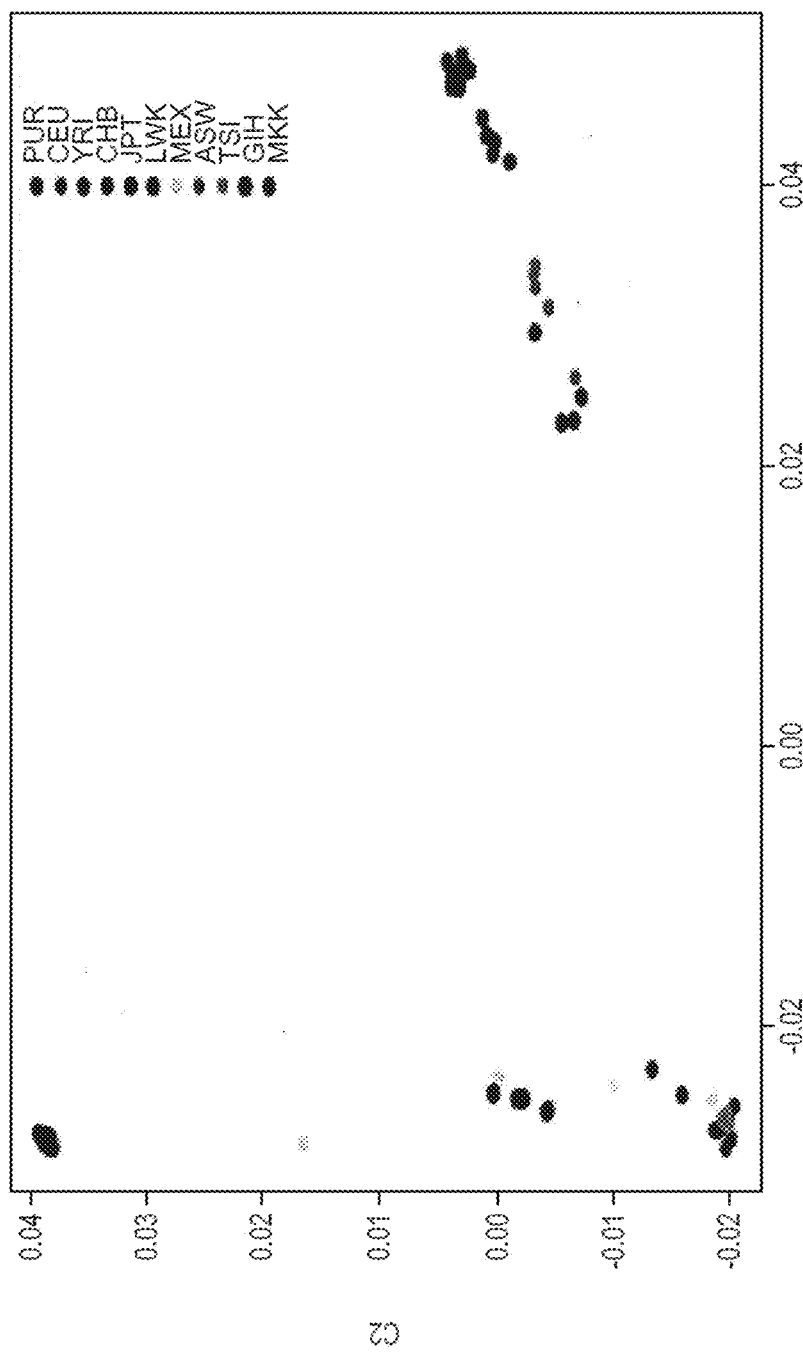
FIG. 19 depicts a PCA plot of the similarity of the 54 unrelated individuals with complete genome data based on 19,208,882 SNVs obtained from the complete sequencing data without regard to a reference panel of individuals with global ancestries (shading according to population is provide in the inset).

Multidimensional scaling (MDS) analysis was then applied to the sharing matrices to determine patterns in genetic background similarity of the individuals. FIG. 18A and FIG. 18B depict the first two PCs for the allele sharing determined through the use of the 16,411 markers genotyped on the 4,123 reference individuals as well. FIG. 19 depicts the first two PCs the allele sharing determined through the use of the 19,208,882 markers identified in the sequencing of the genomes of the 52+2 individuals. It is quite clear from these analyses and plots that the 52 individuals whose genomes we are studying have diverse ancestries that are consistent with the populations they are reported to represent. Additional analysis of the single European female's genome sequenced independently of the 52 genomes verified her European ancestry.

Example 3: Variant Allele Determination

To catalog the position-specific differences (i.e., variants) between the 52 genomes two different strategies were considered. First, each genome was compared to the human genome reference (version hg18). Second, the ancestral allele of each variant was then determined by comparing the genomes to the available chimp genome reference.

Human Reference Allele Determination

The sequence position of each variant site relative build hg18 of the human genome provided on the UCSC browser was determined. This was done for variant types that could be determined from the CGI variant files in the public domain, including SNVs, small insertion and deletion variants and multinucleotide variants (i.e., small stretches of sequence where the adjacent nucleotides present differ from the reference genome). Thus, the number and type of 'non-reference' variants possessed by each of the 52 individual genomes studied was determined. Large structural variation, large copy number variants (CNVs) and other large repetitive element-based variants were not considered.

The use of the human genome reference for assessing inter-population differences in the frequency and rate of functional variant is problematic since the available UCSC Genome Browser human genome reference (hg18) is constructed from DNA of European individuals. Thus, the frequency or 'labeling' nucleotides as variants that are 'reference' or 'non-reference' in other populations would be dictated by what is present on the genomes of individuals of European ancestry, if the human genome reference (hg18) is used. This can easily lead to interpretive biases regarding the relationships between populations and genomic differences between those populations. In addition, functional element determination based on single individual genomes or genomes from individuals with a unique ancestry is problematic due to structural differences in genomes that may impact the very definition of a functional element. Thus, variants were characterized as 'non-reference' for the sake of consistency with the literature and to allow for the determination of a reasonable and accepted approximation of the functional impact of the variants observed in the 52 genomes.

Ancestral Allele Determination

The ancestral allele of each variant site was determined using the PanTro2 build of the chimpanzee genome. In essence, the allele at a variant site among the 52 genomes studied that was also present on the chimpanzee genome (i.e., the 'ancestral' allele) and which was not present on the chimpanzee genome (i.e., the 'derived' allele) was determined. Ancestral alleles were determined using alignment information between the PanTro2 build of the chimpanzee genome with the human genome (hg18) from the UCSC Genome Browser.

When ancestral alleles could not be determined, alignments between the RheMac2 build of the Macaque genome were switched with the human genome (hg18) and positions when both alignments failed to reveal ancestral information were ignored. Ultimately, non-reference variants (determined from the comparison to the human genome reference hg18 as described above) seen across individuals were pooled and it was determined whether these variants matched ancestral alleles. In such cases, these non-reference variants revealed that the deviation is actually in the human reference genome (hg18) and not the non-reference variant. Subsequently, individuals that harbored the non-reference variant no longer carried the variant while other individuals with the reference allele now contained a 'derived' or non-ancestral variant.

Given information about which variants were reference/non-reference and ultimately ancestral or derived, for each individual genome at each variant site the labels 'reference' or 'non-reference', 'ancestral' or 'derived' were assigned. Additional genotype labels to each genome as, e.g., 'homozygous derived,' 'heterozygous,' or 'homozygous ancestral', were then assigned for variant site positions for which we ancestral allele information has been determined.

With this information, derived variants (likely functional or not) that were only observed on a single genome (genome-specific or 'novel' variants), derived variants that were only seen among the genomes of individuals within a specific population ('population-specific' alleles or variants), as well as the overall and population-specific frequencies of the variants could be determined.

Example 4: Variant Functional Element Mapping

All variants were mapped to the UCSC Genome Browser human reference genome, version hg18. Subsequently, variant positions were taken and their proximity to known genes and functional genomic elements was determined using the available databases available from the UCSC Genome Browser. Transcripts of the nearest gene(s) were associated with a variant, and functional impact predictions were made independently for each transcript. If the variant fell within a known gene, its position within gene elements (e.g. exons, introns, untranslated regions, etc.) was recorded for functional impact predictions depending on the impacted gene element. Variants falling within an exon were analyzed for their impact on the amino acid sequence (e.g. synonymous, nonsynonymous, nonsense, frameshift, in-frame, intercodon etc.).

Example 5: Variant Functional Effect Predictions and Annotations

Once the genomic and functional element locations of each variant site were obtained, a suite of bioinformatics techniques and programs to 'score' the derived alleles (i.e., derived variant nucleotides) were leveraged for their likely functional effect on the genomic element they resided in. Derived variants were assessed for potential functional effects for the following categories: nonsense SNVs, frameshift structural variants, splicing change variants, probably damaging non-synonymous coding (nsc) SNVs, possibly damaging nscSNVs, protein motif damaging variants, transcription factor binding site (TFBS) disrupting variants, miRNA-BS disrupting variants, exonic splicing enhancer (ESE)-BS disrupting variants, and exonic splicing silencer (ESS)-BS disrupting variants.

As illustrated below, the functional prediction algorithms used exploit a wide variety of methodologies and resources to predict variant functional effects, including conservation of nucleotides, known biophysical properties of DNA sequence, DNA-sequence determined protein and molecular structure, and DNA sequence motif or context pattern matching.

Genomic Elements and Conservation

All variants were associated with conservation information in two ways. First, variants were associated with conserved elements from the phastCons conserved elements (28way, 44way, 28wayPlacental, 44wayPlacental, and 44wayPrimates). These conserved elements represent potential functional elements preserved across species. Conservation was also assessed at the specific nucleotide positions impacted by the variant using the phyloP method. The same conservation levels as phastCons were used in order to gain higher resolution into the potential functional importance of the specific nucleotide impacted by the variant.

Transcription Factor Binding Sites and Predictions

All variants, regardless of their genomic position, were associated with predicted transcription factor binding sites (TFBS) and scored for their potential impact on transcription factor binding. Predicted TFBS was pre-computed by utilizing the human transcription factors listed in the JASPAR and TRANSFAC transcription-factor binding profile to scan the human genome using the MOODS algorithm. The probability that a site corresponds to a TFBS was calculated by MOODS based on the background distribution of nucleotides in the human genome. TFBS at a relaxed threshold within (p-value<0.0002) was labeled in conserved, hypersensitive, or promoter regions, and at a more stringent threshold (p-value<0.00001) for other locations in order to capture sites that are more likely to correspond to true functional TFBS. Conserved sites correspond to the phastCons conserved elements, hypersensitive sites correspond to Encode DNASE hypersensitive sites annotated in UCSC genome browser, while promoters correspond to regions annotated by TRANSPro, and 2 kb upstream of known gene transcription start sites, identified by SwitchGear Genomics ENCODE tracks. The potential impact of variants on TFBS were scored by calculating the difference between the mutant and wild-type sequence scores using a position weighted matrix method and shown to identify regulatory variants in.

Splicing Predictions

Variants falling near exon-intron boundaries were evaluated for their impact on splicing by the maximum entropy method of maxENTscan. Maximum entropy scores were calculated for the wild-type and mutant sequence independently, and compared to predict the variants impact on splicing. Changes from a positive wild-type score to a negative mutant score suggested a splice site disruption. Variants falling within exons were also analyzed for their impact on exonic splicing enhancers and/or silencers (ESE/ESS). The numbers of ESE and ESS sequences created or destroyed were determined based on the hexanucleotides reported as potential exonic splicing regulatory elements and shown to be the most informative for identification of splice-affecting variants.

MicroRNA Binding Sites

Variants falling within 3'UTRs were analyzed for their impact on microRNA binding in two different manners. First, 3'UTRs were associated with pre-computed microRNA binding sites using the targetScan algorithm and database. Variant 3'UTR sequences were rescanned by targetScan in order to determine if microRNA binding sites were lost due to the impact of the variation. Second, the binding strength of the microRNA with its wild-type and variant binding site was calculated by the RNAcofold algorithm to return a $\Delta\Delta G$ score for the change in microRNA binding strength induced by introduction of the variant.

Protein Coding Variants

While interpretation of frameshift and nonsense mutations is fairly straightforward, the functional impact of nonsynonymous changes and in-frame indels or multinucleotide substitutions is highly variable. The PolyPhen-2 algorithm, which performs favorably in comparison to other available algorithms, was utilized for prioritization of nonsynonymous single nucleotide substitutions. A major drawback to predictors such as PolyPhen-2 is the inability to address more complex amino acid substitutions. To address this issue, the Log R.E-value score of variants, which is the log ratio of the E-value of the HMMER match of PFAM protein motifs between the variant and wild-type amino acid sequences, were also generated. This score has been shown to be capable of accurately identifying known deleterious mutations. More importantly, this score measures the fit of a full protein sequence to a PFAM motif, therefore multinucleotide substitutions are capable of being scored by this approach.

Example 6: Between and within Population Functional Variant Frequency and Rate Data Analyses The frequencies and rates of functional and non-functional derived variants among the genomes of individuals with different ancestries in a few different settings were compared. The methodologies associated with each of these settings are described briefly in isolation below.

General Population Comparisons

To compare frequencies and rates of different types of variants (reference or derived; predicted functional or predicted non-functional; coding, TFBS, etc.) across the 10 populations, graphical displays and linear regression techniques were used. For the regression analyses, simple dummy variables for each of the 10 ancestral populations were created (i.e., a value of 1.0 was assigned to an individual genome that belonged to a specific ancestral population and 0.0 otherwise) and were used as independent variables in a regression analysis with either the absolute number of variants of a specific type on a genome, or the rate of that variant type per of an individual's genomic variants, as a dependent variable. For these comparisons, the YR (Yoruban) population was taken as a reference, such that the estimated regression coefficients reflect deviations from the YR population. Tukey's 'Honestly Significantly Different (HSD)' method was used for evaluating pairwise differences between individual populations for the different variant types from an analysis-of-variance (ANOVA). The HSD method allowed the appropriate statistical inferences to be made given the number of pair-wise population comparisons made.

Homozygous Variant Comparisons

The frequency and rate of variants of the different types that were homozygous across the populations were compared using regression methods analogous to those described above. Graphical displays of the frequency and rate differences of homozygous variants across the populations were also considered.

Population-Specific Variant Comparisons

All of the variants that were only found on genomes of individuals with ancestries associated with three major continental populations were determined. First, the genomes from CE and TS subpopulations were combined to form a European (EUR; n=13) population, the JP and CH subpopulations were combined to form an Asian (ASN; n=8) population, and the YR, MK, and LW subpopulations were combined to form an African (AFR; n=17) population. The AS subpopulation was excluded from the formation of the African (AFR) population because that population represents African American individuals sampled from within the United States and therefore could reflect admixed individuals.

The number of variants that were observed only within each population for each variant category was determined, and both aggregated the total number and rate of such variants in each population as well as assessed the rate of such variants in each individual genome in each population. Z-tests assessing the equality of these frequencies were performed.

A regression analysis was also used to assess differences between the frequency and rates of African, European, and Asian population-specific variants. The African population was used as a reference and dummy variables for European and Asian ancestry were constructed. Pearson's correlation coefficients were calculated between rates of population specific functional variants relative to population specific variants and relative to variants.

Example 7: Simulation Studies Using Known Pathogenic Variants

The impact of using inappropriately ancestry-matched reference panels was assessed in efforts to identify patient-specific pathogenic variants responsible for an idiopathic condition via simulation studies. These simulation studies leveraged both the data and insights associated with the assessment of global functional variant diversity involving the 52 CGI genomes.

First, 506 known Charcot-Marie-Tooth (CMT) syndrome causing variants were taken from the OMIM database and their Polyphon2 and SIFT scores were computed (or rather, technically, 1.0-SIFT score, which we will refer to as the 'SIFT score') and their averages (average Polyphen2 score=0.825, average SIFT score=0.931, and average of the average value of the Polyphen2/SIFT scores=0.878) as well as 567 known Cystic Fibrosis (CF) causing variants (average Polyphen2 score=0.769, average SIFT score=0.891, and average Polyphen2/SIFT score=0.830) were obtained and variants reflecting these scores were 'implanted' in a European individual's whole genome sequence variant list.

Polyphen2 and SIFT are bioinformatics programs implementing procedures for determining the likely functional significance of non-synonymous coding SNVs and were including in the suite of programs used to characterize the likely functional effect of variants. This European individual was sequenced by Complete Genomics, Inc. in the same way as the 52 individuals taken from the CGI repository, but was not part of that panel of 52 individuals.

It was determined by placing the disease-causing coding variants among the other variants on this individual's genome, it was determined that the method could identify them as likely pathogenic and disease-causative among the other coding variants on that individual's genome.

This was pursued by comparing the coding variants on this individual's genome to reference panel genomes made up of individual genomes from among the 52 CGI genomes studied with the same and different ancestries. They comparison was performed using different bioinformatics functional prediction tools to assess their impact on pathogenic variant identification as well. CMT variants and CF variants were choses for exploration since CMT variants act in a dominant fashion and CF variants act in a recessive fashion. An individual not sequenced along with the 52 CGI public domain genomes was leveraged since the variants on this individual had not been deposited into dbSNP and other databases and thus many of them were not likely to have been studied by other groups.

CMT and CF variants were also implanted with the scores described above in the variant lists of a randomly chosen African (taken from the AS population, which could reflect African American ancestry), Mexican, East Indian, and Puerto Rican genome from the total of the 69 individuals for which WGS data was available from the CGI repository. The number of ns cSNVs (i.e., coding variants) that would be considered novel (i.e., patient-specific) were determined among these individuals' sets of variants with predicted functional scores from Polyphen2, SIFT, and the average Polyphen/SIFT score greater than those associated with the implanted, known disease-causing CMT and CF mutations when compared to different reference panel genomes sets These reference panel sets included the 1000 Genomes Project exome sequencing data (as of October 2011), both combined across populations considered in the Project and for each of the European, Asian, and African variant sets individually. Reference sets for variants from 52 individuals for which WGS data was available, as well as 8 randomly chosen Europeans, Asians, and Africans from these 52, were also created. Finally, a combined reference variant set that included the 1000 Genomes data and the WGS data for the 52 individuals was considered.

These analyses were pursued by assuming that the CMT mutation was dominant and the CF mutation was recessive (i.e., for the CF mutation only homozygous genotypes not observed in the reference panels were considered novel, whereas for the CMT mutation any genotype that was not observed in the reference panels, homozygous or heterozygous were considered novel).

Example 8: Results

Variant Identification

From the 52 individual genomes, 24,277,549 'non-reference' variants that deviated from build hg18 of the human reference genome represented in the UCSC browser were identified. This included 19374542 SNVs, 1941800 insertions, 2282925 deletions, and 678282 multinucleotide variants. A variant in one genome that was not present on the other 51 genomes was defined as 'novel'. A filter for novel variants using other publicly available databases was not performed since the DNA samples from the 52 individuals sequenced by CGI are available in the public domain and used often in polymorphism detection studies, such as the 1000 Genomes Project, and hence are likely to have genotype information for them in publicly accessible databases such as dbSNP.

In addition, it is known that different sequencing platforms vary in their ability to identify deviant nucleotides, especially with respect to complex genomic regions, such as regions with highly repetitive DNA. A total of 4,596,517 variants among the 52 individuals (2921142 SNVs, 667458 insertions, 752180 deletions, and 255737 multinucleotide variants and rearrangements) were 'novel'. For each of the 24,277,549 non-reference variant sites, the ancestral allele was identified using the chimp and Macaque genome comparisons as described in the Methods section. The ancestral allele for 676,185 variants was not determined due to limitations in the available chimp and Macaque reference assemblies. This amounted to 2.78% of the total variants observed. The likely functional effect of the derived allele was evaluated and the number and rate of variant functional category types per genome was catalogues.

General Population Comparisons

Figure 15A:
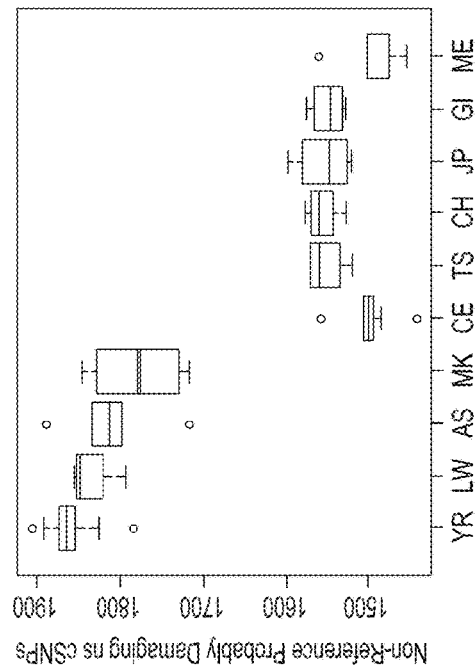
FIG. 15A provides a box plot depicting the differences in the absolute number of loci harboring non-reference alleles for each population. There are between 500,000-750,000 more loci with non-reference alleles in the genomes of African rather than non-African populations.
Figure 15B:
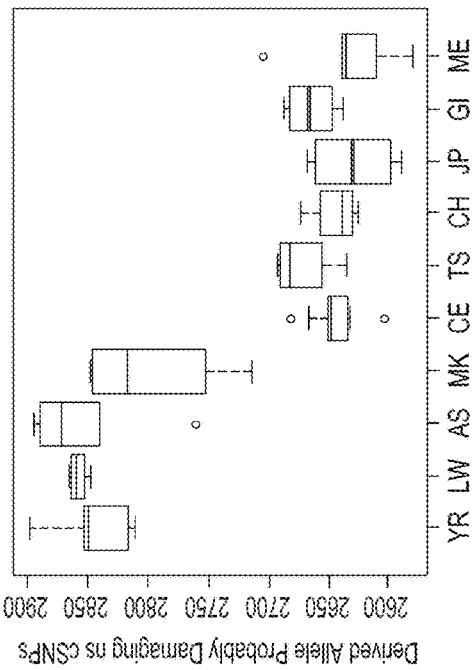
FIG. 15B depicts population differences in the number of 'probably damaging' (by Polyphen2 designation) non-reference, non-synonymous coding SNVs (ns cSNVs) (see Methods (Sunyaev et al., 2001)). Each genome has, on average, 1650 loci that harbor a 'probably damaging' non-reference ns cSNVs according to Polyphen2, with Africans having ~1.23 times more probably damaging non-reference ns cSNVs than non-African populations (~350 more ns cSNVs in absolute terms).

The frequency of variants in each of the defined functional categories across the 10 populations was compared via graphical and linear regression analyses and dramatic and statistically significant differences were discovered. FIG. 15A provides a box plot depicting the differences in the absolute number of loci harboring non-reference alleles for each population. There are between 500,000-750,000 more loci with non-reference alleles in the genomes of African rather than non-African populations. FIG. 15B depicts population differences in the number of 'probably damaging' (by Polyphen2 designation) non-reference, non-synonymous coding SNVs (ns cSNVs). Each genome has, on average, 1650 loci that harbor a 'probably damaging' non-reference ns cSNVs according to Polyphen2, with Africans having ~1.23 times more probably damaging non-reference ns cSNVs than non-African populations (~350 more ns cSNVs in absolute terms). Overall, it was discovered that virtually all forms of functional non-reference variants characterized are significantly more frequent in African rather than non-African populations. The number of 'novel' non-reference variants on each individual genome (i.e., variants only found on an individual genome in our dataset) was determined by eliminating variants that were present on the other 51 genomes. It was determined that, on average, a human genome has ~103,000 loci that harbor novel non-reference alleles, with non-African genomes harboring ~10,000-50,000 less. Consistency in the effect sizes and statistical significance of the African, European, and Asian populations, was discovered with some deviations from the East Indian (GI) and Mexican (ME) populations that likely reflect the unique population origins.

As noted, due to the fact that the human reference genome available from the UCSC genome browser is based on the DNA from individuals of European ancestry, it was not relied on for making claims about the frequency and rates of functional variants on genomes from individuals with different ancestries. Rather, the frequency and rate of derived alleles across the genomes were considered as a complement to comparisons involving non-reference alleles.

Figure 15C:
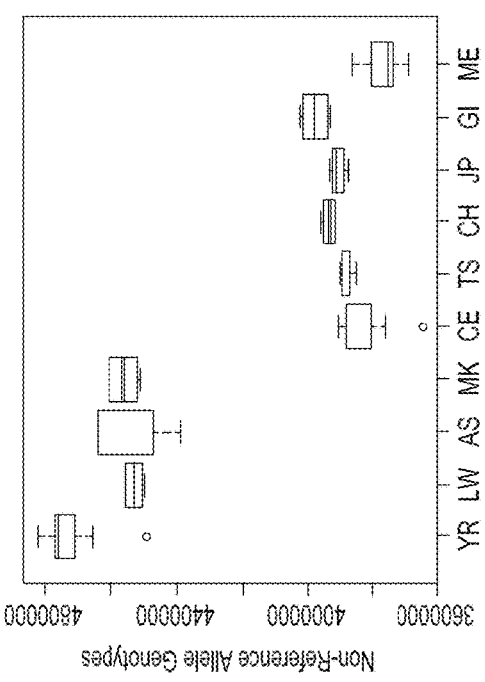
FIG. 15C and FIG. 15D depict the average number of derived variants on the genomes of individuals from the 10 different ancestral populations and the number of predicted probably damaging derived ns cSNVs, respectively.
Figure 15D:
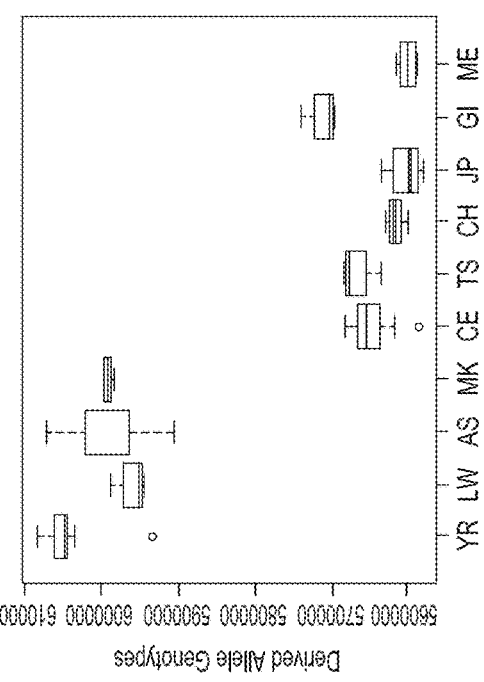

FIG. 15C and FIG. 15D depict the average number of derived variants on the genomes of individuals from the 10 different ancestral populations and the number of predicted probably damaging derived ns cSNVs, respectively. FIG. 15C suggests that African genomes possess ~6,000,000 loci that harbor derived alleles whereas non-African genomes possess ~350,000 less. This suggests that there are a great number of non-fixed derived variants in different human populations (i.e., variant sites for which ancestral and derived alleles are segregating in the human population at large). FIG. 15D suggests that the number of loci that harbor probably damaging derived ns cSNVs is ~2850 in African genomes and ~250 less in non-African genomes.

FIG. 21 (Table 1) presents the results of the regression analyses, and provides the estimated regression coefficients and their significance levels for each derived variant functional category. Note that since the YR African population was taken as the reference population, a negative regression coefficient means that genomes associated with a population have fewer variants, or a smaller per genome rate, for a derived variant category than the YR population. The upper rows of Table 1 clearly suggest that there are a greater number of derived variants or alleles within African genomes across virtually every functional variant category. The lower diagonal of Table 2 (FIG. 22) provides the results for analyses comparing the 10 populations on a pairwise basis for the total number of derived variants and suggests that although there are differences between populations in the same continent, they are not as pronounced as the differences between continental populations.

Homozygous Variant Comparisons

Differences in the frequency and per-genome rate of functional derived homozygous genotypes across the populations were tested for. FIG. 16 provides a graphical display of the results. FIG. 16A suggests that there is greater number of homozygous loci with derived alleles in non-African populations, and FIG. 16B suggests that there are a greater number of homozygous loci with probably damaging (PD) derived allele ns cSNVs in non-African populations as well. FIG. 16C and FIG. 16D suggest that there are a greater number of homozygous loci with likely functional derived alleles of any type and ultimately a greater rate of homozygous loci with likely functional derived alleles across entire individual genomes, respectively. This result—that despite the fact that African genomes have a greater number of derived variants and derived functional variants, there is a greater number and rate of homozygous derived and homozygous derived functional variants among non-African genomes—is consistent with the findings of other researchers. The bottom rows of Table 1 provide the regression analysis results for homozygous derived variants and clearly show that there is a significantly greater number and per-genome rate of homozygous functional derived variants in non-African populations.

Interestingly, although some evidence for consistency in the deviations of the non-Yoruban African and non-African populations from the Yoruban population with respect to numbers and rates of functional variants was discovered, there were more subtle, but statistically significant, differences in the total number and rates of different derived variant functional categories, including the number and rate of derived allele homozygous loci, between non-African populations (Table 2, contrast the entries above and below the diagonal). So, for example, the number of homozygous loci harboring derived, likely functional alleles differs between European and Asian as well as East Indian populations, but not necessarily between European populations and the admixed Mexican population (upper diagonal entries of Table 2).

Population-Specific Variant Comparisons

To further characterize the population-level differences in the functional content of individual genomes, the number of population-specific variants in European, Asian, and African populations were determined in a manner analogous to the methods describe in Example 16. FIG. 23 (Table 3) provides the summary information for the total number of population specific variants as well as the per-variant rate of different functional variant categories for each population. The z-tests assessing the equality of derived functional variant category frequencies are also provided in Table 3. As can be seen, there are significantly higher rates of population-specific likely functional derived variants per genome across virtually all functional variant categories in European and Asian populations relative to the African population, despite there being more population specific variation within the African population (top row). However, there are virtually no significant differences in these rates between European and Asian populations (Table 3, last column).

As noted, in addition to comparing population summaries, the rate of population-specific, likely functional variants in each individual genome within each population, was also determined. This is important since sample size differences could impact the ability to identify and test frequency differences of rare and population-specific variants if only population summary statistics over the genomes are considered, as in Table 3. It was determined that there are higher rates of functional variants among the population-specific variants within European and Asian genomes relative to African genomes despite the fact the rate of such variants is higher across the combined variants (i.e., not just population-specific variants) in African rather than European and Asian genomes.

Simulation Study Results Using Known Pathogenic Variants

Two factors go into the inference that a variant is likely to be pathogenic and causative of an idiopathic condition are the variant must be unique to the patient with the condition (i.e., 'novel') and it must be predicted to be functional. Determining the novelty of a variant requires contrasting the patient's genomic variants with variants on other individuals' genomes (i.e., a reference set of genomes). Determining functionality requires the use of bioinformatics techniques, if not direct laboratory-based functional assays.

Thus, in order to determine the likely impact of these findings on searches for pathogenic variants influencing idiopathic diseases, the number of ns cSNVs in 5 target individuals' genomes (i.e., a European, African, Mexican, East Indian, and Puerto Rican simulated patient's genome) was considered. It was considered as likely pathogenic beyond known dominant-acting CMT syndrome-inducing variant and recessive-acting CF-inducing variants when compared to different reference panel genome' ns cSNV lists derived from the 52 individuals for which WGS information was available. The use of reference sets made up of data from the 1000 genomes project (www.1000genomes.org/) was also considered.

Polyphen2, SIFT, and the average Polyphen2 and SIFT scores were computed for the CMT and CF variants, ns cSNVs variants in each of the 5 target individual's genomes and ns SNVs in each reference data set. The assessment was limited to ns cSNVs due to the low coverage sequencing in non-coding regions pursued in the 1000 Genomes project. FIG. 24 (Table 4) provides the number of variants that would be considered both novel and as having a predicted functional effect score at least a large as the known disease-causing variants relative to the variants. Table 4 only provides the results when considering the dominant-acting CMT mutation as the pathogenic variant to be identified. The upper rows consider analyses that only use Polyphen2 scores, the middle rows the use of SIFT scores, and the bottom rows use the average Polyphen2/SIFT scores as a way of assessing the functional effects of the ns cSNVs. The columns correspond to the use of different reference variant sets for determining the novelty of a variant.

Note that since the non-European target individuals we assessed were part of the 69 WGS individuals studied, the use of a combined reference set with 1000 Genomes and the 69 WGS genomes data (i.e., the 'ALLDB' column of Table 4) could not be considered. From Table 4, it can be seen that one could expect some 194 ns cSNVs to be called as 'novel' that have Polyphen2 scores greater (and hence likely to be functional) than the known CMT mutation for the European individual we studied based on the use of a 1000 Genomes-derived European reference ns cSNV panel; 680 if a 1000 Genomes-derived African reference panel is used; and 439 if an 8 member reference panel was constructed from the ns cSNVs from the WGS data studied. These would be out of a total of 1539 ns cSNVs for this European individual. These numbers represent the number of 'false leads' one would have to deal with in trying to identify the known causative variant (i.e., the 'implanted' CMT variant).

Table 4 also suggests that the use of different algorithms for predicting the likely functional significance of variants makes a difference (contrast the entries between the top, middle, and bottom sets of rows), possibly the use of sequencing platforms (as indicated by the small decrease in false positive results from the use of the 1000 Genomes reference panels vs. the only 8 member WGS panel provided by the CGI data) and most importantly the genetic background of the members in the panel (i.e., contrast the columns that only consider the 8 member panels derived from the WGS data). Similar results were observed when assessing the novelty of homozygous variants and the scoring of the likely functional significance of the known CF mutation.

Figures 17A, 17B:
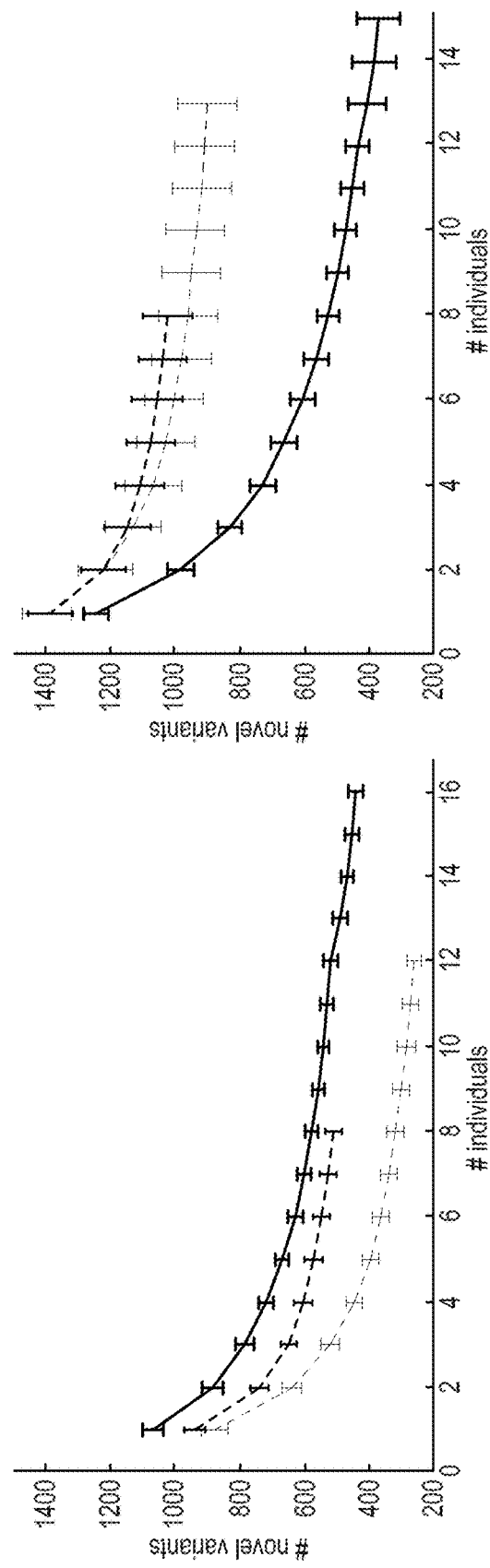
FIG. 17A shows the relationship between the number of ns cSNVs with polyphen 2.0 scores>0.8 that would be declared as novel if a European individual's ns cSNVs were compared to a reference panel made up of European, African or Asian individuals as a function of the number of individuals in the panel. Standard errors were computed by taking a randomly choosing the number of individuals from our collection of European, African and Asian genomes given on the x axis.
FIG. 17B shows the relationship between the number of ns cSNVs with polyphen 2.0 scores>0.8 that would be declared as novel if an African individual's ns cSNVs were compared to a reference panel made up of European (light dashed and dotted line), African (black solid line) or Asian individuals (dashed light line) as a function of the number of individuals in the panel. Standard errors were computed by taking a randomly choosing the number of individuals from our collection of European, African and Asian genomes given on the x axis.
Figure 20:
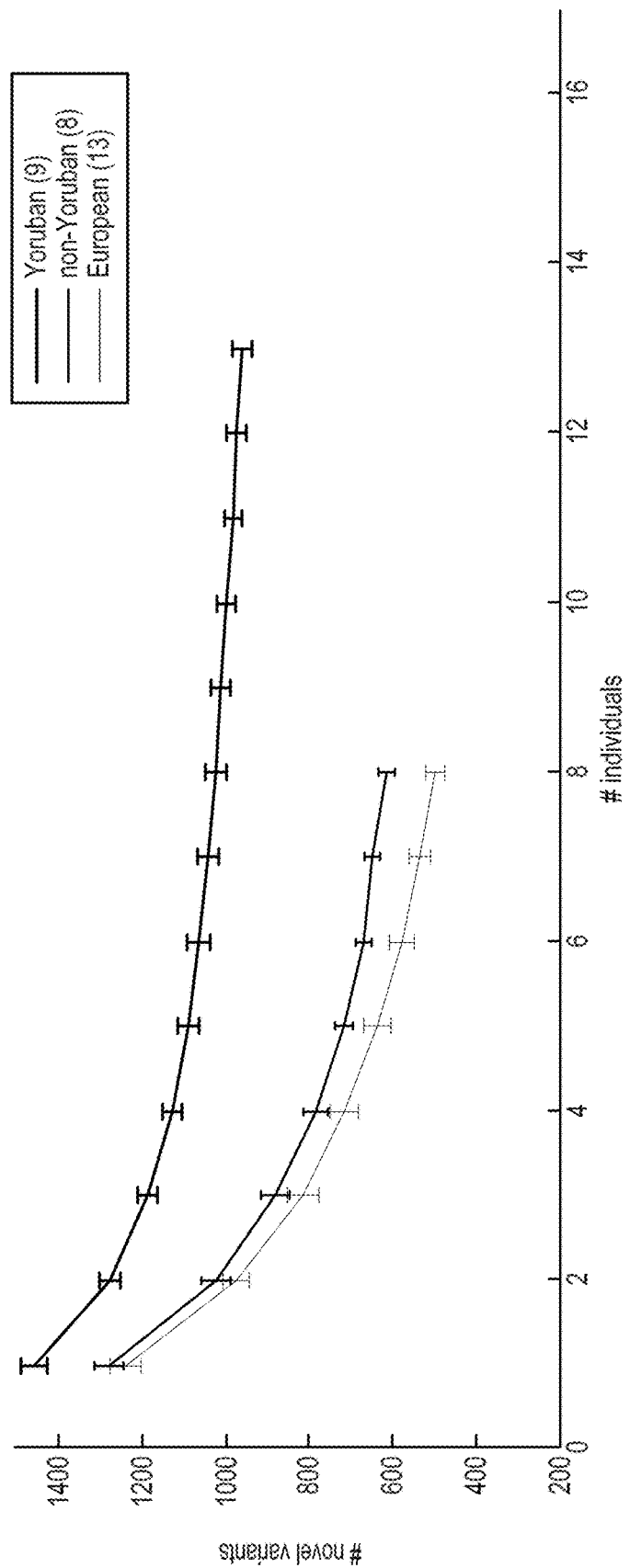
FIG. 20 illustrates the relationship between the number of ns cSNVs with polyphen 2.0 scores>0.8 that would be declared as novel an African individual's ns cSNVs were compared to a reference panel made up of European, African Yoruban or African non-Yoruban individuals as a function of the number of individuals in the panel. Standard errors were computed by taking a randomly choosing the number of individuals from a collection of European, African Yoruban or African non-Yoruban individuals give on the X axis.

The impact of the addition of genomes to a reference panel on potential 'false lead' rates in pathogenic variant identification was also considered. FIG. 17 depicts the relationship between the number of variants with Polyphen2 scores greater than 0.8 that would be determined as novel on a European (FIG. 17A) and African genome (FIG. 17B) if reference panels were comprised of increasing numbers of European, African, and Asian individuals. It is quite clear from FIG. 17 that including individuals with appropriate genetic backgrounds in reference panels for determining the novelty of variants is crucial for reducing false leads and appropriately ranking likely pathogenic variants. Similar patterns were observed when considering analyses of an African individual's genome wide ns cSNVs when using different (within) African population reference panels (FIG. 20) but with a lesser overall effect than if non-African individuals are used to construct the reference panel.

CONCLUSION

The differences in the genome-wide rates of DNA sequence variants associated with different genomic functional elements across 10 contemporary global populations were assessed. Evidence that historical population-level phenomena of whatever sort, including possibly bottlenecks, unique migratory patterns, admixture, natural selection, and random drift, have left an imprint on the standing genetic variation that is likely to influence phenotypic expression in these populations. In this light these results are consistent with previous reports, but extend them to the entire genomes of individuals from many different global populations. Important functional variant categories were considered and genomes sequenced on a single platform and to great depth (~60×) were used. Importantly, it was determined that, on an individual genome-wide basis, there is both an absolute and proportionately greater number and rate of loci that are homozygous for derived alleles that are likely to be functional in non-African populations.

The results of the research described herein suggests that whole genome sequencing will not only be of tremendous value in future population genetic and human evolutionary studies, but also that global human population differences in rates of novel, deleterious or functional variants must be taken into account in certain clinical sequencing applications. Importantly, the results emphasize the need for care in evaluating the novelty or likely functional impact of variants in clinical sequencing studies focusing on the identification of disease-inducing 'pathogenic' variants in an individual genome based on comparisons of that genome to a reference panel of genomes. This is the case because of the tremendous diversity of variants across human populations, the existence of an abundance of likely functional variants that are population-specific, and population differences in the absolute number and rates of homozygous variants that are likely to impact phenotype expression. Thus, for example, it might be highly problematic to evaluate the novelty of variants in the genome of an African patient in order to filter out variants not likely to cause his or her unique disease by comparing that individual's genome to a reference panel that only includes genomes from individuals with European ancestry. This problem might be particularly pronounced in large urban centers where individuals with a wide variety of ancestries may require medical care.

Example 9: Identification of Candidate Disease-Causing Variants

Figure 6:
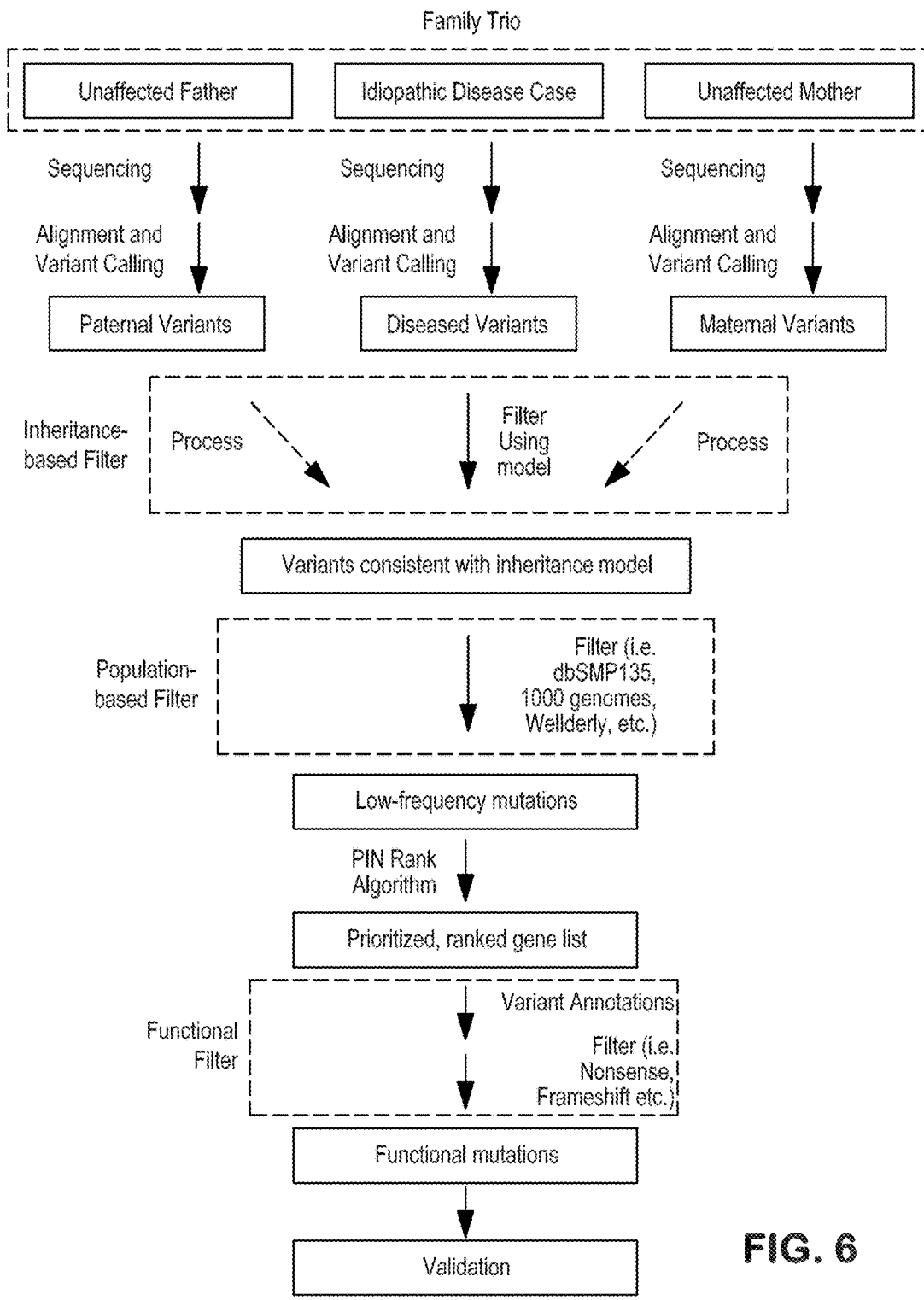
FIG. 6 is a general workflow and analysis of an example clinical sequencing case. Studies often include sequencing of family trios and variant filters based on inheritance patterns, population-specific allele frequencies, and predicted functionality.

FIG. 6 provides an overview of the general filters currently used to derive a set of candidate disease-causing mutations in a clinical sequencing study. Typically, focus is on an affected proband with at least a few related affected and/or unaffected family members. These family members can be studied with the proband, via inheritance-pattern based filters, to narrow the number of variants likely to contribute to the disease. For example, variants only within shared chromosomal segments among related affected individuals, or de novo or compound heterozygous variants in the case of an affected child with unaffected parents might be considered further.

Standard probabilistic inheritance-based filters have been described in the literature and are essentially extensions of classical linkage and pedigree-based haplotype-sharing analysis methods. Following the application of inheritance-based filters, if any are used, candidate disease-causing variants are further filtered based upon population data. Ideally, one would compare variants within an affected individual's genome to a reference panel of healthy genomes, such as a disease-free sample of individuals like the Wellderly population, and remove from further consideration variants observed within the healthy reference panel with an appreciable frequency. This filter is most useful for narrowing the number of potential compound heterozygotes and/or in the instances where parental genomes are unavailable. The ranking methodology described herein is applicable to candidate variants derived from any combination of genetic inheritance models and/or population-based filters.

Since the test cases explored did not include information on relatives and given the fact that a healthy genome reference panel does not currently exist, we restricted the application of methods for ranking and prioritizing candidate pathogenic variants to scenarios involving sets of novel variants within single affected individuals' genomes. As such, the first filtration step was to simply eliminate from consideration variants in an individual's genome that have been previously observed and catalogued in dbSNP135 and 1000 genomes databases, as well as in any other individual's genome dataset.

As an alternative to eliminating variants that are not novel or unique to a diseased individual's genome, it is possible to define reasonable allele frequency cutoff values consistent with related disease incidence and penetrance information. However, most idiopathic diseases attributable to genetic variants, the responsible variants will be ultra-rare (i.e., likely <<1% allele frequency, de novo, or simply never observed before and hence novel). Ultimately, the number of candidate disease-causing mutations (described below) to be ranked under with this analysis approach and PIN rank algorithm is an order of magnitude larger than the number of likely candidate-disease causing mutations to be considered if parental information and/or a complete healthy genome reference panel were available making the application and assessment of our proposed methodology on such a set of candidate mutations a true challenge.

The remaining candidate variants (i.e., those that are deemed novel or rare enough to be considered) were then filtered based upon functional annotations and the application of functional prediction algorithms, such as SIFT and Polyphen2. Since there is some danger that the disease-causative variant is not identified as a functional variant by available predictive algorithms, given that such algorithms do not have perfect accuracy, filtration based upon functional annotations was performed after candidate gene ranking. Nevertheless, the reported sensitivity and specificity of functional prediction algorithms suggests that this filter will improve accuracy in the majority of cases. The number of candidate-disease causing mutations passing this filtration step is on the order of what is expected to pass inheritance-based filters without functional annotation-based filtration, thus, this analysis also serves as a benchmark for the accuracy of our approach when family genomes are available.

In summary, the candidate disease-causing variants this approach considers further must be novel and impact protein function if they meet the following functional criteria: (1) they are nonsense SNVs (16.19% of known disease-causing variants in our test set); (2) they are frameshift indels (13.39%); or (3) they are nonsynonymous coding variants with no further functional annotation based filtration (70.42%). When functional annotation filters are applied, nonsynonymous coding variants must be within conserved elements as assessed by PhastCons, and labeled as 'Probably Damaging' by PolyPhen-2, and 'INTOLERANT' by SIFT (21.34%). These candidate variants are then subjected to PIN rank algorithm for further prioritization and ranking. These two extremes in variant annotation based filtration serve to represent the lower and upper bounds of the accuracy of this approach.

Example 10: Test Gene-Disease Associations and Genetic Networks

To be certain that the results of the PIN rank algorithm accurately reflected its ability to detect novel gene-disease associations, steps were taken to ensure that the influence of knowledge generated after the discovery of the test disease genes was removed from simulation.

To do this, a genetic network and a set of test gene-disease associations was curated in a manner that ensures no gene-gene interactions within the genetic networks were derived from publications, or other functional studies, that may have been pursued as a direct or indirect result of the discovery of the test gene-disease associations.

This was accomplished by compiling a list of recent (post 2001) gene-disease associations via the Human Gene Mutation Database (HGMD) and filtering that list for disease-causing genes not associated with any disease prior to 2011 but where the associated disease has been associated with at least one additional gene prior to 2011. The genetic network was derived from String Database (StringDB) version 8.2 (21), last compiled on May 26, 2010. This network selection and test gene filtration ensured that the list of test genes did not contain any genes that may have been associated with similar diseases prior to 2011 that could have thus resulted in experimental investigations into gene-gene relationships that may favor the performance of our ranking methodology, acts to facilitate automated and unbiased selection of seed genes for the PIN Rank algorithm, and ensured that the gene rankings reflect rankings that would have been achieved prior to the discovery of the test gene-disease associations.

The total number of test gene-disease associations surviving this filtration was 132, broken down as 112 genes distributed across 109 diseases. The final list of test gene-disease associations and the seed genes used in our ranking approach are available in FIGS. 25A-D (Table 5), FIGS. 26A-C (Table 6) and FIGS. 27A-V (Table 7). These requirements serve only to control for subjective biases in seed gene selection, and are not necessary requirements for the application of our approach generally.

Example 11: Simulated Diseased Genomes 69 publically available genomes were downloaded from Complete Genomics. The variants within these genomes, were filtered as described in Example 10 and annotated according to the following method:

Genomic Elements and Conservation

All variants were mapped to the closest gene from the UCSC Genome Browser known gene database. Variants were associated with transcripts of the nearest gene(s) with impact predictions made independently for each transcript. If the variant fell within a known gene, its position within gene elements (e.g. exons, introns, untranslated regions, etc.) was recorded for future impact predictions depending on the impacted gene element. Furthermore, variants falling within an exon were analyzed for their impact on the amino acid sequence (e.g., nonsynonymous, nonsense, frameshift, etc.).

All variants were also associated with conservation information in two ways. First, variants were associated with conserved elements from the phastCons conserved elements (28way, 44way, 28wayPlacental, 44wayPlacental, and 44wayPrimates). These conserved elements represent potential functional elements preserved across species. Conservation was also assessed at the specific nucleotide positions impacted by the variant using the phyloP method. The same conservation levels as phastCons were used in order to gain higher resolution into the potential functional importance of the specific nucleotide impacted by the variant.

Protein Coding Variants

While interpretation of frameshift and nonsense mutations is fairly straightforward, the functional impact of nonsynonymous changes is highly variable. A number of different methods for prediction of their functional impact are available, however, the PolyPhen-2 and SIFT algorithms were selected, which perform favorably in comparison to other available algorithms, for prioritization of nonsynonymous single nucleotide substitutions. PolyPhen-2 utilizes a combination of sequence-based and structural predictors to predict the probability that an amino acid substitution is damaging, and classifies variants as benign, possible damaging, or probably damaging, and SIFT estimates the probability of a damaging missense mutation leveraging information such as conservation, hydrophobicity, and amino acid position, to classify variants as 'tolerant' and 'intolerant'.

These genomes consist of 26 individuals with European ancestry, 20 individuals with African ancestry, 8 individuals with Asian ancestry, 4 African-Americans, 4 Native Americans, 4 Mexicans, and 3 Puerto Ricans. Each test gene-disease association was then implanted into each of the 69 genomes, resulting in a total of 6,141 simulated diseased genomes (69 genomes×89 test gene-disease associations=6,141 simulated diseased genomes). Post population-based and annotation-based filtration, an average of 240 and 25 variants passed the filtration scheme per genome, respectively, with a range of 36-648 and 8-46 variants per genome (FIGS. 28A-B, Table 8).

Example 12: Overall Ranking Results

For each implanted known disease causing mutation (implanted KDCM), post-filtration genomic variants plus the implanted KDCM were ranted using the PIN rank algorithm (described in Example 16) (FIGS. 25A-D, Table 5; and FIGS. 26A-C, Table 6).

Figure 7:
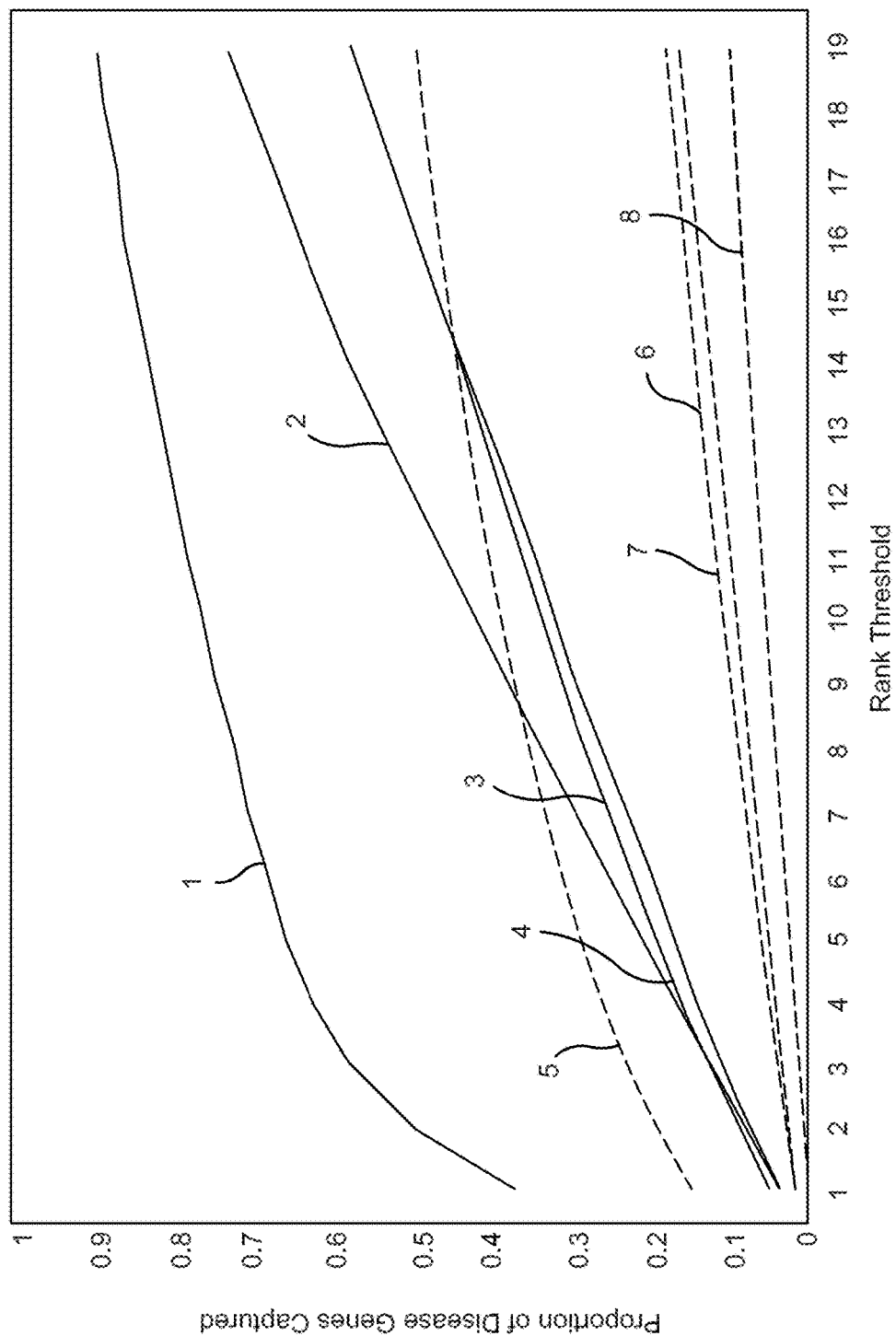
FIG. 7 is the cumulative proportion of disease genes captured by our methodology at different rank thresholds, with and without functional filters. Solid line (1) provides observed results with functional filters, Solid line (2) illustrates results of one million Monte Carlo simulations with functional filters, assigning random ranks to variants, Solid lines (3) & (4) show permutation of seed genes of the disease variants that scored within the top one (3) and top three (4) with functional filters, dashed line (5) shows observed results without functional filters, dashed line (6) shows results of one million Monte Carlo simulations without functional filters, assigning random ranks to variants, dashed lines (7) & (8) show permutation of seed genes of the disease variants that scored within the top one (7) and top three (8) without functional filters.

Without functional filters the known disease-causing variant was in the top 10% of candidate variants in 54% of cases (out of ~240 candidates), the #1 ranked variant in 15.80% of the cases and was present in the top three ranked variants 24.18% of the time (FIG. 7), as compared to 10%, 0.5% and 1.79% expected by chance.

Figure 8:
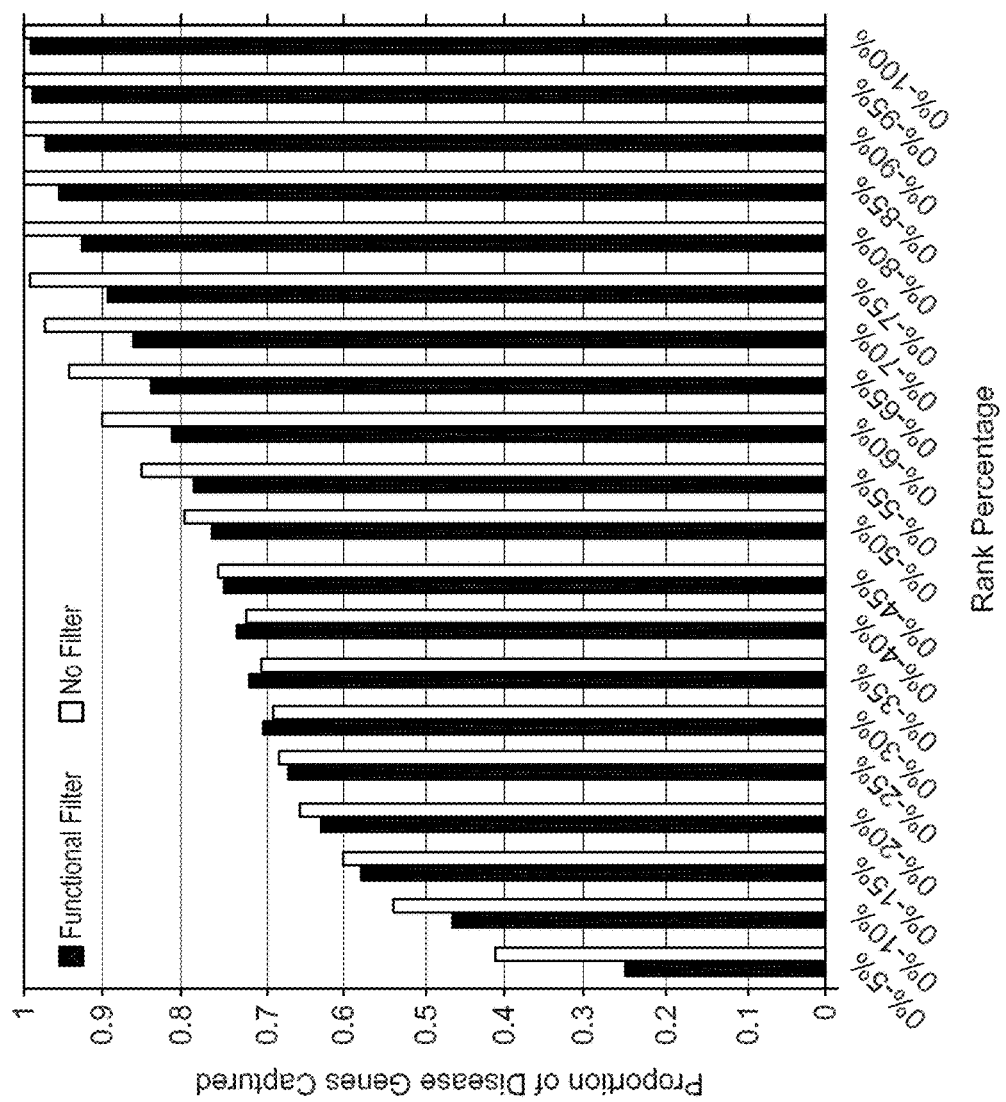
FIG. 8 is the cumulative proportion of disease genes captured by our methodology at different percentage bins. Black bars provide the results with functional filters and the grey bars provide the results without functional filters.

With functional filters, the known disease-causing variant was in the top 10% of candidate variants in 47% of cases (out of ~25 candidates) the #1 ranked variant in 37.16% of the cases and was present in the top three ranked variants 57.99% of the time (FIG. 7), as compared to 10%, 4.33% and 13.0% by chance. In general, ~70% of known disease-causing variants are prioritized to the top 25% of candidate disease genes (FIG. 8).

Clearly, the proposed ranking methodology produced a much greater proportion of successes than expected by random ranking (p-value<1e-06), performs extremely well in the case where the number of candidate variants was reduced by family based or functional filtration, and performs well even in the most extreme case where there is very little information available to narrow down the list of candidate variants except for the use of our proposed ranking approaches.

In order to confirm that the success of the ranking methodology stemmed from the methodology itself, and the use of appropriate known disease causing gene seeds, rather than some other general characteristic of the accurately-identified disease causing genes, the test gene-disease associations where the median rank across 69 genomes was at worst rank 3 were selected, and the set of seed genes used to rank each test gene-disease association were randomly swapped. Each high ranking test gene-disease association was then ranked with the seeds from other high ranking test gene-disease associations and the median achieved rank is presented in FIG. 7.

In the scenario with no functional filters, only 2.11% of the test gene-disease association re-rankings achieved rank #1, and 3.23% of the test gene-disease association re-rankings scored within the top 3. Similarly, with functional filters only 5.51% of the test gene-disease association re-rankings achieved rank #1, and 11.51% of the test gene-disease association re-rankings scored within the top 3. This performance is consistent with the performance observed by choosing random ranks, confirming that the methodology and selection of an appropriate seed gene set, rather than some general characteristic of disease causing genes, drives the performance of our ranking algorithm.

Example 13: Network Characteristics by Rank

The influence of network characteristics on the performance of the ranking methodology was investigated. To accomplish this, a determination was made as to whether disease gene connectivity, measured as degree and betweenness centrality, was correlated with ranking performance. Disease gene degree centrality was weakly but significantly correlated with ranking performance across 69 genomes (p-value=0.01, $r^2$=0.05 without functional filters, p-value=0.06, $r^2$=0.04 with functional filters) (FIG. 11A and FIG. 11B). Whereas, disease gene betweenness centrality was not significantly correlated with performance (p-value=0.05, $r^2$=0.02 without functional filters, p-value=0.56, $r^2$=−0.01 with functional filters) (FIG. 11C and FIG. 11D). A weak correlation with degree centrality suggests no major bias for the detection of hub-like disease genes vs. less well-connected disease genes.

Figure 9B:
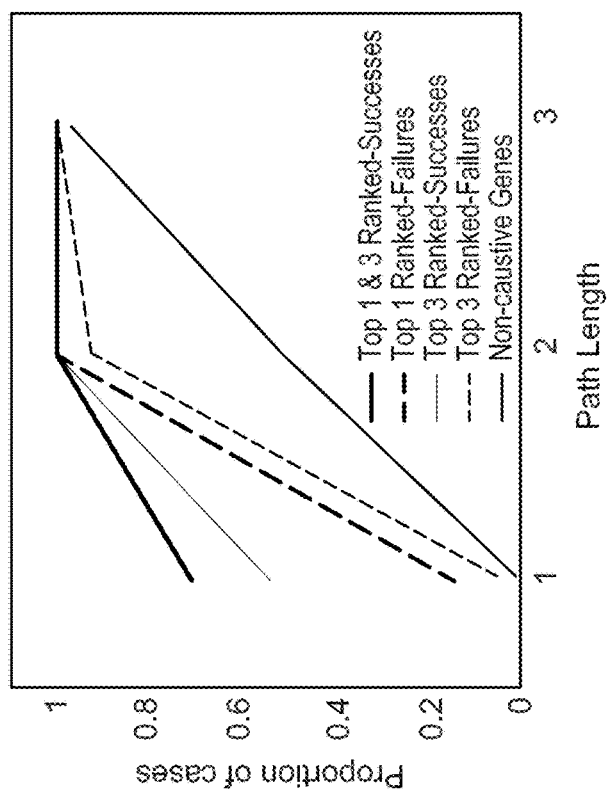
FIG. 9 is the path lengths of disease genes to its nearest seed gene when the disease gene was successfully or unsuccessfully identified as the top ranked gene or within the top three genes. This is compared to the path lengths from seed genes to other non-causative candidate genes.
FIG. 9A without functional filters and FIG. 9B with functional filters.
Figure 9A:
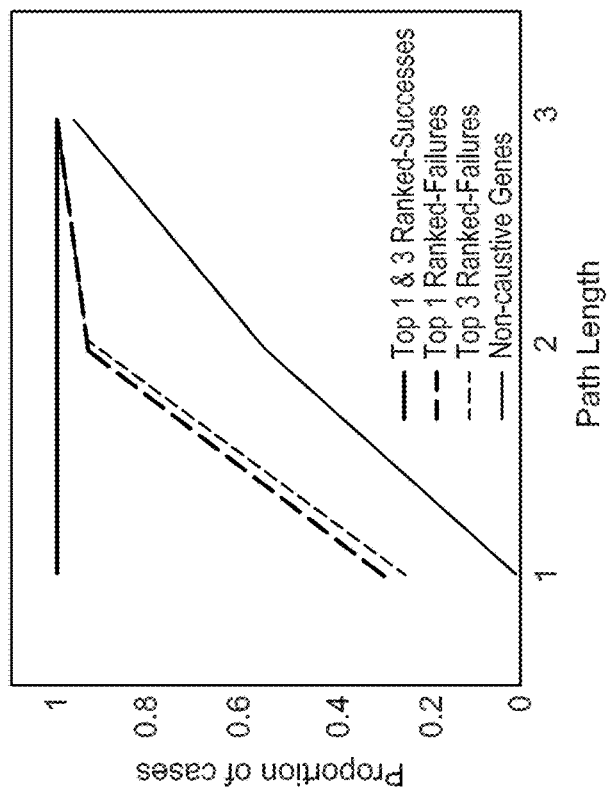
Figure 10:
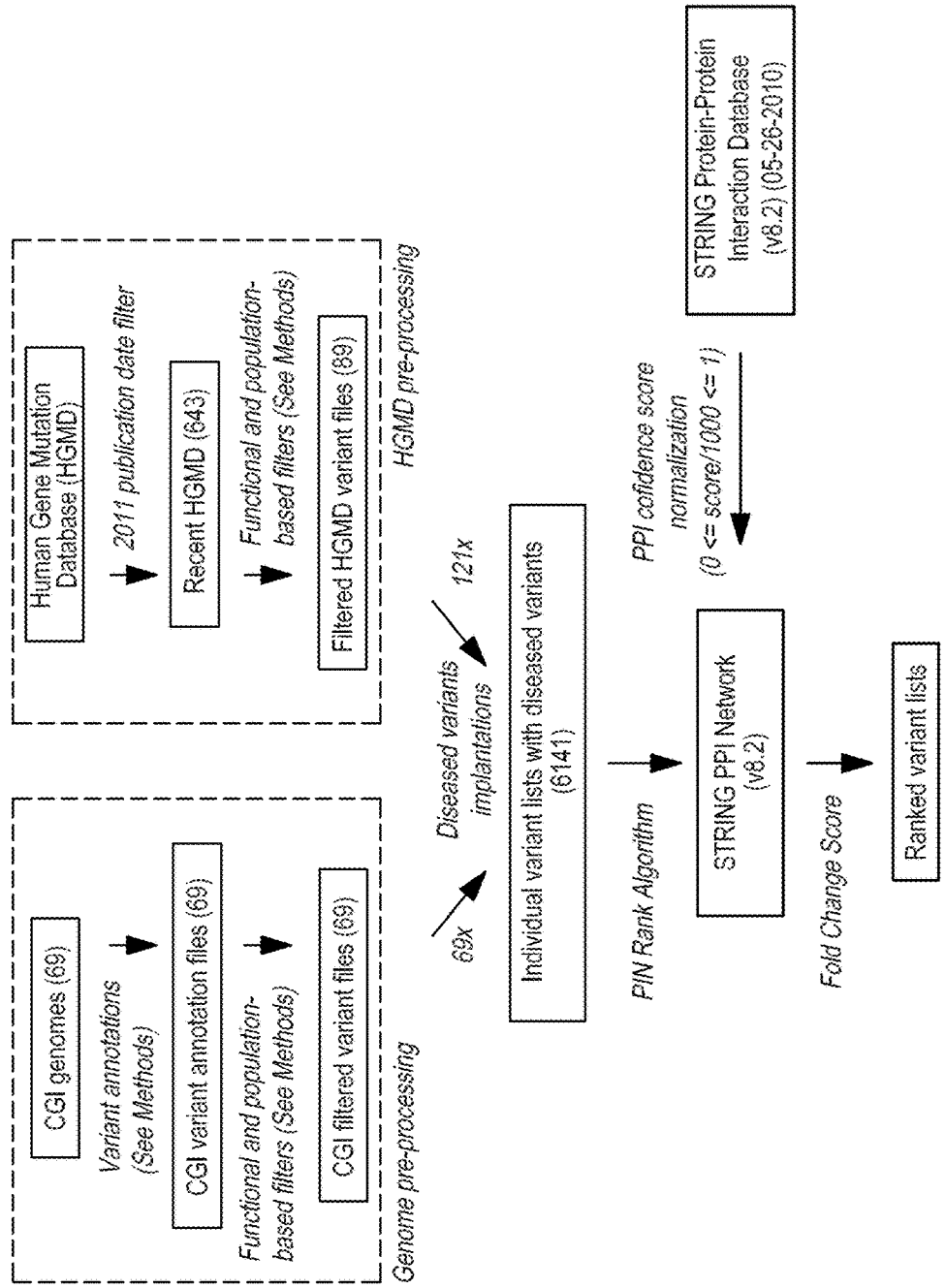
FIG. 10 is a workflow schematic describing how we prepared our Human Gene Mutation Database (HGMD) diseased variants and test genomes. After pre-processing, we implanted each diseased variant into every genome and scored the genes using the String Protein-Protein Interaction Database and PIN Rank algorithm.

Moreover, the path lengths from genes that passed the filtration criteria were compared to the nearest seed gene to the path lengths from successfully and unsuccessfully identified disease genes to the nearest seed gene. A disease gene was considered correctly classified when the gene was the top ranked gene or when the disease gene was ranked within the top 3. As shown in FIG. 9A, in order to be successfully identified amongst a large number of potential candidates (no functional or genetic filtration), the known gene must be directly connected to a seed gene. Similarly, approximately ⅔rds of successful identifications can be attributed to a direct connection with a seed gene in the case with stringent filtration (FIG. 9B).

Example 14: Ranking by Ethnicity

Individuals from different ethnicities carry population-specific variants as well as differing numbers of predicted deleterious mutations. Thus, affected individuals from ethnic backgrounds divergent from the ethnic profile of the reference panel genomes, and/or variants used to train functional prediction methods, will likely affect which genes pass our population-based and functional filters for ranking.

Figure 12:
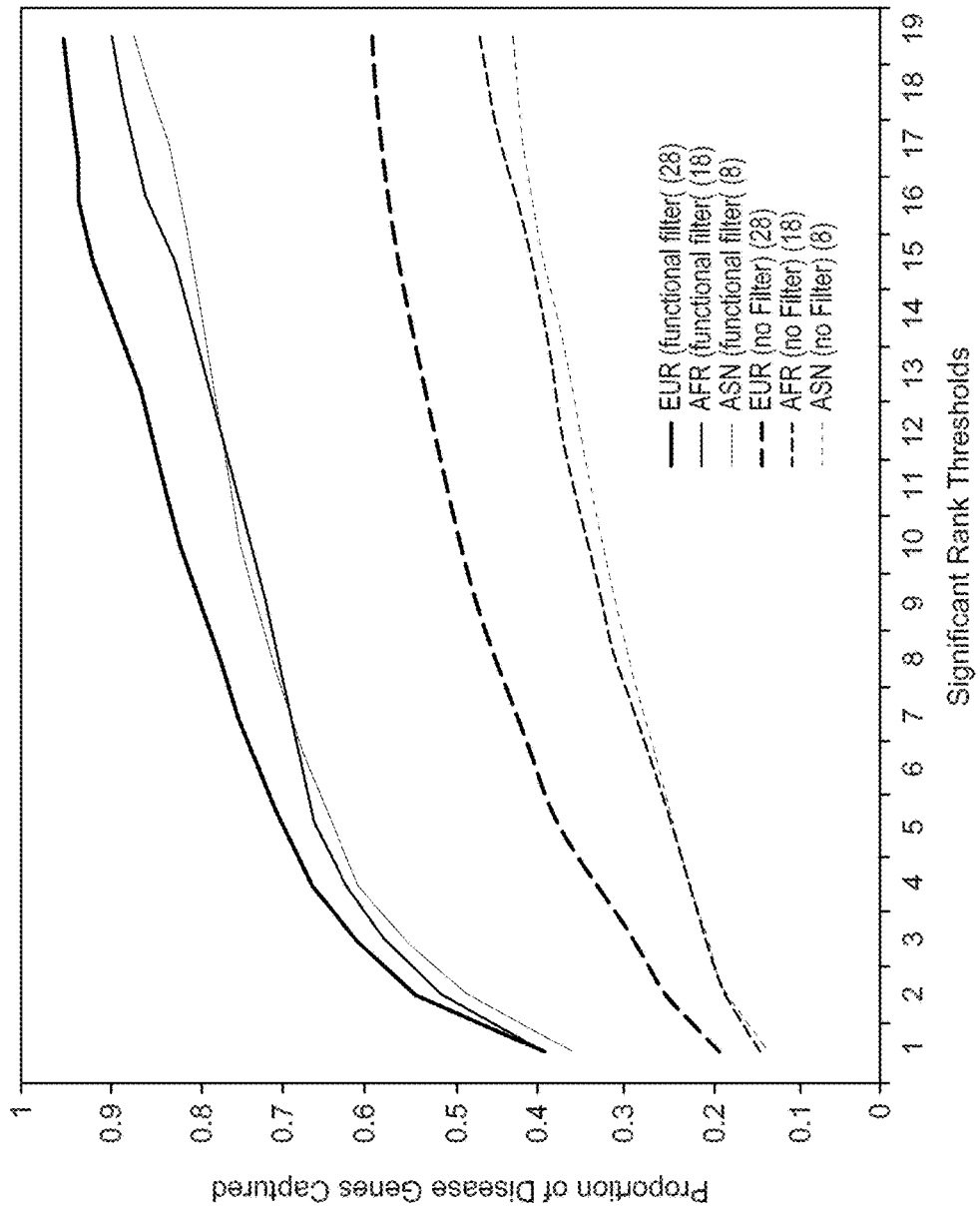
FIG. 12 shows a comparison of the performance of the rankings across different populations with functional filters (p-value=0.002) and without functional filters (p-value=4.12e-13), using a two-proportion z-test. EUR indicates European genomes, AFR indicates African genomes, and ASN indicates Asian genomes.

The influence of the ethnicity on disease gene ranking was evaluated by stratifying the data set into European (28), African (18), and Asian (8) populations. Overall, the ranking methodology performed best for European subjects (p-value=4.12e-13 without annotation filters, p-value=0.002 with annotation filters; two-proportion z-test), with disease-causing variants achieving the top rank in 19.03%, 13.51%, and 14.40% of our test cases without annotation filters and 39.95%, 36.07%, and 39.36% of the test cases with annotation filters in European, African, and Asian populations, respectively (FIG. 12).

Similarly, the disease-causing variant ranked within the top 3 variants in 29.59%, 20.95%, and 20.86% of the cases without functional filters and 61.42%, 56.05%, 57.83% of the cases with functional filters, respectively. This major bias, when no functional filters are used (and the number of candidates is large), demonstrates the massive gains in predictive power when appropriate filtration schemes are applied (population-based filters are heavily biased for European populations) and highlights the need for appropriate reference panels when conducting clinical sequencing studies in non-European populations.

The small bias between ethnicities when functional filters are utilized (and the number of candidates is moderate) also suggests that the ranking methodology is robust when additional filtration schemes, such as family information, are available.

Example 15: Identifying Accurate Instances of Ranking

Finally, given that in some instances the implanted KDCM were not highly ranked, reflecting the likely discovery of a disease gene with unknown function or novel mechanism of disease action, a measure of confidence in the ranking results would be useful for distinguishing a true positive vs. false positive instance of our ranking algorithm.

Figure 13A:
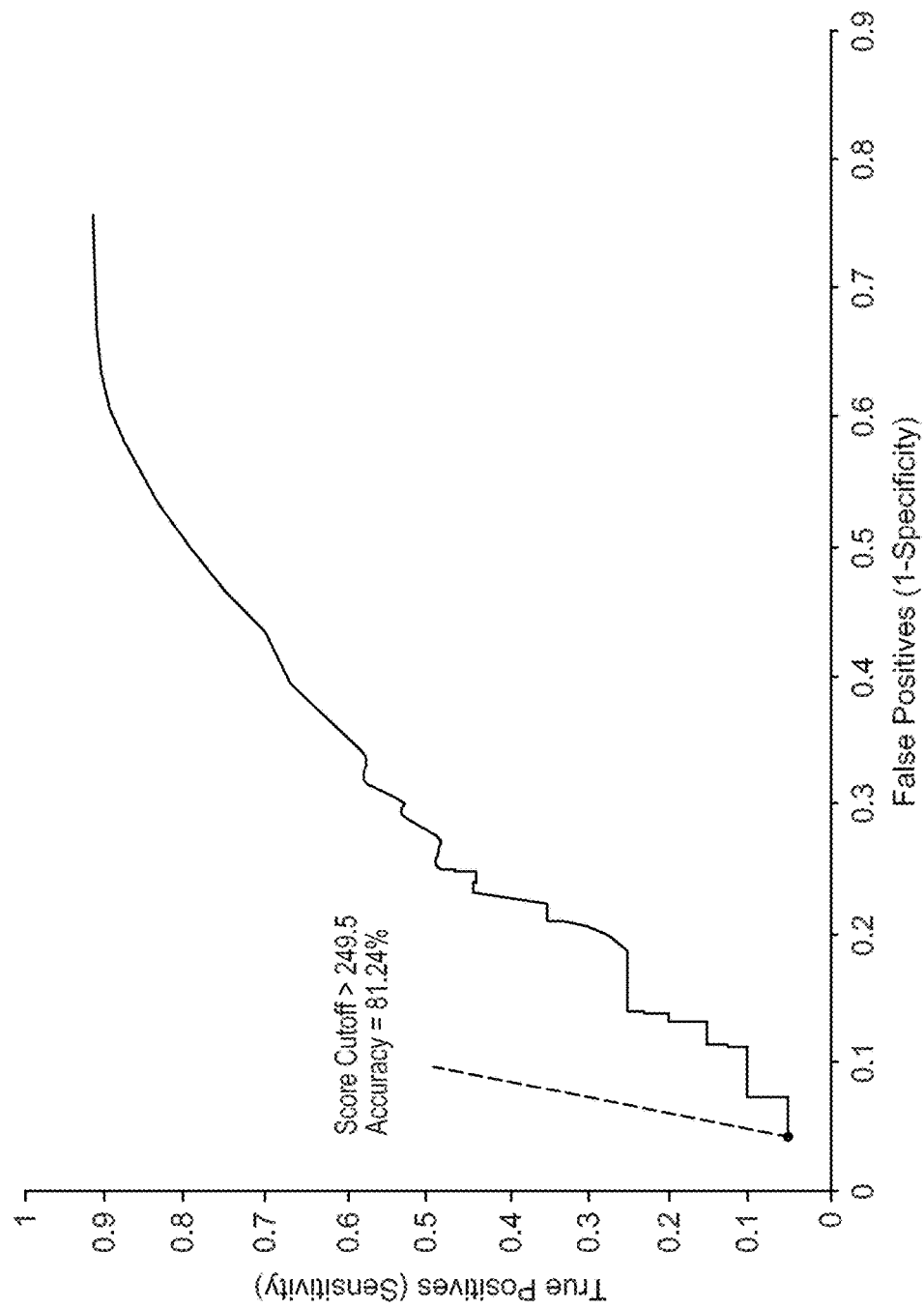
FIG. 13A is an ROC curve of ranking performance at different score thresholds for classification without functional filters (optimal cutoff>249.5; 5.2% sensitivity, 95.52% specificity, 81.24% accuracy).
Figure 13B:
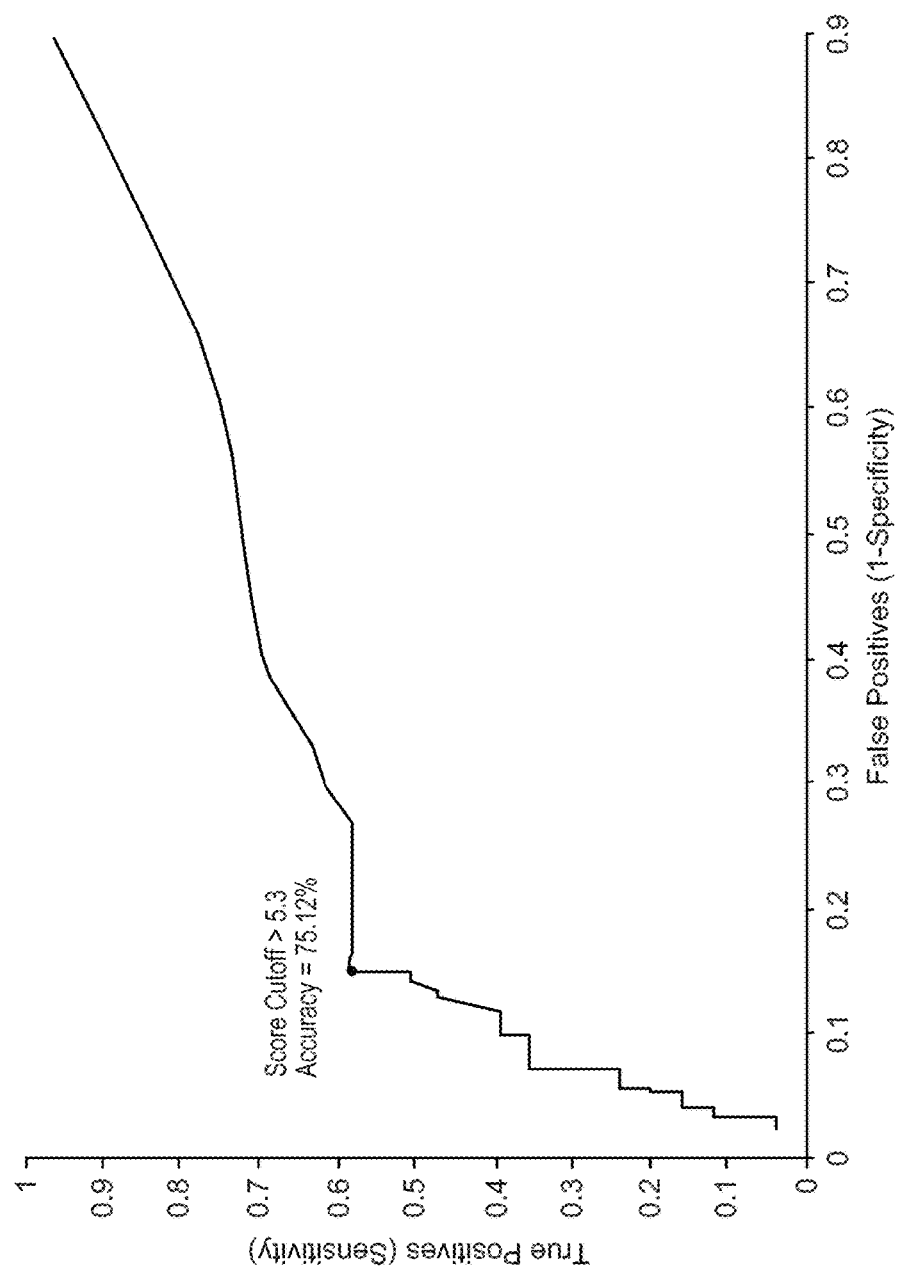
FIG. 13B is an ROC curve of ranking performance at different score thresholds for classification with functional filters (optimal cutoff>5.3; 58.4% sensitivity, 84.9% specificity, 75.12% accuracy).

This was accomplished by determining the specificity, sensitivity, and accuracy of the approach at different score cut-offs. Overall, a very high level of accuracy was achieved at a high score cutoff of 249.5 without functional filters (81.24% accuracy, 5.2% sensitivity, 95.52% specificity) and much broader accuracy with functional filters at a score cutoff of 5.3 (75.12% accuracy, 58.4% sensitivity, 84.9% specificity) (FIG. 13A and FIG. 13B). Thus, in most cases where the disease-gene has been successfully identified, the score of the top-ranked gene acts as an indicator for successful vs. inaccurate applications of our methodology.

These studies confirm that the combination of genetic analysis filters, population variant frequency filters, variant functional prediction and annotation filters, and gene-disease prioritization methods hold tremendous promise for accelerating the discovery of novel disease gene associations in the context of rare idiopathic conditions.

Discussion

The PIN Rank method, described herein, is similar to random walk-based methods but provides a number of advantages over previously described methods: (1) the PageRank core does not require a set path length but the diffusion length can be modified by varying its parameters; (2) computation over large graphs is straightforward and efficient; (3) it easily incorporates weighted edges so as to allow for confidence measures derived from different resources; (4) the fold change in PageRank vs. Personalized PageRank controls for the bias towards hub genes while appropriately enhancing the significance of hub genes local to seed genes; and (5) the teleportation matrix allows for the integration of numerous weighted selection strategies for the choice of seed genes.

The success of this approach clearly depends upon the selection of an appropriate seed gene list. In the example described herein, this selection was straightforward as it was based upon named diseases. However, the process can be streamlined to allow for extraction of seed genes, and weighting of those genes, for idiopathic diseases in a manner that is invisible to the user yet operates within their native vocabulary.

Previous work, in different contexts, has described systems that can convert phenotypic information, such as ICD9 codes, medical subject headings, phenotypic networks, or other phenotypic descriptions to seed gene lists. The integration of a seed gene list generation tool into the framework described herein would allow clinical implementation of this approach without the need for tremendous training or re-education.

Example 16: Methods

Test Genomes

Sixty-nine publicly available genomes were downloaded from the Complete Genomics website (http://www.completegenomics.com/sequence-data/download-data). The assembly of the genomes as well as the variant calling for these genomes has been described in the literature. Variants were mapped to the closest gene(s) from the UCSC Genome Browser known gene database and extracted nonsynonymous, nonsense, and frameshift variants.

Novel variants in each genome were extracted according to their absence in the dbSNP (v135) downloaded from the UCSC genome browser (www.genome.ucsc.edu), 1000 genomes (v2010-08-04) taken from the NCBI website (ftp://ftp-trace.ncbi.nih.gov/1000genomes/ftp/release/20100804/) and presence in other test genomes. The final variant sets included novel nonsense and frameshift variants as well novel nonsynonymous variants in the set without functional filters or novel nonsynonymous variants within conserved elements as denoted by PhastCons, and 'Probably Damaging' by PolyPhen-2, and 'INTOLERANT' by SIFT.

Test Gene-Disease Variants

The Human Gene Mutation Database (HGMD) (version 2011.3) was downloaded and used to build the test set of disease-causative variants and to select the disease seeds for the network-based ranking algorithm. The test set consisted of disease-causing variants mapped to genes that have not been associated with any disease prior to 2011. The set of seed genes consisted of other genes that have been associated to the test set diseases prior to 2011.

Phenotype-Informed Network Ranking

The phenotype-informed network ranking algorithm (PIN Rank) operates by ranking candidate disease causing genes based upon the fold-change in their basic PageRank vs. the phenotype-informed Personalized PageRank within a genetic network. The matrix notations for these two ranks are:

$$R = \alpha A R + (1-\alpha) T \tag{39}$$

Where A is a weighted undirected adjacency matrix containing the information regarding how different genes are linked to one another in the genetic network, T is a teleportation matrix containing the probabilities of randomly teleporting to each gene in the genetic network, α is an adjustable factor denoting how often one moves along the links within the adjacency matrix vs. teleporting to genes within the genetic network, and R is a vector of the ranks for each gene, or the equilibrium probability that one will arrive at each gene by following the links within the adjacency matrix or teleporting.

The final values within R are arrived upon by initiating R with equal probabilities for genes and solving by the power method—or iterating the above calculation until R stabilizes. For the basic PageRank, α is set at 0.99 and T is set at equal probabilities for every gene within the network, effectively removing any effect of teleportation upon the ranks of genes within the network while allowing R to stabilize in the face of dangling nodes or other factors known to disrupt R stabilization via the power method.

For the phenotype-informed Personalized PageRank, α is set at 0.95 and T is set so that teleportation results in equal probabilities of landing at a seed gene and zero probability of teleporting to any other genes within the genetic network. This effectively increases the rank of seed genes and genes within the network neighborhood of seed genes.

The values within the adjacency matrix A are derived from the probability that each gene is connected to another via StringDB, which integrates genomic context, known protein-protein interactions, co-expression, and literature mining to derive these probabilities. Link probabilities for each gene are scaled to the third power to down-weight low-probability links and then normalized.

For the phenotype-informed ranking algorithm (PIN Rank), α must be set to an appreciable value in order to optimize the probability of moving along links within the adjacency matrix and teleporting to genes within the network, as shown in:

$$R = \alpha AR + (1-\alpha)T \quad (10)$$

Where A is a weighted undirected adjacency matrix containing the information regarding how different genes are linked to one another in the genetic network, T is a teleportation matrix containing the probabilities of randomly teleporting to each gene in the genetic network, α ("alpha value") is an adjustable factor denoting how often one moves along the links within the adjacency matrix vs. teleporting to genes within the genetic network, and R is a vector of the ranks for each gene, or the equilibrium probability that one will arrive at each gene by following the links within the adjacency matrix or teleporting.

Additionally, protein-protein interaction probabilities must be raised to an appropriate power ("scale factor"), to accentuate stronger links from others. To determine the optimal values for these variables, we ran a preliminary analysis of the PIN Rank algorithm using combinations of scale factors between 1-5 and alpha values between 0.01-0.99, and compared the proportion of disease genes captured within the top 3 ranks with functional filters (FIG. 14). As a result, it was determined that alpha values up to 0.95 have greater accuracy and scale factors above and below 3 have moderately lower accuracy. More importantly, it was determined that a scale factor of 3 and alpha value of 0.95 produced the best results, capturing 57.99% of disease genes, therefore, we used these parameters for subsequent analyses in the manuscript.

This ranking methodology effectively integrates seed gene information from multiple sources and places some emphasis on nearby hub genes vs. less well connected genes as the ranks depend not only on the distance between nodes but also the importance of each node and its interacting partners within the network at large.

While certain embodiments have been described above, it will be understood that the embodiments described are by way of example only. Accordingly, the systems and methods described herein should not be limited based on the described embodiments. Rather, the systems and methods described herein should only be limited in light of the claims that follow when taken in conjunction with the above description and accompanying drawings.

All references cited herein, including patents, patent applications, and publications, are hereby incorporated by reference in their entireties, whether previously specifically incorporated or not.

While the disclosure has been described in connection with specific embodiments thereof, it will be understood that it is capable of further modifications. This application is intended to cover any variations, uses, or adaptations of the disclosure following, in general, the disclosed principles and including such departures from the disclosure as come within known or customary practice within the art to which the disclosure pertains and as may be applied to the essential features hereinbefore set forth.

The term "comprising," which is used interchangeably with "including," "containing," or "characterized by," is inclusive or open-ended language and does not exclude additional, unrecited elements or method steps. The phrase "consisting of" excludes any element, step, or ingredient not specified in the claim. The phrase "consisting essentially of" limits the scope of a claim to the specified materials or steps and those that do not materially affect the basic and novel characteristics of the claimed invention. The present disclosure contemplates embodiments of the invention compositions and methods corresponding to the scope of each of these phrases.

What is claimed is:

1. A computer-based genomic annotation system, comprising:
   non-transitory memory configured to store instructions, and
   at least one processor coupled with the memory, the processor configured to:
   receive a variant file including a plurality of genomic DNA variants relative to a reference genomic DNA sequence;
   generate an annotation file containing annotations corresponding to a plurality of predefined annotation categories for each of the plurality of variants in the variant file;
   wherein producing the annotation file comprises:
   generating data for the annotation file by mapping each of the plurality of genomic DNA variants to at least one known gene, wherein the mapping is created by:
      searching the reference genomic DNA sequence for known gene based on a single or multidimensional relative position of the variants with respect to one or more known genes, or on any other spatial or functional relationship relating the variants to known genes, including statistical, regulatory, or related to physical interactions,
      identifying at least one known gene nearest to each variant based on the searching, and generating a gene-based annotation that identifies the at least one known gene mapped to each variant of the plurality of genomic DNA variants;

generating a plurality of annotations in the annotation file for each variant of the plurality of genomic DNA variants, the plurality of annotations corresponding to the plurality of predefined annotation categories, wherein at least one of the plurality of generated annotations includes the gene-based annotation that identifies the at least one known gene, wherein the plurality of generated annotations further comprise additional gene-based annotations associated with the mapped genes, the additional gene based annotations comprising the following levels of annotation information: genomic elements, prediction of impact information, linking element information and prior knowledge; and populating the annotation file with the plurality of generated annotations, wherein substantially all of the annotated variants in the annotation file contain the gene-based annotation identifying at least one known gene; and output the annotation file.

2. The system of claim 1, wherein for each variant of the plurality of variants, the processor is configured to identify a gene that has a start or stop codon closest to the variant, and map the identified known gene to the variant.

3. The system of claim 2, wherein some of the variants of the plurality of variants are located between the start and stop codons of the variant's associated gene, and some of the variants are located outside the start and stop codons of the variant's associated gene.

4. The system of claim 2, wherein some of the variants of the plurality of variants are located outside the transcribed portions of the genome.

5. The system of claim 1, wherein the genomic elements comprise at least one of known genes, protein domains, transcription factor binding sites, conserved elements, microRNA (miRNA), binding sites, splice sites, splicing enhancers, splicing silencers, common single nucleotide polymorphisms (SNPs), Untranslated Regions (UTR) regulatory motifs, post translational modification sites, and custom elements.

6. The system of claim 1, wherein the prediction of impact information comprises at least one of coding impact, non-synonymous impact prediction, protein domain impact prediction, motif based impact scores, nucleotide conservation, miRNA targets, splicing changes, binding energy, and codon abundance.

7. The system of claim 1, wherein the linking element information comprises at least one of phase information, molecular information, biological information, protein-protein interactions, co-expression, and genomic context.

8. The system of claim 1, wherein the prior knowledge comprises at least one of phenotype associations, biological processes, molecular function, drug metabolism, genome-wide association study (GWAS) catalog, allele frequency, expression quantitative trait loci (eQTL) frequency, and text mining information.

9. The system of claim 1, wherein the gene-based annotations include genomic elements comprising transcription factor binding site motifs, and wherein functional element mapping comprises at least one of the following: scanning the transcription factor binding site motifs against an associated genome, determining the positions of the transcription factor binding site motifs relative to at least one known genomic element, and mapping the variant onto the at least one known genomic element.

10. The system of claim 1, wherein the processor is further configured to generate synthetic annotations based at least in part on the gene-based annotations.

11. The system of claim 1, wherein the processor is configured to filter the annotation file to remove variant entries that correspond to variants found in one or more reference genome sequences.

12. The system of claim 11, wherein the one or more reference genome sequences are derived from subjects having a selected ancestry.

13. The system of claim 11, wherein the one or more reference genome sequences are derived from subjects of a selected age and health status.

14. The system of claim 1, wherein the processor is further configured to:

receive or generate a set of seed genes predicted to be associated with a defined phenotype; and generate a measure of potential functional overlap between each gene in the annotation file to the genes in the set of seed genes.

\* \* \* \* \*